US008435740B2

(12) United States Patent
Gut et al.

(10) Patent No.: US 8,435,740 B2
(45) Date of Patent: May 7, 2013

(54) METHOD FOR HLA TYPING

(75) Inventors: Ivo Glynne Gut, Paris (FR); Ramon Kucharzak, Rostock (DE)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 0 days.

(21) Appl. No.: 12/881,867

(22) Filed: Sep. 14, 2010

(65) Prior Publication Data

US 2012/0157347 A1 Jun. 21, 2012

Related U.S. Application Data

(62) Division of application No. 10/580,646, filed as application No. PCT/IB2004/004115 on Nov. 26, 2004, now Pat. No. 7,820,377.

(30) Foreign Application Priority Data

Nov. 27, 2003 (EP) ..................................... 03292952

(51) Int. Cl.
*C40B 40/06* (2006.01)

(52) U.S. Cl.
USPC ........................ 435/6.11; 506/16; 536/24.33

(58) Field of Classification Search ............ 435/6, 91.2, 435/91.1, 6.11; 536/24.33, 24.1, 23.5, 23.1; 506/16
See application file for complete search history.

(56) References Cited

U.S. PATENT DOCUMENTS

| | | | | |
|---|---|---|---|---|
| 5,256,543 A * | 10/1993 | Pouletty et al. | ............... | 435/7.94 |
| 5,310,893 A * | 5/1994 | Erlich et al. | ................ | 536/24.31 |
| 5,449,605 A * | 9/1995 | Smulson et al. | ............. | 435/6.12 |
| 5,451,512 A * | 9/1995 | Apple et al. | .................. | 536/23.5 |
| 5,541,065 A * | 7/1996 | Erlich et al. | ................. | 435/6.12 |
| 5,545,526 A * | 8/1996 | Baxter-Lowe | ............... | 435/6.11 |
| 5,550,039 A * | 8/1996 | Trachtenberg | ................ | 435/91.2 |
| 5,552,275 A * | 9/1996 | Hui et al. | ........................ | 435/6.11 |
| 5,567,809 A * | 10/1996 | Apple et al. | .................. | 536/24.3 |
| 5,663,047 A * | 9/1997 | Obata et al. | ................... | 435/6.12 |
| 5,665,548 A * | 9/1997 | Erlich et al. | ................. | 435/6.11 |
| 5,882,238 A * | 3/1999 | Kim et al. | ........................ | 445/24 |
| 5,908,749 A * | 6/1999 | Mignot et al. | ................ | 435/6.11 |
| 6,103,465 A * | 8/2000 | Johnston-Dow et al. | .... | 435/6.12 |
| 6,500,614 B1 * | 12/2002 | Arguello et al. | ............. | 435/6.18 |
| 6,503,707 B1 * | 1/2003 | Baxter-Lowe | ............... | 435/6.12 |
| 6,528,261 B1 * | 3/2003 | De Canck et al. | ........... | 435/6.12 |
| 6,670,124 B1 * | 12/2003 | Chow et al. | ................... | 435/6.12 |
| 6,790,616 B1 * | 9/2004 | Moribe et al. | ................ | 435/6.11 |
| 7,060,438 B1 * | 6/2006 | Mougin et al. | ................ | 435/6.12 |
| 7,619,057 B2 * | 11/2009 | Wang et al. | .................... | 530/300 |
| 7,667,026 B2 * | 2/2010 | Hogan et al. | ................ | 536/24.33 |
| 7,718,362 B2 * | 5/2010 | Gao et al. | ..................... | 435/6.11 |
| 7,943,309 B2 * | 5/2011 | Chen et al. | .................... | 435/6.11 |
| 8,142,999 B2 * | 3/2012 | Chen et al. | .................... | 435/6.11 |
| 8,183,360 B2 * | 5/2012 | Mitra et al. | ................. | 536/24.33 |
| 8,193,331 B2 * | 6/2012 | Tsukada | ....................... | 536/24.3 |
| 2002/0197613 A1 * | 12/2002 | Canck et al. | ...................... | 435/6 |
| 2003/0180298 A1 * | 9/2003 | Old et al. | ............................ | 435/6 |
| 2004/0197862 A1 * | 10/2004 | Wucherpfennig et al. | ... | 435/69.1 |
| 2005/0112624 A1 * | 5/2005 | Moribe et al. | ..................... | 435/6 |
| 2007/0148641 A9 * | 6/2007 | Hetherington et al. | ........... | 435/6 |
| 2007/0298425 A1 * | 12/2007 | Hogan et al. | ...................... | 435/6 |
| 2008/0145846 A1 * | 6/2008 | Chen et al. | ........................ | 435/6 |
| 2009/0012261 A1 * | 1/2009 | Luo et al. | ..................... | 530/326 |
| 2009/0035776 A1 * | 2/2009 | Juan Otero et al. | ............... | 435/6 |
| 2010/0099081 A1 * | 4/2010 | de Canck et al. | ................. | 435/6 |
| 2010/0168390 A1 * | 7/2010 | Brix et al. | ..................... | 530/350 |
| 2010/0222227 A1 * | 9/2010 | Tam | ................................ | 506/9 |

(Continued)

FOREIGN PATENT DOCUMENTS

WO WO 00/65088 A 11/2000
WO WO 0065088 A2 * 11/2000

(Continued)

OTHER PUBLICATIONS

Cox ST, McWhinnie AJ, Koester RP, Heine U, Holman R, Madrigal JA, Little AM. Further diversity at HLA-A and -B loci identified in Afro-Caribbean potential bone marrow donors. Tissue Antigens. 2001. 57(1):70-2.*

Bugawan TL, Apple R, Erlich HA. A method for typing polymorphism at the HLA-A locus using PCR amplification and immobilized oligonucleotide probes. TissueAntigens. 1994.44(3):137-47.*

Rozemuller, "Reference panels for sequence based typing: Selection criteria for HLA-A and HLA-B", Technical Manual International Histocompatibility Working Group, 2000).*

(Continued)

*Primary Examiner* — Kenneth R. Horlick
*Assistant Examiner* — Olayinka Oyeyemi
(74) *Attorney, Agent, or Firm* — Foley & Lardner LLP

(57) ABSTRACT

A method for the identification of DNA sequence elements in complex and highly variable sequences is described. The method consists of identifying a short sequence element of several DNA bases (2-6 bases) at a given position in the genome simultaneously on all parental alleles. The method allows differentiating mini-haplotypes on different alleles in one analysis. The method consists of carrying out an enzymatic primer extension reaction with a combination of extension primers (pool of primers) and analyzing the products by mass spectrometry. The pool of primers is assembled in such a way that the primer extension product allows unambiguous identification of both the primer of the pool that was extended and the base that was added. The method of great utility for DNA sequences harboring many SNP's close to each other with many possible haplotypes. Such sequences are known in the Major Histocompatibility Complex (MHC). This method is particularly well suited for DNA-based HLA typing and in combination with a suitable selection of sites tested, it is superior in ease of operation to conventional HLA typing methods. We have identified sets of these assays for HLA-A, HLA-B, and HLA-DRB 1 that allow unambiguous four-digit HLA of each of these genes with between 11 and 28 queried markers.

2 Claims, 6 Drawing Sheets

U.S. PATENT DOCUMENTS

| | | | | |
|---|---|---|---|---|
| 2010/0279889 | A1* | 11/2010 | Mitra et al. | 506/9 |
| 2011/0212439 | A1* | 9/2011 | Chen et al. | 435/6.1 |
| 2011/0217308 | A1* | 9/2011 | Offner et al. | 424/141.1 |
| 2011/0262479 | A1* | 10/2011 | Burrows et al. | 424/194.1 |

FOREIGN PATENT DOCUMENTS

| | | | |
|---|---|---|---|
| WO | WO 02/08462 | A | 1/2002 |
| WO | WO 0208462 | A1 * | 1/2002 |
| WO | WO 02/18659 | A | 3/2002 |
| WO | WO 0218659 | A2 * | 3/2002 |

OTHER PUBLICATIONS

Sauer S, Gut IG. Extension of the GOOD assay for genotyping single nucleotide polymorphisms by matrix-assisted laser desorption/ionization mass spectrometry. Rapid Commun Mass Spectrom. 2003. 17(12):1265-72.*

Bunce M. PCR-sequence-specific primer typing of HLA class I and class II alleles. Methods Mol Biol. 2003. 210:143-71.*

Sauer S, Gut IG. Genotyping single-nucleotide polymorphisms by matrix-assisted laser-desorption/ionization time-of-flight mass spectrometry. J Chromatogr B Analyt Technol Biomed Life Sci. 2002. 782(1-2):73-87. Review.*

Worrall TA, Schmeckpeper BJ, Corvera JS, Cotter RJ. Allele-specific HLA-DR typing by mass spectrometry: an alternative to hybridization-based typing methods. Anal Chem. 2000. 72(21):5233-8.*

Sayer D, Whidborne R, Brestovac B, Trimboli F, Witt C, Christiansen F. HLA-DRB1 DNA sequencing based typing: an approach suitable for high throughput typing including unrelated bone marrow registry donors. Tissue Antigens. 2001. 57(1):46-54.*

Arguello R, Avakian H, Goldman JM, Madrigal JA. A novel method for simultaneous high resolution identification of HLA-A, HLA-B, and HLA-Cw alleles. Proc Natl Acad Sci U S A. 1996. 93(20):10961-5.*

Pastinen et al., "Multiplex, fluorescent, solid-phase minisequencing for efficient screening of DNA sequence variation," *Clinical Chemistry*, American Association for Clinical Chemistry, vol. 42, No. 9, 1996, pp. 1391-1397.

Worrall et al., "Allele-specific HLA-DR typing by mass spectrometry: an alternative to hybridization-based typing methods," *Analytical Chemistry*, Nov. 1, 2000, vol. 72, No. 21, pp. 5233-5238.

Leushner et al., "Automated mass spectroscopic platform for high throughput DR Beta typing," *Human Immunology*, vol. 61, No. Supplement 2, 2000, p. S126.

Tost et al., "Genotyping single nucleotide polymorphisms by mass spectrometry," *Mass Spectrometry Reviews*, vol. 21, No. 6, Nov. 2002, pp. 388-418.

Tost et al., "Molecular haplotyping at high throughput," *Nucleic Acids Research*, Oct. 1, 2002, vol. 30, No. 19, p. e96.

Sauer et al., "Extension of the good assay for genotyping single nucleotide polymorphisms by matrix-assisted laser desorption/ionization mass spectrometry," *Rapid Communications in Mass Spectrometry*, vol. 17, No. 12, May 9, 2003, pp. 1265-1272.

Sauer et al., "Genotyping single-nucleotide polymorphisms by matrix-assisted laser-desorption/ionization time-of-flight mass spectrometry," *Journal of Chromatography B*, Analytical Technologies in the Biomedical and Life Sciences, Dec. 25, 2002, vol. 782, No. 1-2, pp. 73-87.

Rozemuller, "Reference panels for sequence based typing: Selection criteria for HLA-A and HLA-B," 2000, retrieved from the Internet: URL:http://wwww.ihwg.org/tmanual/TMcontents.htm, retrieved on Jul. 5, 2004.

Ross et al., "Discrimination of Single-Nucleotide Polymorphisms in Human DNA Using Peptide Nucleic Acid Probes Detected by MALDI-TOF Mass Spectrometry," *Anal. Chem.*, vol. 69, pp. 4197-4202, 1997.

Ross et al., "High level multiplex genotyping by MALDI-TOF mass spectrometry," *Nature Biotechnology*, vol. 16, pp. 1347-1351, Dec. 1998.

Robinson et al., "Exon Identities and Ambiguous Typing Combinations," *Anthony Nolan Research Institute*, Oct. 2003.

Petersdorf et al., "Tissue typing in support of unrelated hematopoietic cell transportation," *Tissue Antigens*, vol. 61, pp. 1-11, 2003.

Liu et al., "Rapid Screening of Genetic Polymorphisms Using Buccal Cell DNA with Detection by Matrix-assisted Laser Desorption/Ionization Mass Spectrometry," *Rapid Communications in Mass Spectrometry*, vol. 9, pp. 735-743, 1995.

Little et al., "Detection of RET proto-oncogene codon 634 mutations using mass spectrometry," *J. Mol. Med.*, vol. 73, pp. 743-750, 1997.

Haff et al., "Single-Nucleotide Polymorphism Identification Assays Using a Thermostable DNA Polymerase and Delayed Extraction MALDI-TOFF Mass?Spectrometry," *Genome Research*, vol. 7, pp. 378-388, 1997.

Griffin et al., "Genetic analysis by peptide nucleic acid affinity MALDI-TOF mass spectrometry," *Nature Biotechnology*, vol. 15, pp. 1368-1372, Dec. 1997.

Fei et al., "MALDI-TOF mass spectrometric typing of single nucleotide polymorphisms with mass-tagged ddNTPs," *Nucleic Acids Research*, vol. 26, No. 11, pp. 2827-2828, 1998.

Ch'ang et al., "Detection of ΔF508 Mutation of the Cystic Fibrosis Gene by Matrix-assisted Laser Desorption/Ionization Mass Spectrometry," *Rapid Communications in Mass Spectrometry*, vol. 9, pp. 772-774, 1995.

Karas et al., "Laser Desorption Ionization of Proteins with Molecular Masses Exceeing 10,000 Daltons," *Anal. Chem.*, vol. 60, pp. 2299-2301, 1988.

Tost et al., "Genotyping Single Nucleotide Polymorphisms by Mass Spectrometry," *Mass Spectrometry Reviews*, vol. 21, pp. 388-418, 2002.

International Search Report issued on Jul. 11, 2005 for application No. PCT/IB2004/004115.

Notice of Allowance issued by the Examiner in U.S. Appl. No. 10/580,646 on Jun. 11, 2010.

Office Action issued by the Examiner in U.S. Appl. No. 10/580,646 on Oct. 15, 2009.

Office Action issued by the Examine in U.S. Appl. No. 10/580,646 on May 27, 2009.

* cited by examiner

CTAGAGAAGCCAATCAGCGTGCCGCGGGTTCCAGTTGCAAGCACCCACCCAGAGTCTCCTCAGACGCCGAGATGCTGGTGCCCCGAACCGTCCTC

CTGCTGCTCTGGGCCCTGGCCCTGACCCCGGAGCCCAAATGGCCTCTGCCGGAGGAGATGGAGAGGACCGGAGGCGGAGGGAGCCGCAGGACCT

GAGGAGCCGCGGAGGAGGGTCGGGCGGGTCTCAGCCCCTCACCCCCAGGCTCCCACTCATGAGTA*97\**TTTC*ACACCCTCCGTGTCCCGGGGAGCCCG

CTTCATCTCAGTGGGCTACGTGGACGACACCCAGTTCGTGAGGTTCGACAGCGACGCCGAGTCCGA*206\**CAGA*GGAGCCCGGCGC*222\**GTGG*ATAGAGCAGGAGGGCCGGAGTAT

TGGGA*259\**CCGG*ACACACAGA*272\**TCTA*CAAGGCCCAGGCACA*292\**CACTG*ACCGA*302\**GACAG*CCTGCGGAACCTGCGCGGCTACTACAACCAGAGCCGTGAGTGACCCGGCCGGG

CGCAGGTCACGACTCCCCATCCCCCAGGTCTCCGAGTCTCCGGTCGCCCCGAGTCCTCCCTGAGCGGGGGGACTGGGCTGACGGGCCAGGGTCTCAC

CCAGGCGGCGGTTTACCCGGTTTCATTTTCAGTTGAGGCCAAAATCCCGGCCTGGGCGGGGTGTGCGGGGACCGGGGGCCAGGGTCTCAC

ACCCTC*362\*\*363 CAGAG GATG*369\*TAGGG*TGCGACGTGGGGCGGCCTCCTCCGG*412\**GGATG*418\*\*419*ACCAGAT*GGCT*TACATCGCCCTGAACGAGGACCTGCGCT

CCTGGACCGCCGCGGACGGCGCTCAGATCACCCAGCAAGCTGGAGCCGAGCCTACCTGGAGG*527\**GTC*GGGGAG*539\**AGG*GAGAGCCTACCTGGAGG*559\**GAGT*GCGTGGAG*571\**TCC*TCCGGAG

*583\*A*ACC*TGGAGAACGGGAAGGACAACCTGGAGCGCCGTGTACCAGGGCAGTGGGGAGCCTTCCC*CATC*CAT*AGCA*GGG*GGATGG*CCCTCCC

```
GAACACCCCCGAGCAEGTTCTTGTGGCAGCTTAAGTTTGAATGTCATTTCTTCAATGGGACGGAGGGTTGCTGCGAAAGATGCATCTATAACCAAGAGGAGTCGGTGC
                   *125                                                                       196**197
         227*                 *261
GCTTCGACAGCGGACGTGGGGCCGGTGACGGAGCTGGGCCGGTGAGCCTGATGCGAGTACTGGAACAGCCAGAAGGACGTCCTGGAGGCGAGCGCCGGGTGGACAC
                    AGTA              GAGT             286*                  299*         *308
         341*
CTACTGCAGACACAACTACCGGGTTGAGTGAGCTTTCAGAGTAGAGCTGGCGAGGTGAGCGCCGGGGGCCTGAGTCCCTGTGAGCGGAGAA
                    *345
```

FIGURE 5

SEQUENCE LISTING

<160> NUMBER OF SEQ ID NOS: 243

<210> SEQ ID NO 1
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 1
tgctcgcccc caggctccca                                              20

<210> SEQ ID NO 2
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 2
tgctcgcccc caggctctca                                              20

<210> SEQ ID NO 3
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 3
aggctcccac tccatgagct                                              20

<210> SEQ ID NO 4
<211> LENGTH: 20
<212> TYPE: DNA
<213> ORGANISM: Artificial
<220> FEATURE:
<221> NAME/KEY: Source

```
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 4
aggctcccam tccatgaggt                                                  20

<210> SEQ ID NO 5
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 5
aggctctcas tccatgaggt                                                  20

<210> SEQ ID NO 6
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 6
ccactccatg aggtatttca                                                  20

<210> SEQ ID NO 7
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group
```

```
<400> SEQUENCE: 7
ccactccatg aggtatttct                                           20

<210> SEQ ID NO 8
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 8
gcgatgaagc ggggctcctc                                           20

<210> SEQ ID NO 9
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 9
gcgatgaagc ggggctctcc                                           20

<210> SEQ ID NO 10
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
```

```
<223> OTHER INFORMATION: phosphorothioate group

<400> SEQUENCE: 10
gcgatgaagc ggggcttccc                                                    20

<210> SEQ ID NO 11
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 11
gmgatgaagc ggggctcccc                                                    20

<210> SEQ ID NO 12
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 12
ctsgtcccaa tactccggac                                                    20

<210> SEQ ID NO 13
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
```

-continued

```
<222> LOCATION: (20)..(20)
<223> OTHER INFORMATION: phosphorothioate group

<400> SEQUENCE: 13
cycgtcccaa tactccggac                                              20

<210> SEQ ID NO 14
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 14
ctcgtcccaa tactccggct                                              20

<210> SEQ ID NO 15
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 15
ctsgtcccaa tactcaggcc                                              20

<210> SEQ ID NO 16
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
```

```
<221> NAME/KEY: modified_base
<222> LOCATION: (20)..(20)
<223> OTHER INFORMATION: phosphorothioate group

<400> SEQUENCE: 16
cyggtcccaa tactccggcc                                          20

<210> SEQ ID NO 17
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 17
cmggtcccaa tactccggcc                                          20

<210> SEQ ID NO 18
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 18
cycgtcccaa tactccggcc                                          20

<210> SEQ ID NO 19
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group
```

<400> SEQUENCE: 19
cttcatattc cgtgtctcct                                                      20

<210> SEQ ID NO 20
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 20
cttcacwttc cgtgtctcct                                                      20

<210> SEQ ID NO 21
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 21
cttcacatkc cgtgtctgca                                                      20

<210> SEQ ID NO 22
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 22
cttcactttc cgtgtgttcc                                                      20

<210> SEQ ID NO 23
<211> LENGTH: 20
<212> TYPE: DNA
<213> ORGANISM: Artificial
<220> FEATURE:

```
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 23
cytcacattc cgtgtgttcc                                              20

<210> SEQ ID NO 24
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 24
cttcacrttc cgtgtctccc                                              20

<210> SEQ ID NO 25
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 25
cttcasttgc cgtgtctccc                                              20

<210> SEQ ID NO 26
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
```

-continued

<223> OTHER INFORMATION: phosphorothioate group

<400> SEQUENCE: 26
cttcagttkc cgtgtctccc                                                    20

<210> SEQ ID NO 27
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 27
attgggaccg gaacacacgg                                                    20

<210> SEQ ID NO 28
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 28
attgggacct gcagacacgg                                                    20

<210> SEQ ID NO 29
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 29
attgggacsa ggagacacgg                                                    20

<210> SEQ ID NO 30
<211> LENGTH: 20
<212> TYPE: DNA
<213> ORGANISM: Artificial

```
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 30
attgggacsg ggagacacgg                                                20

<210> SEQ ID NO 31
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 31
attgggacsa ggagacaggg                                                20

<210> SEQ ID NO 32
<211> LENGTH: 18
<212> TYPE: DNA
<213> ORGANISM: Artificial
<220> FEATURE:
<221> NAME/KEY: Source
<222> LOCATION: (1)..(18)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group

<400> SEQUENCE: 32
ctgtgagtgg gccttcat                                                  18

<210> SEQ ID NO 33
<211> LENGTH: 18
<212> TYPE: DNA
<213> ORGANISM: Artificial
<220> FEATURE:
<221> NAME/KEY: Source
<222> LOCATION: (1)..(18)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
```

-continued

```
<222> LOCATION: (18)..(18)
<223> OTHER INFORMATION: phosphorothioate group

<400> SEQUENCE: 33
ctgtgactgg gccytcac                                                    18

<210> SEQ ID NO 34
<211> LENGTH: 18
<212> TYPE: DNA
<213> ORGANISM: Artificial
<220> FEATURE:
<221> NAME/KEY: Source
<222> LOCATION: (1)..(18)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group

<400> SEQUENCE: 34
ctgtgagtgg sccttcac                                                    18

<210> SEQ ID NO 35
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 35
acacggaatg tgargggcca                                                  20

<210> SEQ ID NO 36
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 36
acasggaaag tgaaggccca                                                  20

<210> SEQ ID NO 37
<211> LENGTH: 20
<212> TYPE: DNA
```

-continued

```
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 37
acacggcawg tgaaggccca                                              20

<210> SEQ ID NO 38
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 38
acacggaacg tgaaggccca                                              20

<210> SEQ ID NO 39
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 39
acacggaatr tgaaggccca                                              20

<210> SEQ ID NO 40
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
```

```
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 40
tgaaggccca ctcacagagt                                               20

<210> SEQ ID NO 41
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 41
tgaaggccca ctcacaggct                                               20

<210> SEQ ID NO 42
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 42
tgaaggscca ctcacagatt                                               20

<210> SEQ ID NO 43
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
```

```
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 43
tgarggccca gtcacagact                                        20

<210> SEQ ID NO 44
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 44
tgaaggccca stcacagact                                        20

<210> SEQ ID NO 45
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 45
tcacaccatc cagataatgc                                        20

<210> SEQ ID NO 46
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
```

-continued

```
<223> OTHER INFORMATION: phosphorothioate group

<400> SEQUENCE: 46
tcacaccatc cagmtaatgt                                              20

<210> SEQ ID NO 47
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 47
tcacaccstc cagaggatgt                                              20

<210> SEQ ID NO 48
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 48
tcacaccvtc cagatgatgt                                              20

<210> SEQ ID NO 49
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 49
gctggtaccc gcggaggag                                               19
```

```
<210> SEQ ID NO 50
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 50
gccggtaccc gcggagtaa                                                19

<210> SEQ ID NO 51
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 51
ggtggtaccc gygcaggaa                                                19

<210> SEQ ID NO 52
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 52
ggtggtaccc gcagaggaa                                                19
```

```
<210> SEQ ID NO 53
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 53
gttcataccc gcggaggaa                                                    19

<210> SEQ ID NO 54
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 54
gstggtaccc gcggaggaa                                                    19

<210> SEQ ID NO 55
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 55
gccggtaccc gcggaggaa                                                    19
```

```
<210> SEQ ID NO 56
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 56
cgcttcctcc gcgggtatga                                              20

<210> SEQ ID NO 57
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 57
cgcttcctct gcgggtacca                                              20

<210> SEQ ID NO 58
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 58
cgcttcctgc gcgggtacca                                              20

<210> SEQ ID NO 59
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
```

```
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 59
cgcttcctcc acgggtacca                                          20

<210> SEQ ID NO 60
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 60
cgmttcctcc gcgggtacca                                          20

<210> SEQ ID NO 61
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 61
cgcctcctcc gcgggtacca                                          20

<210> SEQ ID NO 62
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 62
```
cacttcctcc gcgggtaccg                                              20

<210> SEQ ID NO 63
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 63
cgcttmctcc gcgggtaccg                                              20

<210> SEQ ID NO 64
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 64
gtccaagagc gcaggtcttc                                              20

<210> SEQ ID NO 65
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 65
gtccaagagc gcaggtcctc                                              20

<210> SEQ ID NO 66
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:

```
                        primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 66
gtccaggagc tcaggtcctc                                              20

<210> SEQ ID NO 67
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
        primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 67
ggccgyctcc cacttgtgct                                              20

<210> SEQ ID NO 68
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
        primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 68
ggcygcctcc cacttgcgct                                              20

<210> SEQ ID NO 69
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
        primer"
<220> FEATURE:
<221> NAME/KEY: modified_base
```

```
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 69
cggagtctcc cacttgcgct                                                    20

<210> SEQ ID NO 70
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 70
ggccgcctcc cacttgcgcc                                                    20

<210> SEQ ID NO 71
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 71
agtgggagac tccgcccatg                                                    20

<210> SEQ ID NO 72
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
```

```
<221> NAME/KEY: modified_base
<222> LOCATION: (20)..(20)
<223> OTHER INFORMATION: phosphorothioate group

<400> SEQUENCE: 72
caagtgggag gcggyccatg                                              20

<210> SEQ ID NO 73
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 73
caagtgggag rcggcccatg                                              20

<210> SEQ ID NO 74
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 74
caagtgggag gcggcccttg                                              20

<210> SEQ ID NO 75
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 75
caagtgggag gcggcccgtt                                              20

<210> SEQ ID NO 76
<211> LENGTH: 20
```

```
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 76
caagtgggag gcggcccgtc                                                    20

<210> SEQ ID NO 77
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 77
caagtgggag gcggccmgtg                                                    20

<210> SEQ ID NO 78
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 78
caagtgggag gcrgcccgtg                                                    20

<210> SEQ ID NO 79
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
```

```
<220> FEATURE:
<221> NAME/KEY: modified_base
<222> LOCATION: (19)..(19)
<223> OTHER INFORMATION: phosphorothioate group

<400> SEQUENCE: 79
gcccrtgagg cggagcagc                                                        19

<210> SEQ ID NO 80
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 80
gyccatgcgg cggagcagc                                                        19

<210> SEQ ID NO 81
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 81
gcccgtcggg cggagcagc                                                        19

<210> SEQ ID NO 82
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 82
gcccatgtgg cggagcagc                                                        19

<210> SEQ ID NO 83
```

```
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 83
gtccatgcgg cggagcagt                                              19

<210> SEQ ID NO 84
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 84
gcccgtyggg cggagcagt                                              19

<210> SEQ ID NO 85
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 85
gcccatgagg cggagcagt                                              19

<210> SEQ ID NO 86
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
```

-continued

<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 86
gcccwtgtgg cggagcagt                                                19

<210> SEQ ID NO 87
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 87
gccmgtgtgg cggagcagt                                                19

<210> SEQ ID NO 88
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 88
gcggagccac tccacgcact                                               20

<210> SEQ ID NO 89
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 89
gcggagcccg tccacgcact                                               20

```
<210> SEQ ID NO 90
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 90
gcggagccac tccacgcaca                                              20

<210> SEQ ID NO 91
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 91
gcggagcccg tccactcacg                                              20

<210> SEQ ID NO 92
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 92
gcggagccag tccacgcacg                                              20

<210> SEQ ID NO 93
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
```

```
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 93
gcggagccmg tccacgcacg                                               20

<210> SEQ ID NO 94
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 94
gcggagccac tccacgcacc                                               20

<210> SEQ ID NO 95
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 95
gcggagcccg tccacgcacc                                               20

<210> SEQ ID NO 96
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group
```

<400> SEQUENCE: 96
tggagggcck gtgcgtggag 20

<210> SEQ ID NO 97
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 97
tggagggyga gtgcgtggag 20

<210> SEQ ID NO 98
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 98
tgsagggccg gtgcgtggag 20

<210> SEQ ID NO 99
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

```
<400> SEQUENCE: 99
tggatgscac gtgcgtggag                                               20

<210> SEQ ID NO 100
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 100
tggagggcac stgcgtggag                                               20

<210> SEQ ID NO 101
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 101
tggagggcac gtgmgtggac                                               20

<210> SEQ ID NO 102
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
```

<223> OTHER INFORMATION: phosphorothioate group

<400> SEQUENCE: 102
tggagggcyg gtgcgtggac                                              20

<210> SEQ ID NO 103
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 103
cccactccat gaggcatttc                                              20

<210> SEQ ID NO 104
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 104
cccactycat gaggtatttc                                              20

<210> SEQ ID NO 105
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base

```
<222> LOCATION: (20)..(20)
<223> OTHER INFORMATION: phosphorothioate group

<400> SEQUENCE: 105
cgacgccgcg agtcmgagga                                              20

<210> SEQ ID NO 106
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 106
cgacgccacg agtccgagga                                              20

<210> SEQ ID NO 107
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 107
cgacgccgcg agtccragag                                              20

<210> SEQ ID NO 108
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
```

```
<221> NAME/KEY: modified_base
<222> LOCATION: (20)..(20)
<223> OTHER INFORMATION: phosphorothioate group

<400> SEQUENCE: 108
cgacgccrcg agtccgagag                                              20

<210> SEQ ID NO 109
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 109
gcccctcctg ctccaccca                                               19

<210> SEQ ID NO 110
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 110
gcccctcytg ctctatcca                                               19

<210> SEQ ID NO 111
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 111
ggccggagta ttgggacggg                                              20
```

<210> SEQ ID NO 112
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 112
ggccggagta ttgggacgag                                          20

<210> SEQ ID NO 113
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 113
ggccggagta ttgggacccg                                          20

<210> SEQ ID NO 114
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 114

-continued ggccggagta ttgggatcgg                                             20

<210> SEQ ID NO 115
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 115
ggccggagtt tgggaccgg                                              20

<210> SEQ ID NO 116
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 116
ggccggagca ttgggaccgg                                             20

<210> SEQ ID NO 117
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 117
ggccgggata ttgggaccgg					20

<210> SEQ ID NO 118
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 118
ggccrgaata ttgggaccgg					20

<210> SEQ ID NO 119
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 119
ggcgggmgta ttgggaccgg					20

<210> SEQ ID NO 120
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

```
<400> SEQUENCE: 120
ggccttagta ttgggaccgg                                                20

<210> SEQ ID NO 121
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 121
ggacsgggag acacggaaca                                                20

<210> SEQ ID NO 122
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 122
ggacgrggag acacggaaca                                                20

<210> SEQ ID NO 123
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 123
ggaccggaac acacagaact                                                20

<210> SEQ ID NO 124
<211> LENGTH: 20
<212> TYPE: DNA
<213> ORGANISM: Artificial
<220> FEATURE:
<221> NAME/KEY: Source
```

```
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 124
ggaccggaac acacagacct                                                   20

<210> SEQ ID NO 125
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 125
ggaccgggag acacagaagt                                                   20

<210> SEQ ID NO 126
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 126
ggaccgggag atacagatct                                                   20

<210> SEQ ID NO 127
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group
```

<400> SEQUENCE: 127
ggaccgggas acacagatct					20

<210> SEQ ID NO 128
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 128
ggaccgggac acacagatct					20

<210> SEQ ID NO 129
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 129
ggaccsggag acacagatct					20

<210> SEQ ID NO 130
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 130
caagaccaac acacaggct					19

<210> SEQ ID NO 131

```
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 131
caagscccag gcacaggct                                                19

<210> SEQ ID NO 132
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 132
caagaccaac acacggact                                                19

<210> SEQ ID NO 133
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 133
gaaggcctcc gcgcagact                                                19
```

```
<210> SEQ ID NO 134
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 134
caaggccmag gcacagact                                              19

<210> SEQ ID NO 135
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 135
caagsgccag gcacagact                                              19

<210> SEQ ID NO 136
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 136
gaagaccaac acacagact                                              19
```

```
<210> SEQ ID NO 137
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 137
gcacagactg accgagtgg                                              19

<210> SEQ ID NO 138
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 138
acacagactt acagagaga                                              19

<210> SEQ ID NO 139
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 139
acacagactt accgagagg                                              19
```

```
<210> SEQ ID NO 140
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 140
rcacagactg accgagagg                                               19

<210> SEQ ID NO 141
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 141
gcacagactg gccgagtga                                               19

<210> SEQ ID NO 142
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 142
```
acacagactt accgagtga                                                          19

<210> SEQ ID NO 143
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 143
rcacagactg accgagtga                                                          19

<210> SEQ ID NO 144
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 144
acacaggctg accgagaga                                                          19

<210> SEQ ID NO 145
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 145
rcacagactg accgagaga                                                19

<210> SEQ ID NO 146
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 146
gcrcagactt accgagaga                                                19

<210> SEQ ID NO 147
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (17)..(17)
<223> OTHER INFORMATION: phosphorothioate group
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 147
acacrgactt accgagaga                                                19

<210> SEQ ID NO 148
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

```
<400> SEQUENCE: 148
cgggtctcac accctccaca                                               20

<210> SEQ ID NO 149
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 149
cgggtctcac aycatccaga                                               20

<210> SEQ ID NO 150
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 150
cggktctcac accctccaga                                               20

<210> SEQ ID NO 151
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group
```

<400> SEQUENCE: 151
cgggtctcac acttggcaga                                                        20

<210> SEQ ID NO 152
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 152
cgggtctcac atcatccagg                                                        20

<210> SEQ ID NO 153
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 153
cgggtctcac accctccagt                                                        20

<210> SEQ ID NO 154
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 154
cccasgtcgc agccgtacat                                              20

<210> SEQ ID NO 155
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 155
cccabgtcgc agccatacat                                              20

<210> SEQ ID NO 156
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 156
cccasgtcgc agccaaacat                                              20

<210> SEQ ID NO 157
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 157
cccacgtcgc agccagacat                                              20

<210> SEQ ID NO 158
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:

-continued

```
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 158
cccacgtcgc agccgcacat                                              20

<210> SEQ ID NO 159
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 159
cccacgtcgc agccttacat                                              20

<210> SEQ ID NO 160
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 160
cccacgtcgc agccgtacgt                                              20

<210> SEQ ID NO 161
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 161
```

-continued tccggcccca kgtcgcagcc				20

<210> SEQ ID NO 162
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 162
tcgggcccca sgtcgcagcc				20

<210> SEQ ID NO 163
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 163
ggcgcctcct ccgcgggtac				20

<210> SEQ ID NO 164
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 164
ggcgcctcct ccscgggcat				20

```
<210> SEQ ID NO 165
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 165
ggcgcytcct ccgcgggcat                                              20

<210> SEQ ID NO 166
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 166
ggcgtctcct ccgcggttat                                              20

<210> SEQ ID NO 167
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 167
ggcgcctcct ccgcgggtat                                              20
```

```
<210> SEQ ID NO 168
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 168
tcctccgcgg gtatgaacag                                           20

<210> SEQ ID NO 169
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 169
tcctccacgg gtaccaccag                                           20

<210> SEQ ID NO 170
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 170
```

-continued

```
tcctgcgcgg gtaccaccag                                           20
```

<210> SEQ ID NO 171
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 171

```
tcctccgcgg gtaccaccag                                           20
```

<210> SEQ ID NO 172
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 172

```
tcctctgcgg gtaccaccag                                           20
```

<210> SEQ ID NO 173
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 173
tcctccgcgg gtaccagcag                                              20

<210> SEQ ID NO 174
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 174
tmctccgcgg gtaccggcag                                              20

<210> SEQ ID NO 175
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 175
tcctccgcgg gtaccagcgg                                              20

<210> SEQ ID NO 176
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

```
<400> SEQUENCE: 176
aatccttgcc gtcgtaggct                                              20

<210> SEQ ID NO 177
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 177
aatccttgcc gtcgtaggca                                              20

<210> SEQ ID NO 178
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 178
aattcttgcc gtcgtaggcg                                              20

<210> SEQ ID NO 179
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group
```

<400> SEQUENCE: 179
aatctttgcc gtcgtaggcg                                                                          20

<210> SEQ ID NO 180
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 180
aatccttgcc gtcgyaggcg                                                                          20

<210> SEQ ID NO 181
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 181
tcmttcaggg cgatgtaatc                                                                          20

<210> SEQ ID NO 182
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 182
tcgttcaggg cgatgtaatt                                                                          20

<210> SEQ ID NO 183

-continued

```
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 183
caagtgggag gcggcccttg                                              20

<210> SEQ ID NO 184
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 184
caagtkggag gcggcccgtg                                              20

<210> SEQ ID NO 185
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 185
ggcccgtgyg gcggagcagc                                              20

<210> SEQ ID NO 186
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
```

```
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 186
ggcccgtgtc gcggagcagg                                               20

<210> SEQ ID NO 187
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 187
ggcccgtgwg gcggagcagg                                               20

<210> SEQ ID NO 188
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 188
ggcccgtgag gcggagcagt                                               20

<210> SEQ ID NO 189
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 189
gcggagcgac tccacgcact                                               20
```

```
<210> SEQ ID NO 190
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 190
gcggagccac tccacgcact                                                   20

<210> SEQ ID NO 191
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 191
gcggagccaa tccacgcact                                                   20

<210> SEQ ID NO 192
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 192
gcggagccac tccacgcacg                                                   20

<210> SEQ ID NO 193
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
```

```
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 193
gcggagcgac tccrcgcaca                                                20

<210> SEQ ID NO 194
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 194
gcggagcsac tccacgcaca                                                20

<210> SEQ ID NO 195
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 195
gcggagcccg tccacgcaca                                                20

<210> SEQ ID NO 196
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 196
ctccaggtay ctgcggagcg                                                20
```

-continued

```
<210> SEQ ID NO 197
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 197
ctccaggtrt ctgcggagcc                                           20

<210> SEQ ID NO 198
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 198
acctggagaa cgggaagga                                            19

<210> SEQ ID NO 199
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 199
cattgaagaa atgacactcc                                           20

<210> SEQ ID NO 200
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
```

```
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 200
cgttgaagaa atgacactta                                              20

<210> SEQ ID NO 201
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 201
cattgaagaa atgacattca                                              20

<210> SEQ ID NO 202
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 202
cattgaagaa wtaacactca                                              20

<210> SEQ ID NO 203
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 203
crttgaagaa atgacactca                                              20
```

<210> SEQ ID NO 204
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 204
catctataac caagaggaa                                                  19

<210> SEQ ID NO 205
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 205
cttctatcac caagargag                                                  19

<210> SEQ ID NO 206
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence: primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 206
cttctataat cargaggag                                                  19

<210> SEQ ID NO 207
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence: primer"

```
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 207
cgtccataac caagaggag                                              19

<210> SEQ ID NO 208
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 208
catctataac caagaggag                                              19

<210> SEQ ID NO 209
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 209
cttccataac crggaggag                                              19

<210> SEQ ID NO 210
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 210
```
cttcgataac caggaggag                                                19

<210> SEQ ID NO 211
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 211
cttctataac ctggaggag                                                19

<210> SEQ ID NO 212
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 212
cgtcgctgtc gaagcgcagg                                               20

<210> SEQ ID NO 213
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 213
cgtcgctgtc gtagcgcgcg                                               20

<210> SEQ ID NO 214
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:

```
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 214
cgtcgctgtc gaagcgcaag                                            20

<210> SEQ ID NO 215
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 215
cgtcgctgtc gaagygcacg                                            20

<210> SEQ ID NO 216
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 216
cgtcgctgtc gaascgcacg                                            20

<210> SEQ ID NO 217
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 217
```
cgacagcgac gtgggggact                                        20

<210> SEQ ID NO 218
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 218
cgacagcgac gtgvgggagt                                        20

<210> SEQ ID NO 219
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 219
ttctggctgt tccagtactg                                        20

<210> SEQ ID NO 220
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 220
ttctggctgt tccagtaccc                                        20

<210> SEQ ID NO 221
<211> LENGTH: 20
<212> TYPE: DNA
<213> ORGANISM: Artificial
<220> FEATURE:
<221> NAME/KEY: Source
<222> LOCATION: (1)..(20)

```
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 221
ttctggctgt tccagtagtc                                                   20

<210> SEQ ID NO 222
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 222
ttctggctgt tccagtrctc                                                   20

<210> SEQ ID NO 223
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 223
ttcyggctgt tccaggactc                                                   20

<210> SEQ ID NO 224
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group
```

```
<400> SEQUENCE: 224
ctggaacagc cagaagaac                                               19

<210> SEQ ID NO 225
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 225
ctggaacagc crgaaggac                                               19

<210> SEQ ID NO 226
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 226
gaaggachtc ctggagcagg                                              20

<210> SEQ ID NO 227
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 227
gaaggacatc ctgggagaca                                              20

<210> SEQ ID NO 228
<211> LENGTH: 20
<212> TYPE: DNA
<213> ORGANISM: Artificial
<220> FEATURE:
<221> NAME/KEY: Source
```

```
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 228
gaaggacatc ctggargaca                                                    20

<210> SEQ ID NO 229
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 229
gaaggacytc ctggaagaca                                                    20

<210> SEQ ID NO 230
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 230
gaaggacatc ctggagcaga                                                    20

<210> SEQ ID NO 231
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group
```

-continued

<400> SEQUENCE: 231
gaaggachtc ctggagcgga                                           20

<210> SEQ ID NO 232
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 232
gaaggachtc ctggaagacg                                           20

<210> SEQ ID NO 233
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 233
gtctgcaata ggtgtccacg                                           20

<210> SEQ ID NO 234
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 234
gtctgcarta ggcgtccacc                                           20

<210> SEQ ID NO 235
<211> LENGTH: 20
<212> TYPE: DNA
<213> ORGANISM: Artificial
<220> FEATURE:

```
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 235
gtctgcagta attgtccacc                                              20

<210> SEQ ID NO 236
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 236
gtctgcacac ggtgtccacc                                              20

<210> SEQ ID NO 237
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 237
gtctgcagta ggtgtccacc                                              20

<210> SEQ ID NO 238
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
```

<223> OTHER INFORMATION: phosphorothioate group

<400> SEQUENCE: 238
gtctgcaata ggtgtccacc                                               20

<210> SEQ ID NO 239
<211> LENGTH: 19
<212> TYPE: DNA
<213> ORGANISM: Artificial
<220> FEATURE:
<221> NAME/KEY: Source
<222> LOCATION: (1)..(19)
<223> OTHER INFORMATION: /note="Description of artificial sequence:
      primer"
<220> FEATURE:
<221> NAME/KEY: modified_base
<222> LOCATION: (18)..(18)
<223> OTHER INFORMATION: phosphorothioate group
<220> FEATURE:
<221> NAME/KEY: modified_base
<222> LOCATION: (19)..(19)
<223> OTHER INFORMATION: phosphorothioate group

<400> SEQUENCE: 239
tgcagacaca actacsggg                                                19

<210> SEQ ID NO 240
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 240
cgctgcactg tgaatctctc                                               20

<210> SEQ ID NO 241
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 241
ctctgcactg tgaagctctc                                               20

<210> SEQ ID NO 242
<211> LENGTH: 20
<212> TYPE: DNA
<213> ORGANISM: Artificial

-continued

```
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 242
cgctgcacyg tgaagctctc                                              20

<210> SEQ ID NO 243
<211> LENGTH: 20
<212> TYPE: DNA
<213> ORGANISM: Artificial
<220> FEATURE:
<221> NAME/KEY: Source
<222> LOCATION: (1)..(20)
<223> OTHER INFORMATION: /note="Description of artificial sequence:
      primer"
<220> FEATURE:
<221> NAME/KEY: modified_base
<222> LOCATION: (19)..(19)
<223> OTHER INFORMATION: phosphorothioate group
<220> FEATURE:
<221> NAME/KEY: modified_base
<222> LOCATION: (20)..(20)
<223> OTHER INFORMATION: phosphorothioate group

<400> SEQUENCE: 243
gcggagccac tccacgcagg                                              20
```

METHOD FOR HLA TYPING

The present invention relates to a method for HLA typing by the unambiguous determination of short DNA sequence elements (2-6 bases) at a given position simultaneously on both parental alleles at a selected number of positions in HLA genes, comprised of the steps for-each position of a) hybridising a combination of oligonucleotides (primers) complementary to all known sequence variants to a DNA strand upstream of a given position; b) carrying out a primer extension reaction with at least one of the four dNTP substrates substituted by a terminating analog; c) analysing the products by mass spectrometry, with the resulting masses allowing unambiguous identification of the used primers and the added bases. This method is particularly well suited for DNA-based HLA typing and in combination with a suitable selection of sites tested, it is superior in ease of operation to conventional HLA typing methods.

The most important of the genome projects, the complete sequence of the human genome, is finished. This project reveals the complete sequence of the 3 billion bases and the relative positions of all estimated 30.000 genes in this genome. Having this sequence opens unlimited possibilities for the elucidation of gene function and interaction of different genes. In recent years a systematic effort (SNP consortium) has been underway to identify single nucleotide polymorphisms (SNPs) throughout the human genome and so far several million of these differences between different human beings have been identified (dbSNP contained 5.5 million SNPs in October 2003).

Matrix-assisted laser desorption/ionization time-of-flight mass spectrometry (MALDI) has revolutionized the mass spectrometric analysis of biomolecules (Karas, M. & Hillenkamp, F. Anal. Chem. 60, 2299-2301 (1988)). The field of DNA analysis by mass spectrometry was recently extensively reviewed by Tost and Gut (Mass Spectrometry Reviews, 21, 388-418 (2002)) and Sauer and Gut (Journal of Chromatography B, 782, 73-87, (2002)). MALDI has been applied to the analysis of DNA in variations that range from the analysis of PCR products to approaches using allele-specific termination to single nucleotide primer extension reactions and sequencing (Liu, Y-H., et al. *Rapid Commun. Mass Spectrom.* 9, 735-743 (1995); Ch'ang, L.-Y., et al. *Rapid Commun. Mass Spectrom.* 9, 772-774 (1995); Little, D. P., et al. *J. Mol. Med.* 75, 745-750 (1997); Haff, L. & Smimov, J. P. *Genome Res.* 7, 378-388 (1997), Fei, Z., Ono, T. & Smith, L. M. *Nucleic Acids Res.* 26, 28272828 (1998); Ross, P., Hall, L., Smirnov, 1. & Haff, L. *Nature Biotech.* 16, 1347-1351 (1998); Ross, P. L., Lee, K. & Bel grader, P. *Anal. Chem.* 69, 4197-4202 (1997); Griffin, T. J., Tang, W. & Smith, L. M. *Nature Biotech.* 15, 1368-1372 (1997); Koster, H., Higgins, G. S & Little, D. P. U.S. Pat. No. 6,043,031). These methods are used to genotype previously identified mutations, SNPs, or insertion/deletions (indels). Spin column purification and/or magnetic bead technology, reversed-phase purification, or ion-exchange resins are frequently applied prior to mass spectrometric analysis.

The GOOD assay (IG Gut et S. Beck: U.S. Pat. No. 6,268, 812; IG Gut et al: U.S. Pat. No. 6,503,710) is a method for SNP genotyping that uses MALDI mass spectrometry for detection (Sauer et al. 28, e13 and e100 (2000>>. Allele-distinction is based on primer extension. In order to make products more amenable to MALDI analysis a substantial part of the primer is removed prior to mass spectrometric analysis. A further element that is included is charge tagging. This means that the final product is conditioned such that it carries either a single positive or a single negative charge. Generally this is achieved by alkylation of a phosphorothioate backbone and in some instances including a quaternary ammonium group to the penultimate base of the primer. The attachment of the quaternary ammonium group gives options for the design of multiplexes—individual SNPs can be moved up or down in the mass spectrum to achieve optimal resolution and separation.

The major histocompatibility complex (MHC) of humans is a cluster of genes on chromosome 6p21. It is of greatest importance as many diseases show association with genes in this region of the genome. All human leukocyte antigen (HLA) coding genes are found in the MHC. The HLA genes are highly variable and implicated in tissue transplantation, immunity and autoimmune disease such as diabetes, psoriasis, lupus, Crohn's disease, colitis, arthritis, and others. The HLA 30 class I genes are HLA-A, HLA-B, HLA-C, . . . . The HLA class II genes are HLADR, HLA-DQ, HLA-DP, . . . .

HLA typing methods differ dramatically in their approaches. Serological tests can be carried out but have only limited resolution. In the last 15 years the DNA sequence of the MHC has been extensively studied and high resolution typing now makes use of a wealth of DNA sequence information. Methods for DNA based HLA typing range from SSA (sequence specific amplification) where combinations of primers that are specific for different alleles are used to carry out PCR (U.S. Pat. No. 5,545,526). Primers are combined in a way that the sizing of the PCR products allows unambiguous assignment of present base combinations. Multiple combinations are used to identify HLA types. The procedure works its way through a tree of combinations starting with a grouping into rough classes from where on further tests are carried out with specific reagents to subdivide in a class. This method is also known as SSP (sequence specific primers). An alternative method is termed SSOP (sequence specific oligonucleotide probes; U.S. Pat. No. 6,503,707). Here a locus specific PCR is carried out followed by hybridisation with sequence specific oligonucleotide probes. As sequencing technology (and in particular the software for sequence calling) has dramatically improved over the last decade it now is also possible to gain a good degree of identification of HLA types by sequencing (WO 98/35059). Effectively a locus-specific PCR product is sequenced. Problems that arise here are that heterozygous individuals occasionally give rise to ambiguous haplotype calls that can not be resolved (Robinson, J.; Waller, M. J.; Marsh, St. G. E.: "Exon Identities and Ambiguous Typing Combinations"; IMGT/HLA Database; October 2003). The inclusion of allele-specific PCR helps achieve certainty. Resolution requires multiple products per locus to be generated and sequenced. However, as sequencing results can be very convoluted the interpretation in absence of allele-specific PCR can be cumbersome. All together the sequence-based typing requires many iterations in application. Reference strand mediated conformation analysis (RSCA) is a method used to study samples that potentially have a previously unknown sequence in their HLA (Correl et al., Tissue Antigens 56, 82-86, 2000). For a recent review for the reasoning of HLA typing as well as methodological advances see Petersdorf et al. (Tissue Antigens, 61, 1-11, 2003).

The inventors have thus set themselves the task of providing an easy method for the simultaneous capture of all parental mini-haplotypes in highly polymorphic regions of genomes. The procedure has to be executable on a cost-effective genotyping platform. The method should be particularly applicable for HLA typing. It is an aim to resolve frequent and rare HLA alleles as well as possible.

The object of the present invention is a method for HLA typing by the unambiguous determination of short DNA sequence elements (2-6 bases) simultaneously on both parental alleles at a selected number of positions in HLA genes, comprised of the steps for each position of a) hybridising a combination of oligonucleotides (primer pool) complementary to all known sequence variants to a DNA strand upstream of a given position; b) carrying out a primer extension reaction with at least one of the four dNTP substrates substituted by a terminating analog; c) analysing the products by mass spectrometry, with the resulting masses allowing unambiguous identification of the used primers and the added bases.

In the present invention:

"HLA" means the human leukocyte antigen locus on chromosome 6p21, consisting of HLA genes (HLA-A, HLA-B, HLA-C, HLA-DRB1, . . . ) that are used to determine the degree of matching, for example, between a recipient and a donor of a tissue graft.

"HLA typing" means the identification of a known HLA allele of a given locus (HLA-A, HLA-B, HLA-C, HLA-DRB1, . . . ).

"HLA allele" means a nucleotide sequence within a locus on one of the two parental chromosomes.

"HLA-A" means the DNA sequence of exons 2 and 3 of the HLA-A gene.

"HLA-B" means the DNA sequence of exons 2 and 3 of the HLA-B gene.

"HLA-DRB1" means the DNA sequence of exon 2 of the HLA-DRB1 gene.

"Polymorphism" means individual positions in a DNA sequence that exist in different variants.

"Haplotype" means the DNA sequence of one of the two alleles in a give region of the genome.'

"Mini-haplotype" means 2-6 contiguous bases on one parental allele.

"Primer pools" or "pools of primers" means sets of primers that are used in one primer extension reaction. For each known HLA allele at least one primer is in the pool that is completely complementary in sequence. This assures perfect annealing. Mismatches that are more than 4 bases from the 3' end of the primer do not affect the results of the GOOD assay, as all of those bases are removed by 5' phosphodiesterase after the primer extension reaction. Primers of the pool containing mismatches in the last few bases are not extended by the DNA polymerase and thus not observable.

"MALDI mass spectrometer" means a mass spectrometer that uses matrix-assisted laser desorption/ionization for the volatilisation of a sample and time-of-flight analysis for mass separation.

"Subgroup" means alleles, which are identical after the mini-haplotyping of the first set of selected positions. For the high resolution typing we resolve subgroups generated with 10 mini-haplotyping reactions. The criteria for resolving subgroups are: a) they still contain alleles with different two-digit types, b) subgroups with more than four alleles, and c) subgroups with frequent alleles (see list below).

Here we show a methodology for the determination of sequence motifs of 2-6 bases in very polymorphic regions of genomes. In principle this methods equates to the determination of mini-haplotypes of 2-6 bases. The individual parental mini-haplotypes can be determined in one reaction without ambiguities. This methodology is applied to a chosen set of positions for HLA typing of HLA-A, 25 HLA-B, and HLA-DRB1. The sets disclosed here have different purposes. First sets of 19, 19, and 10 positions are suggested to distinguish a maximum of HLA alleles in HLA-A, HLA-B, and HLA-DRB1, respectively, with respect to differentiating alleles that are frequent in the general population from ones that are rare. The frequent alleles that were screened for are A*0101, A*0201, A*0301, A*2301, A*2402, A*2902, A*3001 and A*3002 for HLA-A, B*0702, B*0801, B*1302, B*1501, B*1801, B*3501, B*3503, B*4001, B*4402, B*4403, B*5101 and B*5701 for HLA-B, and DRB1*0101, DRB1*0301, DRB1*0401, DRB1*0701, DRB1*1101, DRB1*1104, DRB1*1302 and DRB1*1501 for HLA-DRB1. This set of markers provides unambiguous identification of frequent HLA alleles with 93.4-100% certainty in HLA-A, 97.6-100% in HLA-B, and 97.2-100% in HLA-DRB1.

A second set of 10 positions each in HLA-A, HLA-B, and HLA-DRB1, respectively are described that provide a maximum number of subgroups, that can then be further resolved by the addition of a set of subgroup specific positions. Again the ten positions in each locus were chosen on the basis of providing best distinction between the frequent HLA alleles listed above from the rest of the HLA alleles (rare). This resulted in groups containing 2-30 HLA alleles depending on the locus. Within each group a number of positions can be tested to provide resolution between the HLA alleles within the group. The number of positions that have to be additionally analysed range from 1-25 in order to achieve 4-digit resolution. With this technology HLA typing can be carried out at a substantially reduced cost with a proven high-throughput detection platform (MALDI mass spectrometry).

In a preferred embodiment of the method of the invention, the DNA strand of step a) is produced by a DNA replication procedure such as PCR or rolling circle replication.

A set of locus-specific PCR reactions for the selective amplification of each locus is described by the International Histocompatibility Working Group, Technical Manuals (www.ihwg.org/tmanual/Tmcontents.htm).

In a very preferred embodiment of the method of the invention, a combination of primers (pools of primers) contains slightly varying sequences so that all known sequences of the HLA alleles are accommodated by a perfectly matching primer. The pool of primers guarantees that at least one primer is perfectly matched. The hybridised oligonucleotides of the primer pool are extended onto a polymorphic position. A requirement is that the added base together with the base composition of the primer gives a unique mass. The detection of this mass in the mass spectrometric profile indicates the presence of a sequence containing both the complementary sequence of the primer and the added base. In order to make all primers of a primer pool distinguishable by mass it is possible to add different mass shifting agents to the primers. The easiest way to accomplish this is by using charge/mass tagging technology such as is used in the GOOD assay. The penultimate base from the 3' end of the primer is amino-modified and used to add tags via NHS-ester chemistry. The pools of primers of course contain primers that sometimes differ by as little as one base. Sequences identical in base content can still be distinguished by the suitable selection of mass tags. Also, we have found that a primer carrying a mismatch in the last eight bases from the 3'end even if it anneals is not extended by the polymerase and thus screened out. This might be due to insufficient hybridisation or a resistance of the DNA polymerase to attach or extend when a mismatch is present. We thus make use of two effects for our minihaplotyping: 1) allele-specific hybridisation and 2) allele-specific primer extension. Mismatches that are further than four bases away from the 3' end of the extension primer do not result in increased complexity of the mass spectra as they are removed in the 5' phosphodiesterase digestion step of the GOOD assay.

In a preferred embodiment of the method of the invention, mass shifting tags are added to the individual primers sequences of a primer pool to make them uniquely distinguishable once the terminating base is added.

In another preferred embodiment of the method of the invention, termination products for know alleles are generated. by extending the perfectly hybridized primer with a combination of dNTPs and ddNTPs or analogues thereof with a DNA polymerase to generate specific termination products to make them uniquely distinguishable by their mass.

In a preferred embodiment of the method of the invention, the GOOD assay is used. It typically applies single base primer extension, thus only the four terminating bases (ddNTPs) or synthetic analogues with the same qualities in terms of DNA polymerase tolerance are used for primer extension. α-S-ddNTPs are very suitable analogues.

In a preferred embodiment of the method of the invention, mass spectrometry, in particular MALDI or ESI mass spectrometry is used for analysis of the masses of products.

For HLA typing a set of said mini-haplotyping assays has to be carried out to achieve sufficient information content.

For HLA typing of HLA-A the preferred set of assays are those of positions 98, 414, 539, 282, 571, 368, 256, 292, 238, 270, 453, 527, 502, 81, 268, 559, 92, 123 and 396 (according to the numbering of the HLA-A gene starting at cDNA sequence position 1 of exon 1; see FIG. 1). This results in medium resolution HLA typing. The input criteria for the selection are the frequency of HLA alleles. Some HLA types are identified unambiguously.

For HLA typing of HLA-B accordingly the following positions are preferably analysed by mini-haplotyping assays to achieve medium resolution: 539, 419, 559, 412, 272, 362, 302, 363, 206, 369, 259, 97, 583, 292, 222, 527, 418, 435 and 571 (according to the numbering of the HLA-B gene starting at cDNA sequence position 1 of exon 1; see FIG. 2).

For HLA typing of HLA-DRB1 accordingly the following positions are preferably analysed by mini-haplotyping to achieve medium resolution: 125, 196, 197, 227, 261, 286, 299, 308, 341 and 345 (according to the numbering of the HLA-DRB1 gene starting at cDNA sequence position 1 of exon 1; see FIG. 3).

In a preferred embodiment for high resolution HLA typing of HLA-A positions 98, 414, 539, 282, 571, 368, 256, 292, 238 and 270 (according to the numbering of the HLA-A gene starting at cDNA sequence position 1 of exon 1; see FIG. 4) are used for mini-haplotyping to generate sub-groups (HLA-A_A, HLA-A_B, HLA-A_C, HLA-A_D, HLA-A_E, HLA-A_F, HLA-A_G, HLA-A_H, HLA-A_I, HLA-A_J, HLA-A_K, HLA-A_L, HLA-A_M, HLA-A_N, and HLA-A_O; see Table I). Positions 224, 268, 376, 502, 561 and 616 are preferably analysed to resolve subgroup HLA-A_A (sequences identical over exons 2 and 3 for alleles A*29010101 and A*29010102); positions 126 and 526 to resolve subgroup HLA-A_B; positions 81, 90, 92, 212, 214, 257, 265, 299, 302, 404, 420, 427, 453, 485, 489 and 502 to resolve subgroup HLA-A_C (sequences identical over exons 2 and 3 for alleles A*24020101, A*24020102L, A*240203, A*2409N and A*2411N); positions 160, 200, 362 and 524 to resolve subgroup HLA-A_D; positions 180, 299, 301, 302, 346, 418, 453, 517, 524, 526, 527, 557, 559 and 560 to resolve subgroup HLA-A_E; positions 299, 301, 302, 341 and 583 to resolve subgroup HLA-A_F; positions 127, 341, 399, 480, 502, 503, 524, 526, 527, 553, 559, 560 and 565 to resolve subgroup HLA-A_G; positions 228, 233, 463, 519, 530 and 583 to resolve subgroup HLA-A_H; positions 102, 275, 317, 362, 418, 419, 497, 524, 555, 595 and 618 to resolve subgroup HLA-A_I (sequences identical over exons 2 and 3 for alleles A*680102 and A*6811N); positions 92, 331, 453, 524, 559, 560 and 564 to resolve subgroup HLA-A_J; positions 78, 81, 123, 125, 142, 144, 194, 268, 294, 324, 355, 362, 396, 403, 419, 453, 456, 477, 493, 517, 524, 526, 527, 559 and 560 to resolve subgroup HLA-A_K (sequences identical over exons 2 and 3 for alleles A*02010101, A*02010102, A*020108, A*0209, A*0243N and A*0266); positions 113, 299, 301, 302, 308, 311, 523, 524 to resolve subgroup HLA-A_L; positions 171, 363, 498 and 559 to resolve subgroup HLA-A_M; positions 376, 426, 527, 555, 557 and 595 to resolve subgroup HLA-A_N; position 299 to resolve subgroup HLA-A O.

TABLE I

| Subgroups of HLA-A | Alleles of Subgroups | Positions to resolve Subgroups |
|---|---|---|
| HLA-A_A | A*29010101, A*29010102, A*290201, A*290202, A*2904, A*2906, A*2908N, A*2909 | 224, 268, 376, 502, 561, 616 |
| HLA-A_B | A*3002, A*3009, A*3012 | 126, 526 |
| HLA-A_C | A*24020101, A*24020102L, A*240202, A*240203, A*240204, A*2404, A*2405, A*2408, A*2409N, A*2411N, A*2420, A*2421, A*2425, A*2426, A*2427, A*2429, A*2432, A*2435, A*2436N, A*2437, A*2438, A*2439 | 81, 90, 92, 212, 214, 257, 265, 299, 302, 404, 420, 427, 453, 485, 485, 489, 502 |
| HLA-A_D | A*0206, A*0214, A*0221, A*0251, A*0257 | 160, 200, 362, 524 |
| HLA-A_E | A*250101, A*250102, A*2601, A*2604, A*2605, A*2609, A*2610, A*2611N, A*2612, A*2614, A*2615, A*2617, A*2618, A*6603 | 180, 299, 301, 302, 346, 418, 453, 517, 524, 526, 527, 557, 559, 560 |
| HLA-A_F | A*2502, A*2613, A*6601, A*6602, A*6604 | 299, 301, 302, 341, 583 |
| HLA-A_G | A*110101, A*110102, A*1102, A*1103, A*1104, A*1105, A*1107, A*1109, A*1112, A*1113, A*1114, A*1115 | 127, 341, 399, 480, 502, 503, 524, 526, 527, 553, 559, 560, 565 |
| HLA-A_H | A*3301, A*330301, A*330302, A*3304, A*3305, A*3306, A*3307 | 228, 233, 463, 519, 530, 583 |
| HLA-A_I | A*680101, A*680102, A*680103, A*6807, A*6811N, A*6812, A*6816, A*6817, A*6819, A*6821, A*6822, A*6823, A*6824 | 102, 275, 317, 362, 418, 419, 497, 524, 555, 595, 618 |
| HLA-A_J | A*2301, A*2303, A*2305, A*2306, A*2307N, A*2308N, A*2310, A*2413 | 92, 331, 453, 524, 556, 560, 564 |

TABLE I-continued

| Subgroups of HLA-A | Alleles of Subgroups | Positions to resolve Subgroups |
|---|---|---|
| HLA-A_K | A*02010101, A*02010102, A*020102, A*020103, A*020104, A*020105, A*020106, A*020107, A*020108, A*020109, A*0204, A*0209, A*0216, A*0224, A*0225, A*0226, A*0229, A*0230, A*0231, A*0232N, OA*0240, A*0242, A*0243N, A*0258, A*0259, A*0260, A*0264, A*0266, A*0267, A*0253N | 78, 81, 123, 125, 142, 144, 194, 268, 294, 324, 355, 362, 396, 403, 419, 453, 419, 453, 456, 477, 493, 517, 524, 526, 527, 559, 560 |
| HLA-A_L | A*3201, A*3203, A*3206, A*7401, A*7402, A*7403, A*7408, A*7409 | 113, 299, 301, 302, 308, 311, 523, 524 |
| HLA-A_M | A*010101, A*010102, A*0103, A*0104N, A*0108, A*0109 | 171, 363, 498, 559 |
| HLA-A_N | A*03010101, A*03010102, A*0303N, A*0304, A*0305, A*0306, A*0307, A*0311N | 376, 426, 527, 555, 557, 595 |
| HLA-A_O | A*2504, A*2608 | 299 |

In a preferred embodiment for high resolution, HLA typing of BLA-B positions 539, 419, 559, 412, 272, 362, 302, 363, 206 and 369 (according to the numbering of the HLA-B gene starting at cDNA sequence position 1 of exon 1; see FIG. 5) "are used for mini-haplotyping to generate sub-groups (HLA-B_A, HLA-B_B, HLA-B_C, HLA-B_D, HLA-B_E, HLA-B_F, HLA-B_G, HLA-B_H, HLA-B_I, HLA-B_J, HLA-B_K, HLA-B_L, HLA-B_M, HLA-B_N, HLA-B_O, HLA-B_P, HLA-B_Q, HLA-B_R, HLA-B_S, HLA-B_T, HLA-B_U, HLA-B_V, HLA-B_W, HLA-B_X, HLA-B_Y, HLA-B_Z, HLA-B_AA, HLA-B_AB and HLA-B_AC; see Table II).

Positions 259, 341 and 473 are preferably analyzed to resolve subgroup HLA-B_A (sequences identical over exons 2 and 3 for alleles B*0801 and B*0819N); positions 106, 144, 222, 259, 273, 311, 313, 418, 445, 493, 528 and 540 to resolve subgroup HLA-B_B (sequences identical over exons 2 and 3 for alleles B*44020101, B*44020102, B*4419N and B*4427); positions 319, 416, 545 and 572 to resolve subgroup HLA-B_C; positions 106, 131, 165, 215, 243, 277, 292, 322, 481, 582, 603 and 616 to resolve subgroup HLA-B_D; positions 106, 146, 165, 181, 238, 259, 263, 292, 328.1/329 (insert for B*1579N), 379, 435, 453, 463, 485, 526, 571, 572 and 583 to resolve subgroup HLA-B_E (sequences identical over exons 2 and 3 for alleles B*15010101 and B*15010102); positions 142, 171, 255, 257, 395, 430, 544, 566 and 572 to resolve subgroup HLA-B_F; positions 117, 247, 248, 277, 345, 418, 489 and 527 to resolve subgroup HLA-B_G (sequences identical over exons 2 and 3 for alleles B*270502, B*270504 and B*2713); positions 134, 141, 200, 213, 259, 304 and 527 to resolve subgroup HLA-B_H; positions 83, 141, 211, 222, 242, 322, 404, 414, 435, 463, 502, 527, 544, 571, 572 and 583 to resolve subgroup HLA-B_I (sequences identical over exons 2 and for alleles B*510101, B*510105, B*5111N, B*5130 and B*5132); positions 103, 142, 222, 243, 259, 292, 477, 486 and 499 to resolve subgroup HLA-B_J (sequences identical over exons 2 and 3 for alleles B*400101 and B*400102); positions 103, 259, 292, 295, 527 and 583 to resolve subgroup HLA-B_K (sequences identical over exons 2 and 3 for alleles B*180101 and B*1817N); positions 320 and 500 to resolve subgroup HLA-B_L; positions 311, 527 and 583 to 30 resolve subgroup HLA-B_M; positions 119, 292, 259, 319, 425, 527, 546 and 583 to resolve subgroup HLA-B_N (sequences identical over exons 2 and 3 for alleles B*350101, B*3540N and B*3542); positions 97, 142, 245 and 527 to resolve subgroup HLA-B_0; positions 97 and 175 to resolve subgroup HLA-B_P; positions

TABLE II

| Subgroups of HLA-A | Alleles of Subgroups | Positions to resolve Subgroups |
|---|---|---|
| HLA-B_A | B*0801, B*0808N, B*0810, B*0818, B*0819N | 259, 341, 473 |
| HLA-B_B | B*44020101, B*44020102S, B*440202, B*440203, B*4405, B*4411, B*4412, B*4419N, B*4422, B*4423N, B*4424, B*4425, B*4427, B*4433, B*4434, B*4435 | 106, 144, 222, 259, 273 311, 313, 418, 445, 493, 528, 540 |
| HLA-B_C | B*4415, B*4501, B*4503, B*4504, B*4505 | 319, 416, 545, 572 |
| HLA-B_D | B*070201, B*070202, B*070203, B*070204, B*0703, B*0716, B*0721, B*0722, B*0723, B*0729, B*0730, B*0733, B*0735 | 106, 131, 165, 215, 243, 277, 292, 322, 481, 582, 603, 616 |
| HLA-B_E | B*15010101, B*15010102, B*150102, B*150103, B*150104, B*1512, B*1514, B*1515, B*1519, B*1528, B*1533, B*1534, B*1538, B*1560, B*1570, B*1571, B*1575, B*1578, B*1579N, B*1581, B*1582 | 106, 146, 165, 181, 238, 259, 263, 292, 328.1/329, 379, 435, 453, 463, 485, 526, 571, 572, 583 |
| HLA-B_F | B*440301, B*4413, B*4426, B*4429, B*4430, B*4432, B*4436, B*4437, B*4438, B*4439 | 142, 171, 255, 257, •395, 430, 544, 566, 572 |
| HLA-B_G | B*2703, B*270502, B*270503, B*270504, B*270505, B*270506, B*2709, B*2710, B*2713, B*2716, B*2717 | 117, 247, 248, 277, 345, 418, 489, 527 |
| HLA-B_H | B*5107, B*520101, B*520102, B*520103, B*520104, B*5203, B*5204, B*5205 | 134, 141, 200, 213, 259, 304, 527 |

TABLE II-continued

| Subgroups of HLA-A | Alleles of Subgroups | Positions to resolve Subgroups |
|---|---|---|
| HLA-B_I | B*510101, B*510102, B*510103, B*510104, B*510105, B*510201, B*510202, B*5103, B*5109, B*5111N, B*5112, B*5114, B*5118, B*5119, B*5123, B*5124, B*5126, B*5127N, B*5128, B*5130, B*5132, B*5133 | 83, 141, 211, 222, 242, 322, 404, 414, 435, 463, 502, 527, 544, 571, 572, 583 |
| HLA-B_J | B*400101, B*400102, B*400103, B*4010, B*4011, B*401401, B*401402, B*401403, B*4022N, B*4025, B*4043 | 103, 142, 222, 243, 259, 292, 477, 486, 499 |
| HLA-B_K | B*180101, B*180102, B*1803, B*1804, B*1805, B*1811, B*1812, B*1815, B*1817N | 103, 259, 292, 295, 527, 583 |
| HLA-B_L | B*570101, B*5706, B*5708 | 320, 500 |
| HLA-B_M | B*3527, B*5301, B*5302, B*5306, B*5308 | 311, 527, 583 |
| HLA-B_N | B*350101, B*350102, B*3507, B*3510, B*3511, B*3521, B*3524, B*3529, B*3540N, B*3541, B*3542, B*5305 | 119, 292, 259, 319, 425, 527, 546, 583 |
| HLA-B_O | B*5501, B*5502, B*5505, B*5510, B*5516 | 97, 142, 245, 527 |
| HLA-B_P | B*5401, B*5402, B*5507 | 97, 175 |
| HLA-B_Q | B*3910, B*670101, B*670102 | 246, 277 |
| HLA-B_R | B*3803, B*390201, B*390202, B*3913, B*3923 | 246, 292, 311, 503 |
| HLA-B_S | B*3801, B*380201, B*380202, B*3804, B*3805, B*3809 | 103, 261, 309, 311, 474 |
| HLA-B_T | B*390101, B*390103, B*390104, B*3904, B*390S, B*3912, B*3922, B*3925N, B*3926 | 97, 103, 106, 243, 259, 292, 404, 524 |
| HLA-B_U | B*3503, B*3513, B*3536 | 259, 320 |
| HLA-B_V | B*0734, B*5504 | 106 |
| HLA-B_W | B*4047, B*4431 | 97 |
| HLA-B_X | B*4002, B*4027, B*4029, B*403S, B*4040, B*4045 | 97, 106, 257, 418, 463 |
| HLA-B_Y | B*400104, B*4004 | 106 |
| HLA-B_Z | B*4012, B*4046, B*4803 | 106, 144 |
| HLA-B_AA | B*2703, B*270502, B*270503, B*270504, B*270505, B*270506, B*2709, B*2710, B*2713, B*2716, B*2717 | 117, 247, 248, 283, 345, 418, 489, 527 |
| HLA-B_AB | B*1562, B*4802 | 106 |
| HLA-B_AC | B*1302, B*1308 | 548 |

246 and 277 to resolve subgroup HLA-B_Q; positions 246, 292, 311 and 503 to resolve subgroup HLA-B_R; positions 103, 261, 309, 311 and 474 to resolve subgroup HLA-B_S; positions 97, 103, 106, 243, 259, 292, 404 and 524 to resolve subgroup HLA-B_T (sequences identical over exons 2 and 3 for alleles B*390101 and B*390103); positions 259 and 320 to resolve subgroup HLA-B_U; position 106 to resolve HLA-B_V; positions 97 to resolve HLA-B_W; positions 97, 106, 257, 418 and 463 to resolve HLA-B_X; position 106 to resolve HLA-B_Y; positions 106 and 144 to resolve HLA-B_Z; positions 117, 247, 248, 283, 345, 418, 489, and 527 to resolve HLA-B_AA; positions 106 to resolve HLA-B_AB; positions 548 to resolve HLA-B_AC.

In a preferred embodiment, the method for HLA typing resolves groups A-P of HLA-DRB1.

For high resolution, HLA typing of HLA-DRB1 positions are: 125, 196, 197, 227, 261, 286, 299, 308, 341 and 345 (according to the numbering of the HLA-DRB1 gene starting at DNA sequence position 1 of exon 1; see FIG. 6) are used for mini-haplotyping to generate sub-groups (HLA-DRB1_A, HLA-DRB1_B, HLA-DRB1_C, HLA-DRB1_D, HLA-DRB1_E, HLA-DRB1_F, HLA-DRB1_G, HLA-DRB1_H, HLA-DRB1_J, HLA-DRB1_J, HLA-DRB1_K, HLA-DRB1_L, HLA-DRB1_M, HLA-DRB1_N, HLA-DRB1_O, HLA-DRB1_P; see Table III).

In a very preferred embodiment, positions 123, 174, 250, 278 and 317 are analysed to resolve subgroup HLA-DRB1_A; positions 192, 203, 256 and 259 to resolve subgroup HLA-DRB1_B; 256, 260, 317 and 351 to resolve subgroup HLA-DRB1_C; positions 155, 204, 233, 239, 256, 304, 357 and 366 to resolve subgroup HLA-DRB1_D; positions 122, 171, 257 and 317 to resolve subgroup HLA-DRB1_E; positions 164, 167, 171, 230, 235, 306, 317, 321 and 337 to resolve subgroup HLADRB1_F; positions 164, 257, 266 and 303 to resolve subgroup HLA-DRB1_G; positions 164, 181, 188, 220, 229, 256, 266, 317 and 318 to resolve subgroup HLA-DRB1_H; position 257 to resolve subgroup HLA-DRB1_I; positions 181, 239 and 357 to resolve subgroup HLA-DRB1_J; positions 122, 144, 239, 303, 317, 318 and 321 to resolve subgroup HLA-DRB1_K (sequences identical over exons 2 and 3 for alleles DRB1*110101 and DRB1*110102); positions 118, 161, 257, 260, 318 and 321 to resolve subgroup HLA-DRB1_L; positions 165, 257, 293 and 303 to resolve subgroup HLA-DRB1_M (sequences identical over exons 2 and 3 for alleles DRB1*120101 and DRB1*1206); positions 177, 240, 256, 257 and 357 to resolve subgroup HLA-DRB1_N; positions 150 175, 230, 236 and 321 to resolve subgroup HLA-DRB1_O (sequences identical over exons 2 and 3 for alleles DRB1*150101 and DRB1*1513); positions 115, 220 and 317 to resolve subgroup HLA-DRB1_P.

Another object of the invention is a kit to carry out the procedure. It consists of pooled combinations of primers. The primers that are used in the pools for HLA-A, HLA-B, and HLA-DRB1 and the masses of the genotyping products are listed in Tables IV, V, and VI respectively. CT refers to the mass shifting mass tag that is attached to that primer of the pool.

Another object of the invention is the use of the method of the invention for screening of tissue donors.

In a preferred embodiment, the use is for bone marrow donors in registries for screening of frequent and rare HLA types.

Still another object of the invention is the use of the primers represented in Table IV, V and VI to Carry out HLA typing.

TABLE III

| Subgroups of HLA-DRB1 | Alleles of Subgroups | Positions to resolve Subgroups |
|---|---|---|
| HLA-DRB1_A | DRB1*070101, DRB1*070102, DRB1*0703, DRB1*0704, DRB1*0705, DRB1*0707 | 123, 174, 250, 317 |
| HLA-DRB1_B | DRB1*040101, DRB1*040102, DRB1*0409, DRB1*0426, DRB1*0433 | 192, 203, 256, 259 |
| HLA-DRB1_C | DRB1*0404, DRB1*0410, DRB1*0423, DRB1*0440, DRB1*0444 | 256, 260, 317, 351 |
| HLA-DRB1_D | DRB1*040501, DRB1*040502, DRB1*040503, DRB1*040504, DRB1*0408, DRB1*0429, DRB1*0430, DRB1*0445, DRB1*0448 | 155, 204, 233, 239, 256, 304, 357, 366 |
| HLA-DRB1_E | DRB1*1402, DRB1*1409, DRB1*1413, DRB1*1446, DRB1*1447, DRB1*1448 | 122, 171, 257, 317 |
| HLA-DRB1_F | DRB1*130101, DRB1*130102, DRB1*130103, DRB1*1315, DRB1*1327 | 164, 167, 171, 230, 235, 306, 317, 321, 337 |
| HLA-DRB1_G | DRB1*130201, DRB1*130202, DRB1*1331, DRB1*1339, DRB1*1341 | 164, 257, 266, 303 |
| HLA-DRB1_H | DRB1*030101, DRB1*030102, DRB1*0307, DRB1*0312, DRB1*0313, DRB1*0315, DRB1*0316, DRB1*0318, DRB1*0322, DRB1*0323 | 164, 181, 188, 220, 229, 256, 266, 317, 318 |
| HLA-DRB1_I | DRB1*1137, DRB1*1425 | 257 |
| HLA-DRB1_J | DRB1*110401, DRB1*110402, DRB1*1143, DRB1*1146 | 181, 239, 357 |
| HLA-DRB1_K | DRB1*110101, DRB1*110102, DRB1*110103, DRB1*110104, DRB1*110105, DRB1*112701; DRB1*112702, DRB1*1130, DRB1*1139 | 122, 144, 239, 303, 317, 318, 321 |
| HLA-DRB1_L | DRB1*1117, DRB1*140101, DRB1*140102, ORB1*1408, DRB1*1426, DRB1*1438, DRB1*1439 | 118, 161, 257, 260, 318, 321 |
| HLA-DRB1_M | DRB1*120101, DRB1*120102, DRB1*1206, DRB1*1207, DRB1*1208, DRB1*1209 | 165, 257, 293, 303 |
| HLA-DRB1_N | DRB1*080101, DRB1*080102, DRB1*080201, DRB1*080202, DRB1*080203, DRB1*0807, DRB1*0811 | 177, 240, 256, 257, •357 |
| HLA-DRB1_O | DRB1*150101, DRB1*150103, DRB1*150105, DRB1*1503, DRB1*1506, DRB1*1509, DRB1*1513 | 150 175, 230, 236, 321 |
| HLA-DRB1_P | DRB1*010101, DRB1*0105, DRB1*0107, DRB1*0111 | 115, 220, 317 |

TABLE IV

| SEQ No. | ID NO | Name | Sequence | Primer CT | Masses | A | C | G | T |
|---|---|---|---|---|---|---|---|---|---|
| 1 | 1 | HLAA_811_1f20 | TGCTCGCCCCCAGGCTCCspC^spA | 0 | 1098.1 | 1425.1 | 1401.3 | — | — |
| 2 | 2 | HLAA_812_1f20 | TGCTCGCCCCCAGGCTCTspC^spA | 0 | 1113.1 | — | 1416.3 | 1452.4 | — |
| 3 | 3 | HLAA_921_1f20 | AGGCTCCCACTCCATGAGspC^spT | 0 | 1129.1 | 1456.4 | — | — | — |
| 4 | 4 | HLAA_922_1f20 | AGGCTCCCAMTCCATGAGspG^spT | 0 | 1169.1 | 1496.4 | — | 1512.4 | — |
| 5 | 5 | HLAA_923_1f20 | AGGCTCTCASTCCATGAGspG^spT | 0 | 1169.1 | 1496.4 | — | 1512.4 | — |
| 6 | 6 | HLAA_981_1f20 | CCACTCCATGAGGTATTTspC^spA | 0 | 1113.1 | — | 1416.3 | — | — |
| 7 | 7 | HLAA_982_1f20 | CCACTCCATGAGGTATTTspC^spT | 0 | 1104.1 | 1431.4 | 1407.3 | — | 1422.3 |
| 8 | 8 | HLAA_1231_2r20 | GCGATGMGCGGGGCTCspCspT^spC | 0 | 1510.5 | — | — | 1853.8 | — |
| 9 | 9 | HLAA_1232_2r20 | GCGATGMGCGGGGCTCspTspC^spC | —28 | 1380.4 | 1707.7 | — | — | — |
| 10 | 10 | HLAA_1233_2r20 | GCGATGMGCGGGGCTTspCspC^spC | 0 | 1408.4 | — | — | 1751.6 | — |
| 11 | 11 | HLAA_1234_2r20 | GMGATGMGCGGGGCTCspCspC^spC | 0 | 1393.4 | 1720.7 | — | 1736.7 | — |
| 12 | 12 | HLAA_2381_2r20 | CTSGTCCCMTACTCCGspGspA^spC | 0 | 1497.4 | — | 1800.6 | — | — |
| 13 | 13 | HLAA_2382_2r20 | CYCGTCCCMTACTCCGspGspA^spC | 0 | 1497.4 | — | 1800.6 | — | — |
| 14 | 14 | HLAA_2383_2r20 | CTCGTCCCMTACTCCGspGspC^spT | 0 | 1488.4 | — | 1791.6 | — | 1806.4 |
| 15 | 15 | HLAA_2384_2r20 | CTSGTCCCMTACTCAGspGspC^spC | 0 | 1473.4 | — | 1776.6 | — | — |
| 16 | 16 | HLAA_2385_2r20 | CYGGTCCCAATACTCCGspGspC^spC | 0 | 1473.4 | — | 1776.6 | — | — |
| 17 | 17 | HLAA_2386_2r20 | CMGGTCCCMTACTCCGspGspC^spC | 0 | 1473.4 | — | 1776.6 | — | — |
| 18 | 18 | HLAA_2387_2r20 | CYCGTCCCMTACTCCGspGspC^spC | 0 | 1473.4 | — | 1776.6 | — | — |
| 19 | 19 | HLAA_2561_1r19 | CTTCATATTCCGTGTCTCspC^spT | 0 | 1089.1 | — | 1392.3 | 1432.4 | — |
| 20 | 20 | HLAA_2562_1r19 | CTTCACwnCCGTGTCTCspC^spT | 0 | 1089.1 | — | 1392.3 | 1432.4 | — |
| 21 | 21 | HLAA_2563_1r19 | CTTCACATKCCGTGTCTGspC^spA | 0 | 1138.1 | — | — | 1481.4 | — |
| 22 | 22 | HLAA_2564_1r19 | CTTCACTTTCCGTGTGTTspC^spC | 0 | 1089.1 | — | — | 1432.1 | — |
| 23 | 23 | HLAA_2565_1r19 | CYTCACATTCCGTGTGTTspC^spC | 0 | 1089.1 | — | — | 1432.1 | — |
| 24 | 24 | HLAA_2566_1r19 | CTTCACRTTCCGTGTCTCspC^spC | 0 | 1074.1 | — | 1377.3 | 1417.4 | — |
| 25 | 25 | HLAA_2567_1r19 | CTTCASTTGCCGTGTCTCspC^spC | 0 | 1074.1 | — | 1377.3 | 1417.4 | — |
| 26 | 26 | HLAA_2568_1r19 | CTTCAGTTKCCGTGTCTCspC^pC | 0 | 1074.1 | — | 1377.3 | 1417.4 | — |

TABLE IV-continued

| SEQ ID NO. | No. | Name | Sequence | Primer CT | Masses | A | C | G | T |
|---|---|---|---|---|---|---|---|---|---|
| 28 | 27 | HLAA_2681_1f20 | ATTGGGACCGGMCACACspG^spG | 0 | 1154.1 | 1481.4 | 1457.3 | — | — |
| 29 | 28 | HLAA_2682_1f20 | ATTGGGACCTGCAGACACspG^spG | 0 | 1154.1 | 1481.4 | 1457.3 | — | — |
| 30 | 29 | HLAA_2683_1f20 | ATTGGGACSAGGAGACACspG^spG | 0 | 1154.1 | 1481.4 | 1457.3 | — | — |
| 31 | 30 | HLAA_2684_1f20 | ATTGGGACSGGGAGACACspG^spG | 0 | 1154.1 | 1481.4 | 1457.3 | — | — |
| 32 | 31 | HLAA_2685_1f20 | ATTGGGACSAGGAGACAGspG^spG | 0 | 1194.1 | 1521.4 | — | — | — |
| 33 | 32 | HLAA_2701_1r19 | CTGTGAGTGGGCCTTCspA^spT | 0 | 1113.1 | 1440.4 | — | — | — |
| 34 | 33 | HLAA_2702_1r19 | CTGTGACTGGGCCYTCspA^spC | —14 | 1084.1 | 1411.4 | — | 1427.4 | 1402.4 |
| 35 | 34 | HLAA_2703_1r19 | CTGTGAGTGGSCCTTCspA^spC | —14 | 1084.1 | 1411.4 | — | 1427.4 | 1402.4 |
| 36 | 35 | HLAA_2821_1f20 | ACACGGAATGTGARGGGCspC^spA | 0 | 1098.1 | — | 1401.3 | 1441.3 | — |
| 37 | 36 | HLAA_2822_1f20 | ACASGGAAAGTGAAGGCCspC^spA | 0 | 1098.1 | — | 1401.3 | 1441.3 | — |
| 38 | 37 | HLAA_2823_1f20 | ACACGGCAWGTGMGGGCCspC^spA | 0 | 1098.1 | — | 1401.3 | 1441.3 | — |
| 39 | 38 | HLAA_2824_1f20 | ACACGGAACGTGMGGGCCspC^spA | 0 | 1098.1 | — | 1401.3 | 1441.3 | — |
| 40 | 39 | HLAA_2825_1f20 | ACACGGMTRTGAAGGCCspC^spA | 0 | 1098.1 | — | 1401.3 | 1441.3 | — |
| 41 | 40 | HLAA_2921_2f20 | TGAAGGCCCACTCACAGspAspG^spT | —14 | 1498.4 | — | 1801.6 | — | — |
| 42 | 41 | HLAA_2922_2f20 | TGAAGGCCCACTCACAGspGspC^spT | 0 | 1488.4 | — | — | 1831.7 | — |
| 43 | 42 | HLAA_2923_2f20 | TGMGGSCCACTCACAGspAspT^spT | 0 | 1589.6 | — | — | 1932.9 | — |
| 44 | 43 | HLAA_2924_2f20 | TGARGGCCCAGTCACAGspAspC^spT | 0 | 1427.4 | — | 1775.6 | 1815.7 | — |
| 45 | 44 | HLAA_2925_2f20 | TGAAGGCCCASTCACAGspAspC^spT | 0 | 1427.4 | — | 1775.6 | 1815.7 | — |
| 46 | 45 | HLAA_3681_1f20 | TCACACCATCCAGATAATspG^spC | 0 | 1129.1 | 1456.4 | — | — | — |
| 47 | 46 | HLAA_3682_1f20 | TCACACCATCCAGMTMTspG^spT | 0 | 1144.1 | 1471.6 | 1447.1 | 1487.4 | 1462.3 |
| 48 | 47 | HLAA_3683_1f20 | TCACACCSTCCAGAGGATspG^spT | 0 | 1144.1 | 1476.1 | 1447.1 | 1487.4 | 1462.3 |
| 49 | 48 | HLAA_3684_1f20 | TCACACCVTCCAGATGATspG^spT | 0 | 1144.1 | 1471.6 | 1447.1 | 1487.4 | 1462.3 |
| 50 | 49 | HLAA_3961_2r20 | GCTGGTACCCGCGGAGspGspA^spG | 0 | 1537.4 | — | — | 1880.7 | — |
| 51 | 50 | HLAA_3962_2r20 | GCCGGTACCCGCGGAGspTspA^spA | 0 | 1496.4 | — | — | 1839.7 | — |
| 52 | 51 | HLAA_3963_2r20 | GGTGGTACCCGYGCAGspGspA^spA | 0 | 1496.4 | — | — | 1839.7 | — |
| 53 | 52 | HLAA_3964_2r20 | GGTGGTACCCGCAGAGspGspA^spA | 0 | 1521.5 | — | — | 1864.8 | 1839.7 |
| 54 | 53 | HLAA_3965_2r20 | GTTCATACCCGCGGAGspGspA^spA | 0 | 1521.5 | — | — | 1864.8 | 1839.7 |
| 55 | 54 | HLAA_3966_2r20 | GSTGGTACCCGCGGAGspGspA^spA | 0 | 1521.5 | — | — | 1864.8 | 1839.7 |
| 56 | 55 | HLAA_3967_2r20 | GCCGGTACCCGCGGAGspGspA^spA | 0 | 1521.5 | — | — | 1864.8 | 1839.7 |
| 57 | 56 | HLAA_4141_1f20 | CGCTTCCTCCGCGGGTATspG^spA | 0 | 1153.1 | 1480.1 | — | — | — |
| 58 | 57 | HLAA_4142_1f20 | CGCTTCCTCTGCGGGTACspC^spA | 0 | 1098.1 | — | 1401.3 | 1441.4 | — |
| 59 | 58 | HLAA_4143_1f20 | CGCTTCCTGCGCGGGTACspC^spA | 0 | 1098.1 | — | 1401.3 | 1441.4 | — |
| 60 | 59 | HLAA_4144_1f20 | CGCTTCCTCCACGGGTACspC^spA | 0 | 1098.1 | — | 1401.3 | 1441.4 | — |
| 61 | 60 | HLAA_4145_1f20 | CGMTTCCTCCGCGGGTACspC^spA | 0 | 1098.1 | — | 1401.3 | 1441.4 | — |
| 62 | 61 | HLAA_4146_1f20 | CGCCTCCTCCGCGGGTACspC^spA | 0 | 1098.1 | — | 1401.3 | 1441.4 | — |
| 63 | 62 | HLAA_4147_1f20 | CACTTCCTCCGCGGGTACspC^spG | 0 | 1114.1 | — | — | 1457.4 | — |
| 64 | 63 | HLAA_4148_1f20 | CGCTTMCTCCGCGGGTACspC^spG | 0 | 1114.1 | — | — | 1457.4 | — |
| 65 | 64 | HLAA_4531_1r20 | GTCCAAGAGCGCAGGTCTspT^spC | 0 | 1206.2 | — | — | — | 1524.4 |
| 66 | 65 | HLAA_4532_1r20 | GTCCAAGAGCCAGGTCCspT^spC | 0 | 1191.2 | — | — | 1534.5 | 1509.4 |
| 67 | 66 | HLAA_4533_1r20 | GTCCAGGAGCTCAGGTCCspT^spG | 0 | 1191.2 | — | — | 1534.5 | 1509.4 |
| 68 | 67 | HLAA_5021_2r20 | GGCCGYCTCCCACTTGTspGspC^spT | 0 | 1463.4 | — | — | — | 1781.6 |
| 69 | 68 | HLAA_5022_2r20 | GGCYGCCTCCCACTTGCspGspC^spT | 0 | 1448.4 | — | 1751.6 | 1791.7 | 1766.6 |
| 70 | 69 | HLAA_5023_2r20 | CGGAGTCTCCCACTTGCspGspG^spT | 0 | 1448.4 | — | 1751.6 | 1791.7 | 1766.6 |
| 71 | 70 | HLAA_5024_2r20 | GGCCGCCTCCCACTTGCspGspC^spC | —14 | 1419.4 | — | — | — | 1737.6 |
| 72 | 71 | HLAA_5271_1f20 | AGTGGGAGACTCCGCCCAspT^spG | 0 | 1255.3 | 1582.6 | 1558.5 | — | 1573.5 |
| 73 | 72 | HLAA_5272_1f20 | CMGTGGGAGGCGGYCCAspT^spG | 0 | 1255.3 | 1582.6 | 1558.5 | — | 1573.5 |
| 74 | 73 | HLAA_5273_1f20 | CMGTGGGAGTCGGCCCAspT^spG | 0 | 1255.3 | 1582.6 | 1558.5 | — | 1573.5 |
| 75 | 74 | HLAA_5274_1f20 | CMGTGGGAGGCGGCCCTspT^spG | 0 | 1246.3 | — | — | — | 1564.5 |
| 76 | 75 | HLAA_5275_1f20 | CMGTGGGAGGCGGCCCGspT^spT | 0 | 1246.3 | — | — | 1589.6 | — |
| 77 | 76 | HLAA_5276_1f20 | CMGTGGGAGGCGGCCCCspT^spC | 0 | 1231.3 | — | — | 1574.5 | — |
| 78 | 77 | HLAA_5277_1f20 | CMGTGGGAGGCGGCCMGspT^spG | 0 | 1271.3 | 1598.6 | — | — | 1589.5 |
| 79 | 78 | HLAA_5278_1f20 | CMGTGGGAGGCTGCCCGspT^spG | 0 | 1271.3 | 1598.6 | — | — | 1589.5 |
| 80 | 79 | HLAA_5391_1f19 | GCCCRTGAGGCGGAGCAspG^spC | 0 | 1138.1 | 1465.4 | — | 1481.4 | 1456.3 |
| 81 | 80 | HLAA_5392_1f19 | GYCCATGCGGCGGAGCAspG^spC | 0 | 1138.1 | 1465.4 | — | 1481.4 | 1456.3 |
| 82 | 81 | HLAA_5393_1f19 | GCCCGTCGGGCGGAGCAspG^spC | 0 | 1138.1 | 1465.4 | — | 1481.4 | 1456.3 |
| 83 | 82 | HLAA_5394_1f19 | GCCCATGTGGCGGAGCAspG^spC | 0 | 1138.1 | 1465.4 | — | 1481.4 | 1456.3 |
| 84 | 83 | HLAA_5395_1f19 | GTCCATGCGGCGGAGCAspG^spT | 0 | 1153.1 | — | — | 1496.4 | 1471.3 |
| 85 | 84 | HLAA_5396_1f19 | GCCCGTYGGGCGGAGCAspG^spT | 0 | 1153.1 | — | — | 1496.4 | 1471.3 |
| 86 | 85 | HLAA_5397_1f19 | GCCCATGAGGCGGAGCAspG^spT | 0 | 1153.1 | — | — | 1496.4 | 1471.3 |
| 87 | 86 | HLAA_5398_1f19 | GCCCWTGTGGCGGAGCAspG^spT | 0 | 1153.1 | — | — | 1496.4 | 1471.3 |
| 88 | 87 | HLAA_5399_1f19 | GCCMGTGTGGCGGAGCAspG^spT | 0 | 1153.1 | — | — | 1496.4 | 1471.3 |
| 89 | 88 | HLAA_5591_1r20 | GCGGAGCCACTCCACGCAspC^spT | 0 | 1113.1 | — | 1416.3 | — | — |
| 90 | 89 | HLAA_5592_1r20 | GCGGAGCCCGTCCACGCAspC^spT | 0 | 1113.1 | — | 1416.3 | — | — |
| 91 | 90 | HLAA_5593_1r20 | GCGGAGCCACTCCACGCAspC^spA | 0 | 1122.1 | — | — | 1465.4 | — |
| 92 | 91 | HLAA_5594_1r20 | GCGGAGCCCGTCCACTCAspC^spG | 0 | 1138.1 | — | — | — | 1456.3 |

TABLE IV-continued

| No. | SEQ ID NO | Name | Sequence | Primer CT | Masses | A | C | G | T |
|---|---|---|---|---|---|---|---|---|---|
| 93 | 92 | HLAA_5595_1r20 | GCGGAGCCAGTCCACGCAspC^spG | 0 | 1138.1 | — | — | — | 1456.3 |
| 94 | 93 | HLAA_5596_1r20 | GCGGAGCCMGTCCACGCAspC^spG | 0 | 1138.1 | — | — | — | 1456.3 |
| 95 | 94 | HLAA_5597_1r20 | GCGGAGCCACTCCACGCAspC^spC | 0 | 1098.1 | 1425.4 | — | 1441.4 | — |
| 96 | 95 | HLAA_5598_1r20 | GCGGAGCCCGTCCACGCAspC^spC | 0 | 1098.1 | 1425.4 | — | 1441.4 | — |
|  | 243 | HLAA_5599_1r20 | GCGGAGCCACTCCACGCAspG^spG |  | 1178.1 | — | — | — | 1496.3 |
| 97 | 96 | HLAA_5711_2f20 | TGGAGGGCCKGTGCGTGspGspA^spG | 0 | 1537.4 | — | — | — | 1855.6 |
| 98 | 97 | HLAA_5712_2f20 | TGGAGGGYGAGTGCGTGspGspA^spG | 0 | 1537.4 | — | — | — | 1855.6 |
| 99 | 98 | HLAA_5713_2f20 | TGSAGGGCCGGTGCGTGspGspA^spG | 0 | 1537.4 | — | — | — | 1855.6 |
| 100 | 99 | HLAA_5714_2f20 | TGGATGSCACGTGCGTGspGspA^spG | 0 | 1537.4 | — | — | — | 1855.6 |
| 101 | 100 | HLAA_5715_2f20 | TGGAGGGCACSTGCGTGspGspA^spG | 0 | 1537.4 | — | — | — | 1855.6 |
| 102 | 101 | HLAA_5716_2f20 | TGGAGGGCACGTGMGTGspGspA^spC | 0 | 1497.4 | — | — | 1840.7 | 1815.6 |
| 103 | 102 | HLAA_5717_2f20 | TGGAGGGCYGGTGCGTGspGspA^spC | 0 | 1497.4 | — | — | 1840.7 | 1815.6 |

TABLE V

| No. | SEQ ID NO | Name | Sequence | Primer CT | Masses | A | C | G | T |
|---|---|---|---|---|---|---|---|---|---|
| 1 | 103 | HLAB_971_2f20 | CCCACTCCATGAGGCATspTspT^spC | 0 | 1540.3 | — | 1843.7 | 1883.8 | 1858.7 |
| 2 | 104 | HLAB_972_2f20 | CCCACTYCATGAGGTA TspTspT^spC | 0 | 1540.3 | — | 1843.7 | 1883.8 | 1858.7 |
| 3 | 105 | HLAB_2061_1f20 | CGACGCCGCGAGTCMGAGspG^spA | -28 | 1150.1 | 1477.4 | 1453.3 | — | 1468.3 |
| 4 | 106 | HLAB_2062_1f20 | CGACGCCACGAGTCCGAGspG^spA | -28 | 1150.1 | 1477.4 | 1453.3 | — | 1468.3 |
| 5 | 107 | HLAB_2063_1f20 | CGACGCCGCGAGTCCRAGspA^spG | 0 | 1178.1 | 1505.4 | — | 1521.4 | — |
| 6 | 108 | HLAB_2064_1f20 | CGACGCCRCGAGTCCGAGspA^spG | 0 | 1178.1 | 1505.4 | — | 1521.4 | — |
| 7 | 109 | HLAB_2221_1r19 | GCCCCTCCTGCTCCACCspC^spA | 0 | 1098.3 | 1425.4 | — | 1441.4 | — |
| 8 | 110 | HLAB_2222_1r19 | GCCCCTCYTGCTCTATCspC^spA | 0 | 1098.3 | 1425.4 | — | 1441.4 | — |
| 9 | 111 | HLAB_2591_2f20 | GGCCGGAGTATTGGGACspGspG^spG | 0 | 1513.4 | — | — | 1856.7 | — |
| 10 | 112 | HLAB_2592_2f20 | GGCCGGAGTATTGGGACspGspA^spG | 0 | 1497.4 | — | — | 1840.7 | — |
| 11 | 113 | HLAB_2593_2f20 | GGCCGGAGTATTGGGACspCspC^spG | -28 | 1405.4 | — | — | 1748.7 | — |
| 12 | 114 | HLAB_2594_2f20 | GGCCGGAGTATTGGGATspCspG^spG | 0 | 1488.4 | 1815.7 | — | 1831.7 | — |
| 13 | 115 | HLAB_2595_2f20 | GGCCGGAGTTTTGGGACspCspG^spG | -28 | 1445.4 | 1772.7 | — | 1788.7 | — |
| 14 | 116 | HLAB_2596_2f20 | GGCCGGAGCATTGGGACspCspG^spG | -28 | 1445.4 | 1772.7 | — | 1788.7 | — |
| 15 | 117 | HLAB_2597_2f20 | GGCCGGGATATTGGGACspCspG^spG | -28 | 1445.4 | 1772.7 | — | 1788.7 | — |
| 16 | 118 | HLAB_2598_2f20 | GGCCRGAATATTGGGACspCspG^spG | -28 | 1445.4 | 1772.7 | — | 1788.7 | — |
| 17 | 119 | HLAB_2599_2f20 | GGCGGGMGTATTGGGACspCspG^spG | -28 | 1445.4 | 1772.7 | — | 1788.7 | — |
| 18 | 120 | HLAB_25910_2f20 | GGCCTTAGTATTGGGACspCspG^spG | -28 | 1445.4 | 1772.7 | — | 1788.7 |  |
| 19 | 121 | HLAB_2721_1f20 | GGACSGGGAGACACGGAAspC^spA | 0 | 1122.1 | — | — | — | 1440.3 |
| 20 | 122 | HLAB_2722_1f20 | GGACGRGGAGACACGGAAsPC^spA | 0 | 1122.1 | — | — | — | 1440.3 |
| 21 | 123 | HLAB_2723_1f20 | GGACCGGAACACACAGAC^spT | 0 | 1113.1 | — | — | 1456.4 | — |
| 22 | 124 | HLAB_2724_1f20 | GGACCGGAACACACAGACspC^spT | -14 | 1075.1 | — | — | — | 1393.3 |
| 23 | 125 | HLAB_2725_1f20 | GGACCGGGAGACACAGAAspG^spT | 0 | 1153.1 | 1480.4 | — | — | — |
| 24 | 126 | HLAB_2726_1f20 | GGACCGGGAGATACAGATspC^spT | 0 | 1104.1 | 1431.4 | 1407.3 | 1447.4 | 1422.3 |
| 25 | 127 | HLAB_2727_1f20 | GGACCGGGAGASACAGATspC^spT | 0 | 1104.1 | 1431.4 | 1407.3 | 1447.4 | 1422.3 |
| 26 | 128 | HLAB_2728_1f20 | GGACCGGGACACACAGATspC^spT | 0 | 1104.1 | 1431.4 | 1407.3 | 1447.4 | 1422.3 |
| 27 | 129 | HLAB_2729_1f20 | GGACCSGGAGACACAGATspC^spT | 0 | 1104.1 | 1431.4 | 1407.3 | 1447.4 | 1422.3 |
| 28 | 130 | HLAB_2921_2f19 | CAAGACCAACACACAGspGspC^spT | 0 | 1458.3 | — | — | 1801.6 | — |
| 29 | 131 | HLAB_2922_2f19 | CAAGSCCCAGGCACAGspGspC^spT | 0 | 1458.3 | — | — | 1801.6 | — |
| 30 | 132 | HLAB_2923_2f19 | CAAGACCAACACACAGGspAspC^spT | -28 | 1414.3 | — | — | 1757.6 | 1732.5 |
| 31 | 133 | HLAB_2924_2f19 | GAAGGCCTCCGCGCAGspAspC^spT | -28 | 1414.3 | — | — | 1757.6 | 1732.5 |
| 32 | 134 | HLAB_2925_2f19 | CAAGGCCMAGGCACAGspAspC^spT | -28 | 1414.3 | — | — | 1757.6 | 1732.5 |
| 33 | 135 | HLAB_2926_2f19 | CAAGSGCCAGGCACAGspAspC^spT | -28 | 1414.3 | — | — | 1757.6 | 1732.5 |
| 34 | 136 | HLAB_2927_2f19 | GAAGACCAACACACAGspAspC^spT | -28 | 1414.3 | — | — | 1757.6 | 1732.5 |
| 35 | 137 | HLAB_3021_2f19 | GCACAGACTGACCGAGspTspG^spG | 0 | 1528.4 | — | — | 1871.7 | — |
| 36 | 138 | HLAB_30211_2f19 | ACACAGACTTACAGAGspAspG^spA | -28 | 1493.5 | 1820.8 | — | 1836.8 | — |
| 37 | 139 | HLAB_3022_2f19 | ACAGAGACTTACCGAGspAspG^spG | 0 | 1537.4 | 1864.7 | — | — | — |
| 38 | 140 | HLAB_3023_2f19 | RCACAGACTGACCGAGspAspG^spG | 0 | 1537.4 | 1864.7 | — | — | — |

TABLE V-continued

| SEQ No. | ID NO | Name | Sequence | Primer CT | Masses | A | C | G | T |
|---|---|---|---|---|---|---|---|---|---|
| 39 | 141 | HLAB_3024_2f19 | GCACAGACTGGCCGAGspTspG^spA | -28 | 1481.4 | 1811.7 | — | 1827.7 | — |
| 40 | 142 | HLAB_3025_2f19 | ACACAGACTTACCGAGspTspG^spA | -28 | 1481.4 | 1811.7 | — | 1827.7 | — |
| 41 | 143 | HLAB_3026_2f19 | RCACAGACTGACCGAGspTspG^spA | -28 | 1481.4 | 1811.7 | — | 1827.7 | — |
| 42 | 144 | HLAB_3027_2f19 | ACACAGGCTGACCGAGspAspG^spA | -28 | 1493.5 | 1820.8 | — | 1836.8 | — |
| 43 | 145 | HLAB_3028_2f19 | RCACAGACTGACCGAGspAspG^spA | -28 | 1493.5 | 1820.8 | — | 1836.8 | — |
| 44 | 146 | HLAB_3029_2f19 | GCRCAGACTTACCGAGspAspG^spA | -28 | 1493.5 | 1820.8 | — | 1836.8 | — |
| 45 | 147 | HLAB_30210_2f19 | ACACRGACTTACCGAGspAspG^spA | -28 | 1493.5 | 1820.8 | — | 1836.8 | — |
| 46 | 148 | HLAB_3621_2f20 | CGGGTCTCACACCCTCCspAspC^spA | -28 | 1413.4 | — | — | 1756.7 | — |
| 47 | 149 | HLAB_3622_2f20 | CGGGTCTCACAYCATCCspAspG^spA | -14 | 1467.4 | 1794.7 | 1770.6 | 1810.7 | 1785.6 |
| 48 | 150 | HLAB_3623_2f20 | CGGKTCTCACACCCTCCspAspG^spA | -14 | 1467.4 | 1794.7 | 1770.6 | 1810.7 | 1785.6 |
| 49 | 151 | HLAB_3624_2f20 | CGGGTCTCACACTTGGCspAspG^spA | -14 | 1467.4 | 1794.7 | 1770.6 | 1810.7 | 1785.6 |
| 50 | 152 | HLAB_3625_2f20 | CGGGTCTCACATCATCCspAspG^spA | -14 | 1483.4 | — | — | — | 1801.6 |
| 51 | 153 | HLAB_3626_2f20 | CGGGTCTCACACCCTCCspAspG^spT | 0 | 1472.4 | — | — | 1815.7 | — |
| 52 | 154 | HLAB_3631_1r20 | CCCASGTCGCAGCCGTACspA^spT | -28 | 1085.1 | — | 1388.3 | 1428.4 | 1403.3 |
| 53 | 155 | HLAB_3632_1r20 | CCCASGTCGCAGCCATACspA^spT | -28 | 1085.1 | — | 1388.3 | 1428.4 | 1403.3 |
| 54 | 156 | HLAB_3633_1r20 | CCCASGTCGCAGCCAAACspA^spT | -28 | 1085.1 | — | 1388.3 | 1428.4 | 1403.3 |
| 55 | 157 | HLAB_3634_1r20 | CCCACGTCGCAGCCAGACspA^spT | -28 | 1085.1 | — | 1388.3 | 1428.4 | 1403.3 |
| 56 | 158 | HLAB_3635_1r20 | CCCACGTCGCAGCCGCACspA^spT | -28 | 1085.1 | — | 1388.3 | 1428.4 | 1403.3 |
| 57 | 159 | HLAB_3636_420 | CCCACGTCGCAGCCTTACspA^spT | -28 | 1085.1 | — | 1388.3 | 1428.4 | 1403.3 |
| 58 | 160 | HLAB_3637_1r20 | CCCACGTCGCAGCCGTACspG^spT | 0 | 1129.1 | — | 1432.3 | 1472.4 | 1447.3 |
| 59 | 161 | HLAB_3691_1f20 | TCCGGCCCCAKGTCGCAGspC^spC | 0 | 1114.1 | 1441.4 | — | 1457.4 | 1432.3 |
| 60 | 162 | HLAB_3692_1f20 | TCGGGCCCCASGTCGCAGspC^spC | 0 | 1114.1 | 1441.4 | — | 1457.4 | 1432.3 |
| 55 | 163 | HLAB_4121_2f20 | GGCGCCTCCTCCGCGGGspTspA^spC | -28 | 1444.4 | — | 1747.6 | — | — |
| 56 | 164 | HLAB_4122_2f20 | GGCGCCTCCTCCSCGGGspCspA^spT | 0 | 1472.4 | 1799.7 | — | 1815.7 | — |
| 57 | 165 | HLAB_4123_2f20 | GGCGCYTCCTCCGCGGGspCspA^spT | 0 | 1472.4 | 1799.7 | — | 1815.7 | — |
| 58 | 166 | HLAB_4124_2f20 | GGCGTCTCCTCCGCGGTspTspA^spT | 0 | 1462.4 | — | 1765.6 | — | — |
| 59 | 167 | HLAB_4125_2f20 | GGCGCCTCCTCCGCGGGspTspA^spT | -14 | 1473.4 | — | 1776.6 | — | — |
| 60 | 168 | HLAB_4181_2f20 | TCCTCCGCGGGTATGMspCspA^spG | 0 | 1481.4 | 1808.7 | — | — | — |
| 61 | 169 | HLAB_4182_2f20 | TCCTCCACGGGTACCACspCspA^spG | 0 | 1457.4 | — | — | — | 1775.6 |
| 62 | 170 | HLAB_4183_2f20 | TCCTGCGCGGGTACCACspCspA^spG | 0 | 1457.4 | — | — | — | 1775.6 |
| 63 | 171 | HLAB_4184_2f20 | TCCTCCGCGGGTACCACspCspA^spG | 0 | 1457.4 | — | — | — | 1775.6 |
| 64 | 172 | HLAB_4185_2f20 | TCCTCTGCGGGTACCACspCspA^spG | 0 | 1457.4 | — | — | — | 1775.6 |
| 65 | 173 | HLAB_4186_2f20 | TCCTCCGCGGGTACCAGspCspA^spG | 0 | 1497.4 | 1824.7 | 1800.6 | 1840.7 | 1815.6 |
| 66 | 174 | HLAB_4187_2f20 | TMCTCCGCGGGTACCGGspCspA^spG | 0 | 1497.4 | 1824.7 | 1800.6 | 1840.7 | 1815.6 |
| 67 | 175 | HLAB_4188_2f20 | TCCTCCGCGGGTACCAGspCspG^spG | 0 | 1513.4 | — | 1856.7 | — | — |
| 68 | 176 | HLAB_4191_2r20 | AATCCTTGCCGTCGTAGspGspC^spT | -14 | 1474.4 | 1801.7 | — | — | — |
| 69 | 177 | HLAB_4192_2r20 | AATCCTTGCCGTCGTAGspGspC^spA | -28 | 1469.4 | — | — | 1812.7 | — |
| 70 | 178 | HLAB_4193_2r20 | AATTCTTGCCGTCGTAGspGspC^spG | 0 | 1513.4 | 1840.7 | — | 1856.7 | 1831.6 |
| 71 | 179 | HLAB_4194_2r20 | AATCTTTGCCGTCGTAGspGspC^spG | 0 | 1513.4 | 1840.7 | — | 1856.7 | 1831.6 |
| 72 | 180 | HLAB_4195_2r20 | AATCCTTGCCGTCGYAGspGspC^spG | 0 | 1513.4 | 1840.7 | — | 1856.7 | 1831.6 |
| 73 | 181 | HLAB_43510_1r20 | TCMTTCAGGGCGATGTAAspT^spC | -14 | 1201.3 | — | 1504.4 | — | 1519.4 |
| 74 | 182 | HLAB_43520_1r20 | TCGTTCAGGGCGATGTAAspT^spT | 0 | 1230.3 | — | 1533.5 | — | — |
| 75 | 183 | HLAB_5271_1f20 | CMGTGGGAGGCGGCCCTspT^spG | 0 | 1246.3 | — | — | — | 1564.5 |
| 76 | 184 | HLAB_5272_1f20 | CMGTKGGAGGCGGCCCGspT^spG | 0 | 1271.3 | 1598.6 | 1574.3 | — | 1589.5 |
| 77 | 185 | HLAB_5391_1f20 | GGCCCGTGYGGCGGAGCspAspG^spC | 0 | 1138.1 | — | — | 1481.3 | 1456.3 |
| 78 | 186 | HLAB_5392_1f20 | GGCCCGTGTCGCGGAGCspAspG^spG | 0 | 1178.1 | 1505.4 | — | — | — |
| 79 | 187 | HLAB_5393_1f20 | GGCCCGTGWGGCGGAGCspAspG^spG | 0 | 1178.1 | 1505.4 | — | — | — |
| 80 | 188 | HLAB_5394_1f20 | GGCCCGTGAGGCGGAGCspAspG^spT | 0 | 1153.1 | — | — | 1496.4 | — |
| 81 | 189 | HLAB_5591_1r20 | GCGGAGCGACTCCACGCspAspC^spT | 0 | 1113.1 | — | — | 1456.4 | — |
| 82 | 190 | HLAB_5592_1r20 | GCGGAGCCACTCCACGCspAspC^spT | 0 | 1113.1 | — | — | 1456.4 | — |
| 83 | 191 | HLAB_5593_1r20 | GCGGAGCCAATCCACGCspAspC^spT | 0 | 1113.1 | — | — | 1456.4 | — |
| 84 | 192 | HLAB_5594_1r20 | GCGGAGCCACTCCACGCspAspC^spG | 0 | 1152.1 | — | — | — | 1470.3 |
| 85 | 193 | HLAB_5595_1r20 | GCGGAGCGACTCCRCGCspAspC^spA | -14 | 1122.1 | 1449.1 | 1425.3 | — | — |
| 86 | 194 | HLAB_5596_1r20 | GCGGAGCSACTCCACGCspAspC^spA | -14 | 1122.1 | 1449.1 | 1425.3 | — | — |
| 87 | 195 | HLAB_5597_1r20 | GCGGAGCCCGTCCACGCspAspC^spA | -14 | 1122.1 | 1449.1 | 1425.3 | — | — |

TABLE V-continued

| SEQ ID NO | No. | Name | Sequence | CT | Primer Masses | A | C | G | T |
|---|---|---|---|---|---|---|---|---|---|
| 88 | 196 | HLAB_5711_1r20 | CTCCAGGTAYCTGCGGAGspC^spG | 0 | 1154.1 | 1481.4 | — | — | — |
| 89 | 197 | HLAB_5712_1r20 | CTCCAGGTRTCTGCGGAGspC^spC | 0 | 1114.1 | 1441.4 | 1417.3 | — | — |
| 90 | 198 | HLAB_583_1r19 | ACCTGGAGAACGGGAAGspG^spA | 0 | 1178.1 | 1505.4 | — | 1521.4 | — |

TABLE VI

| | SEQ ID NO | Name | Sequence | CT | Masses Primer | A | C | G | T |
|---|---|---|---|---|---|---|---|---|---|---|
| 1 | 199 | DRB1_1251_1r20 | CATTGAAGAAATGACACTspC^spC | 0 | 1098.1 | — | 1392.3 | — | — |
| 2 | 200 | DRB1_1252_1r20 | CGTTGAAGAAATGACACTspT^spA | 0 | 1230.1 | — | — | — | 1548.5 |
| 3 | 201 | DRB1_1253_1r20 | CATTGAAGAAATGACATTspC^spA | 0 | 1113.1 | 1440.4 | 1416.3 | 1456.4 | 1431.3 |
| 4 | 202 | DRB1_1254_1r20 | CATTGAAGAAWTAACACTspC^spA | 0 | 1113.1 | 1440.4 | 1416.3 | 1456.4 | 1431.3 |
| 5 | 203 | DRB1_1255_1r20 | CRTTGAAGAAATGACACTspC^spA | 0 | 1113.3 | 1440.4 | 1416.3 | 1456.4 | 1431.3 |
| 6 | 204 | DRB1_1961_1f19 | CATCTATAACCAAGAGGspA^spA | 0 | 1162.1 | — | — | — | 1480.3 |
| 7 | 205 | DRB1_1962_1f19 | CTTCTATCACCAAGARGspA^spG | 0 | 1178.1 | 1505.4 | — | — | 1496.3 |
| 8 | 206 | DRB1_1963_1f19 | CTTCTATAATCARGAGGspA^spG | 0 | 1178.1 | 1505.4 | — | — | 1496.3 |
| 9 | 207 | DRB1_1964_1f19 | CGTCCATAACCAAGAGGspA^spG | 0 | 1178.1 | 1505.4 | — | — | 1496.3 |
| 10 | 208 | DRB1_1965_1f19 | CATCTATAACCAAGAGGspA^spG | 0 | 1178.1 | 1505.4 | — | — | 1496.3 |
| 11 | 209 | DRB1_1966_1f19 | CTTCCATAACCRGGAGGspA^spG | 0 | 1178.1 | 1505.4 | — | — | 1496.3 |
| 12 | 210 | DRB1_1967_1f19 | CTTCGATAACCAGGAGGspA^spG | 0 | 1178.1 | 1505.4 | — | — | 1496.3 |
| 13 | 211 | DRB1_1968_1f19 | CTTCTATAACCTGGAGGspA^spG | 0 | 1178.1 | 1505.4 | — | — | 1496.3 |
| 14 | 212 | DRB1_1971_1r20 | CGTCGCTGTCGAAGCGCAspG^spG | 0 | 1178.1 | 1505.4 | — | — | 1496.3 |
| 15 | 213 | DRB1_1972_1r20 | CGTCGCTGTCGTAGCGCGspC^spG | 0 | 1154.1 | — | — | — | 1472.3 |
| 16 | 214 | DRB1_1973_1r20 | CGTCGCTGTCGAAGCGCAspA^spG | 0 | 1162.1 | — | — | — | 1480.3 |
| 17 | 215 | DRB1_1974_1r20 | CGTCGCTGTCGAAGYGCAspC^spG | -28 | 1110.1 | 1437.4 | — | 1453.4 | 1428.3 |
| 18 | 216 | DRB1_1975_1r20 | CGTCGCTGTCGAASCGCAspC^spG | -28 | 1110.1 | 1437.4 | — | 1453.4 | 1428.3 |
| 19 | 217 | DRB1_2271_1f20 | CGACAGCGACGTGGGGAspC^spT | 0 | 1113.1 | 1440.4 | — | — | — |
| 20 | 218 | DRB1_2272_1f20 | CGACAGCGACGTGYGGGAspG^spT | 0 | 1153.1 | 1480.4 | — | — | 1471.3 |
| 21 | 219 | DRB1_2611_1r20 | TTCTGGCTGTTCCAGTACspT^spG | 0 | 1231.2 | — | — | 1574.5 | — |
| 22 | 220 | DRB1_2612_1r20 | TTCTGGCTGTTCCAGTACspC^spC | 0 | 1074.1 | — | 1377.3 | — | — |
| 23 | 221 | DRB1_2613_1r20 | TTCTGGCTGTTCCAGTAGspT^spC | 0 | 1231.2 | — | 1534.4 | — | — |
| 24 | 222 | DRB1_2614_1r20 | TTCTGGCTGTTCCAGTRCspT^spC | -14 | 1177.2 | 1504.5 | 1480.4 | 1520.5 | — |
| 25 | 223 | DRB1_2615_1r20 | TTCYGGCTGTTCCAGGACspT^spC | -14 | 1177.2 | 1504.5 | 1480.4 | 1520.5 | — |
| 26 | 224 | DRB1_2861_1f19 | CTGGAACAGCCAGAAGAspA^spC | -28 | 1122.1 | 1449.4 | — | — | — |
| 27 | 225 | DRB1_2862_1f19 | CTGGAACAGCCRGAAGGspA^spC | 0 | 1138.1 | 1465.4 | 1441.3 | — | 1456.3 |
| 28 | 226 | DRB1_2991_1f20 | GAAGACHTCCTGGAGCAspG^spG | 0 | 1178.1 | — | 1481.3 | — | — |
| 29 | 227 | DRB1_2992_1f20 | GAAGGACATCCTGGGAGspC^spA | -14 | 1108.1 | 1435.1 | — | 1451.4 | — |
| 30 | 228 | DRB1_2993_1f20 | GAAGGACATCCTGGARGAspC^spA | -14 | 1108.1 | 1435.1 | — | 1452.4 | — |
| 31 | 229 | DRB1_2994_1f20 | GAAGGACYTCCTGGMGAspC^spA | -14 | 1108.1 | 1435.1 | — | 1453.4 | — |
| 32 | 230 | DRB1_2995_1f20 | GAAGGACATCCTGGAGCAspG^spA | 0 | 1162.1 | 1489.4 | — | 1505.4 | — |
| 33 | 231 | DRB1_2996_1f20 | GAAGGACHTCCTGGAGCGspG^spA | 0 | 1178.1 | — | — | 1521.4 | — |
| 34 | 232 | DRB1_2997_1f20 | GAAGGACHTCCTGGAAGAspC^spG | 0 | 1138.1 | 1465.4 | — | — | — |
| 35 | 233 | DRB1_3081_1r20 | GTCTGCAATAGGTGTCCAspC^spG | 0 | 1138.1 | — | 1441.3 | — | — |
| 36 | 234 | DRB1_3082_1r20 | GTCTGCARTAGGCGTCCAspC^spC | -14 | 1084.1 | 1411.4 | 1387.3 | 1427.4 | 1402.3 |
| 37 | 235 | DRB1_3083_1r20 | GTCTGCCAGTAATTGTCCAspC^spC | -14 | 1084.1 | 1411.4 | 1387.3 | 1427.4 | 1402.3 |
| 38 | 236 | DRB1_3084_1r20 | GTCTGCACACGGTGTCCAspC^spC | -14 | 1084.1 | 1411.4 | 1387.3 | 1427.4 | 1402.3 |
| 39 | 237 | DRB1_3085_1r20 | GTCTGCCAGTAGGTGTCCAspC^spC | -14 | 1084.1 | 1411.4 | 1387.3 | 1427.4 | 1402.3 |
| 40 | 238 | DRB1_3086_1r20 | GTCTGCAATAGGTGTCCAspC^spC | -14 | 1084.1 | 1411.4 | 1387.3 | 1427.4 | 1402.3 |
| 41 | 239 | DRB1_341_1f19 | TGCAGACACAACTACSGspG^spG | 0 | 1191.1 | — | — | 1497.3 | 1512.3 |
| 42 | 240 | DRB1_3451_1r20 | CGCTGCACTGTGAATCTCspT^spC | 0 | 1191.3 | 1518.5 | 1494.4 | — | — |
| 43 | 241 | DRB1_3452_1r20 | CTCTGCACTGTGAAGCTCspT^spC | 0 | 1191.3 | 1518.5 | 1494.4 | — | — |
| 44 | 242 | DRB1_3453_1r20 | CGCTGCACYGTGAAGCTCspT^SpC | 0 | 1191.3 | 1518.5 | 1494.4 | — | — |

The resolution achievable by 19 markers each for HLA-A and HLA-B and the ten markers for HLA-DRB1 are listed in Tables VII to IX below.

TABLE VII

| Frequent Alleles of HLA-A | Group of frequent Alleles with same four-digit type | Rare Alleles with same Mini-Haplotype Profile | Resolution (in %) |
|---|---|---|---|
| A*0101 | A*010101, A*010102 | A*0103, A*0104N, A*0109 | 98.3 |
| A*0201 | A*02010101, A*02010102L, A*020103, A*020104, A*020108, | A*0204, A*0209, A*0225, A*0231, A*0232N, A*0242, A*0243N, A*0253N, A*0258, A*0260, A*0264, A*0266, A*0267 | 93.4 |

TABLE VII-continued

| Frequent Alleles of HLA-A | Group of frequent Alleles with same four-digit type | Rare Alleles with same Mini-Haplotype Profile | Resolution (in %) |
|---|---|---|---|
| | A*020109 A*020102 A*020105 A*020106 A*020107 | | 100 100 100 100 |
| A*0301 | A*03010101, A*03010102N A*030102 A*030103 | A*0303N, A*0304, A*0305, A*0306, A*311N | 97.6 100 100 |
| A*2301 | A*2301 | A*2306, A*2307N, A*2308N | 98.6 |
| A*2402 | A*24020101, A*24020102L, | A*2404, A*2409N, A*2411N, A*2426, A*2427, | 94.5 |

TABLE VII-continued

| Frequent Alleles of HLA-A | Group of frequent Alleles with same four-digit type | Rare Alleles with same Mini-Haplotype Profile | Resolution (in %) |
|---|---|---|---|
| | A*240202, A*240203, A*240204 | A*2432, A*2435, A*2436N, A*2437, A*2439 | |
| A*2902 | A*290201 | A*29010101, A*29010102N, A*2906, A*2908N | 98.3 |
| | A*290202 | | 100 |
| A*3001 | A*3001 | | 100 |
| A*3002 | A*3002 | | 100 |

Capture: Alleles in a same field have the same mini-haplotype profile; grey high lighted are all alleles with identical sequences over exons 2 and 3.

TABLE VIII

| Frequent Alleles of HLA-A | Group of frequent Alleles with same four-digit type | Rare Alleles with same Mini-Haplotype Profile | Resolution (in %) |
|---|---|---|---|
| B*0702 | B*070201, B*070202, B*070203, B*070204 | B*0703, B*0721, B*0722, B*0723, B*0730, B*0733, B*0735 | 98.0 |
| B*0801 | B*0801 | B*0808N, B*0818, B*0819N | 99.3 |
| B*1302 | B*1302 | B*1308 | 99.6 |
| B*1501 | B*15010101, B*15010102N, B*150103, B*150104 | B*1528, B*1533, B*1534, B*1560, B*1575, B*1578, B*1579N, B*1581, B*1582 | 97.6 |
| | B*150102 | | 100 |
| B*1801 | B*180101, B*180102 | B*1805, B*1817N | 99.3 |
| B*3501 | B*350101, B*350102 | B*3507, B*3540N, B*3541, B*3542, B*5305 | 98.7 |
| B*3503 | B*3503 | B*5336 | 99.6 |
| B*4001 | B*400101, B*400102 | B*4011, B*401401, B*401402, B*401403, B*4022N | 98.7 |
| | B*400103 | | 100 |
| | B*400104 | B*4004 | 99.6 |
| B*4402 | B*44020101, B*44020102S, B*440202, B*440203 | B*4411, B*4419N, B*4422, B*4423N, B*4427, B*4433, B*4434, B*4435 | 97.8 |
| B*4403 | B*440301 | B*4413, B*4426, B*4429, B*4430, B*4432, B*4436, B*4437, B*4438, B*4439 | 98.2 |
| | B*440302 | B*4407 | 99.6 |

TABLE VIII-continued

| Frequent Alleles of HLA-A | Group of frequent Alleles with same four-digit type | Rare Alleles with same Mini-Haplotype Profile | Resolution (in %) |
|---|---|---|---|
| B*5101 | B*510101, B*510102, B*510105 | B*5111N, B*5112, B*5114, B*5118, B*5126, B*5127N, B*5128, B*5130, B*5132, B*5133 | 97.6 |
| | B*510103 | | 100 |
| | B*510104 | B*5124 | 99.6 |
| B*5701 | B*570101, B*570102 | B*5706, B*5708 | 99.5 |
| | | | 100 |

Capture: Alleles in a same field have the same mini-haplotype profile; grey high lighted are all alleles with identical sequences over exons 2 and 3.

TABLE IX

| Frequent Alleles of HLA-DRB1* | Group of frequent Alleles with same four-digit type | Rare Alleles with same Mini-Haplotype Profile | Resolution (in %) |
|---|---|---|---|
| DRB1*0101 | DRB1*010101 | DRB1*0105, DRB1*0107, DRB1*0111 | 98.9 |
| | DRB1*010102 | | 100 |
| DRB1*0301 | DRB1*030101, DRB1*030102 | DRB1*0307, DRB1*0312, DRB1*0313, DRB1*0315, DRB1*0316, DRB1*0318, DRB1*0322, DRB1*0323 | 97.2 |
| DRB1*0401 | DRB1*040101, DRB1*040102 | DRB1*0409, DRB1*0426, DRB1*0433 | 98.6 |
| DRB1*0701 | DRB1*070101, DRB1*070102 | DRB1*0703, DRB1*0704, DRB1*0705, DRB1*0707 | 98.3 |
| DRB1*1101 | DRB1*110101, DRB1*110102, DRB1*110103, DRB1*110104, DRB1*110105 | DRB1*112701, DRB1*112702, DRB1*1130, DRB1*1139 | 97.5 |
| DRB1*1104 | DRB1*110401, DRB1*110402 | DRB1*1134, DRB1*1146 | 98.9 |
| DRB1*1302 | DRB1*130201, DRB1*130202 | DRB1*1331, DRB1*1339, DRB1*1341 | 98.6 |
| DRB1*1501 | DRB1*150101, DRB1*150103, DRB1*150105 | DRB1*1503, DRB1*1506, DRB1*1509, DRB1*1513 | 98.0 |
| | DRB1*150102 | | 100 |
| | DRB1*150104 | DRB1*1512 | 99.4 |

Capture: Alleles in a same field have the same mini-haplotype profile; grey high lighted are all alleles with identical sequences over exon 2 (base 101 to 356)

The complete list of HLA alleles and sub-groups generated by the most informative mini-haplotyping markers (ten each for HLA-A, HLA-B and HLA-DRB1) are listed in Tables X to XII below.

TABLE X

| Position cDNA | 4444 9999 5678 | 5555 1111 1234 | 2222 3333 6789 | 55555 7888 9012 | 3333 66677 78901 | 2222 6666 5878 | 2222 5555 6789 | 2222 8999 9012 | 22222 33444 89012 | 2222 7777 0123 |
|---|---|---|---|---|---|---|---|---|---|---|
| A*3008 | TCTA | TGAA | AGTT | CCAG | GGAGT | TGTA | CAGG | ACTG | AGGCC | TGTG |
| A*6806 | TCTA | TGAA | AGTG | CCAG | GGAGT | TGTA | CGGA | ACTG | GGGCC | TGTG |
| A*0244 | TCTA | CCAC | AGCA | CCAC | GGAGT | TGTA | GGGG | ACTC | GGTCC | AGTG |
| A*0254 | TCTA | CCAC | AGCA | CCAC | GGACG | TGTA | GGGG | ACTC | GGTCC | AGTG |
| A*0205 | TCTA | CCAC | AGTG | CCAC | GGAGT | TGTA | GGGG | ACTC | GGTCC | AGTG |
| A*0208 | TCTA | CCAC | AGTG | CCAC | GGAGT | TGTA | GGGG | ACTC | GGTCC | TGTG |
| A*6815 | TCTA | CCAC | AGTG | CCAC | GGAGT | TGTA | CGGA | ACTC | GGGCC | TGTG |
| A*6802 | TCTA | CCAC | AGTG | CCAG | GGAGT | TGTA | CGGA | ACTG | GGGCC | TGTG |
| A*6818N | TCTA | CCAC | AGTG | CCAG | GGAGT | TGTA | CGGA | ACTG | GGGCC | TGTG |

TABLE X-continued

| Position cDNA | 9999 5678 | 4444 1111 3333 1234 | 5555 3333 6789 | 2222 7888 9012 | 55555 66677 78901 | 3333 6666 5878 | 2222 5555 6789 | 2222 8999 9012 | 22222 33444 89012 | 2222 7777 0123 |
|---|---|---|---|---|---|---|---|---|---|---|
| A*0228 | TCTA | CCAC | AGTT | CCAC | GGAGT | TGTA | GGGG | ACTC | AGTCC | AGTG |
| A*0206 | TCTA | CCAC | AGTT | CCAC | GGAGT | TGTA | GGGG | ACTC | GGTCC | AGTG |
| A*0214 | TCTA | CCAC | AGTT | CCAC | GGAGT | TGTA | GGGG | ACTC | GGTCC | AGTG |
| A*0221 | TCTA | CCAC | AGTT | CCAC | GGAGT | TGTA | GGGG | ACTC | GGTCC | AGTG |
| A*0257 | TCTA | CCAC | AGTT | CCAC | GGAGT | TGTA | GGGG | ACTC | GGTCC | AGTG |
| A*0251 | TCTA | CCAC | AGTT | CCAC | GGAGT | TGTA | GGGG | ACTC | GGTCC | AGTG |
| A*0261 | TCTA | CCAC | AGTT | CCAC | GGAGT | TGTA | GGGG | ACTC | GGTGC | AGTG |
| A*0210 | TCTA | CCAC | AGTT | CCAC | GGAGT | TGTT | GGGG | ACTC | GGTCC | AGTG |
| A*6901 | TCTA | CCAC | AGTT | CCAC | GGAGT | TGTA | CGGA | ACTG | GGGCC | TGTG |
| A*2504 | TCTA | CCAG | AGCA | CCAC | GGAGT | TGTA | CGGA | ACTG | GGGCC | TGTG |
| A*2608 | TCTA | CCAG | AGCA | CCAC | GGAGT | TGTA | CGGA | ACTG | GGGCC | TGTG |
| A*2603 | TCTA | CCAG | AGTG | CCAC | GGAGT | TGTA | CGGA | ACTC | GGGCC | TGTG |
| A*2606 | TCTA | CCAG | AGTG | CCAC | GGAGT | TGTA | CGGA | ACTC | GGGCC | TGTG |
| A*2610 | TCTA | CCAG | AGTG | CCAC | GGAGT | TGTA | CGGA | ACTG | GGGCC | TGTG |
| A*2609 | TCTA | CCAG | AGTG | CCAC | GGAGT | TGTA | CGGA | ACTG | GGGCC | TGTG |
| A*250101 | TCTA | CCAG | AGTG | CCAC | GGAGT | TGTA | CGGA | ACTG | GGGCC | TGTG |
| A*250102 | TCTA | CCAG | AGTG | CCAC | GGAGT | TGTA | CGGA | ACTG | GGGCC | TGTG |
| A*2601 | TCTA | CCAG | AGTG | CCAC | GGAGT | TGTA | CGGA | ACTG | GGGCC | TGTG |
| A*2602 | TCTA | CCAG | AGTG | CCAC | GGAGT | TGTA | CGGA | ACTG | GGGCC | TGTG |
| A*2605 | TCTA | CCAG | AGTG | CCAC | GGAGT | TGTA | CGGA | ACTG | GGGCC | TGTG |
| A*2611N | TCTA | CCAG | AGTG | CCAC | GGAGT | TGTA | CGGA | ACTG | GGGCC | TGTG |
| A*2614 | TCTA | CCAG | AGTG | CCAC | GGAGT | TGTA | CGGA | ACTG | GGGCC | TGTG |
| A*2615 | TCTA | CCAG | AGTG | CCAC | GGAGT | TGTA | CGGA | ACTG | GGGCC | TGTG |
| A*2617 | TCTA | CCAG | AGTG | CCAC | GGAGT | TGTA | CGGA | ACTG | GGGCC | TGTG |
| A*2604 | TCTA | CCAG | AGTG | CCAC | GGAGT | TGTA | CGGA | ACTG | GGGCC | TGTG |
| A*6603 | TCTA | CCAG | AGTG | CCAC | GGAGT | TGTA | CGGA | ACTG | GGGCC | TGTG |
| A*2612 | TCTA | CCAG | AGTG | CCAC | GGAGT | TGTA | CGGA | ACTG | GGGCC | TGTG |
| A*2618 | TCTA | CCAG | AGTG | CCAC | GGAGT | TGTA | CGGA | ACTG | GGGCC | TGTG |
| A*4301 | TCTA | CCAG | AGTG | CCAC | GGAGT | TGTA | CTGC | ACTG | GGGCC | TGTG |
| A*260701 | TCTA | CCAG | AGTG | CCAC | GGAGT | TGTA | GGGG | ACTG | GGGCC | AGTG |
| A*260702 | TCTA | CCAG | AGTG | CCAC | GGAGT | TGTA | GGGG | ACTG | GGTCC | AGTG |
| A*2619 | TCTA | CCAG | AGTG | CCAG | GGAGT | TGTA | CAGG | ACTG | AGGCC | TGTG |
| A*3401 | TCTA | CCAG | AGTG | CCAG | GGAGT | TGTA | CGGA | ACTG | GGGCC | AGTG |
| A*3405 | TCTA | CCAG | AGTG | CCAG | GGAGT | TGTA | CGGA | ACTG | GGGCC | AGTG |
| A*6602 | TCTA | CCAG | AGTG | CCAG | GGAGT | TGTA | CGGA | ACTG | GGGCC | TGTG |
| A*2502 | TCTA | CCAG | AGTG | CCAG | GGAGT | TGTA | CGGA | ACTG | GGGCC | TGTG |
| A*2613 | TCTA | CCAG | AGTG | CCAG | GGAGT | TGTA | CGGA | ACTG | GGGCC | TGTG |
| A*6601 | TCTA | CCAG | AGTG | CCAG | GGAGT | TGTA | CGGA | ACTG | GGGCC | TGTG |

TABLE X-continued

| Position cDNA | 9999 5678 | 4444 1111 3333 1234 | 5555 3333 6789 | 2222 7888 9012 | 55555 66677 78901 | 3333 6666 5878 | 2222 5555 6789 | 2222 8999 9012 | 22222 33444 89012 | 2222 7777 0123 |
|---|---|---|---|---|---|---|---|---|---|---|
| A*6604 | TCTA | CCAG | AGTG | CCAG | GGAGT | TGTA | CGGA | ACTG | GGGCC | TGTG |
| A*0241 | TCTA | CCAG | AGTT | CCAC | GGAGT | TGTA | GGGG | ACTC | GGTCC | AGTG |
| A*1106 | TCTA | CCGG | AGCA | CCAG | GGAGT | TGTA | CAGG | ACTC | GGGCC | TGTG |
| A*1103 | TCTA | CCGG | AGCA | CCAG | GGAGT | TGTA | CAGG | ACTG | GGGCC | TGTG |
| A*1104 | TCTA | CCGG | AGCA | CCAG | GGAGT | TGTA | CAGG | ACTG | GGGCC | TGTG |
| A*1107 | TCTA | CCGG | AGCA | CCAG | GGAGT | TGTA | CAGG | ACTG | GGGCC | TGTG |
| A*110101 | TCTA | CCGG | AGCA | CCAG | GGAGT | TGTA | CAGG | ACTG | GGGCC | TGTG |
| A*1110102 | TCTA | CCGG | AGCA | CCAG | GGAGT | TGTA | CAGG | ACTG | GGGCC | TGTG |
| A*1102 | TCTA | CCGG | AGCA | CCAG | GGAGT | TGTA | CAGG | ACTG | GGGCC | TGTG |
| A*1109 | TCTA | CCGG | AGCA | CCAG | GGAGT | TGTA | CAGG | ACTG | GGGCC | TGTG |
| A*1112 | TCTA | CCGG | AGCA | CCAG | GGAGT | TGTA | CAGG | ACTG | GGGCC | TGTG |
| A*1115 | TCTA | CCGG | AGCA | CCAG | GGAGT | TGTA | CAGG | ACTG | GGGCC | TGTG |
| A*1113 | TCTA | CCGG | AGCA | CCAG | GGAGT | TGTA | CAGG | ACTG | GGGCC | TGTG |
| A*1105 | TCTA | CCGG | AGCA | CCAG | GGAGT | TGTA | CAGG | ACTG | GGGCC | TGTG |
| A*1114 | TCTA | CCGG | AGCA | CCAG | GGAGT | TGTA | CAGG | ACTG | GGGCC | TGTG |
| A*1110 | TCTA | CCGG | AGCA | CCAG | GGAGT | TGTA | CGGA | ACTG | GGGCC | TGTG |
| A*6809 | TCTA | CCGG | AGCA | CCAG | GGAGT | TGTA | CGGA | ACTG | GGGCC | TGTG |
| A*1111 | TCTA | CCGG | AGCA | CCAG | GGAGT | TGTA | CTGC | ACTG | GGGCC | TGTG |
| A*1108 | TCTA | CCGG | AGCG | CCAG | GGAGT | TGTA | CAGG | ACTG | GGGCC | TGTG |
| A*6805 | TCTA | CCGG | AGTG | CCAC | GGAGT | TGTA | CGGA | ACTC | GGGCC | TGTG |
| A*6820 | TCTA | CCGG | AGTG | CCAC | GGAGT | TGTA | CGGA | ACTC | GGGCC | TGTG |
| A*680301 | TCTA | CCGG | AGTG | CCAC | GGAGT | TGTA | CGGA | ACTG | GGGCC | TGTG |
| A*680302 | TCTA | CCGG | AGTG | CCAC | GGAGT | TGTA | CGGA | ACTG | GGGCC | TGTG |
| A*6804 | TCTA | CCGG | AGTG | CCAC | GGAGT | TGTA | CGGA | ACTG | GGGCC | TGTG |
| A*680101 | TCTA | CCGG | AGTG | CCAG | GGAGT | TGTA | CGGA | ACTG | GGGCC | TGTG |
| A*680102 | TCTA | CCGG | AGTG | CCAG | GGAGT | TGTA | CGGA | ACTG | GGGCC | TGTG |
| A*680103 | TCTA | CCGG | AGTG | CCAG | GGAGT | TGTA | CGGA | ACTG | GGGCC | TGTG |
| A*6807 | TCTA | CCGG | AGTG | CCAG | GGAGT | TGTA | CGGA | ACTG | GGGCC | TGTG |
| A*6811N | TCTA | CCGG | AGTG | CCAG | GGAGT | TGTA | CGGA | ACTG | GGGCC | TGTG |
| A*6812 | TCTA | CCGG | AGTG | CCAG | GGAGT | TGTA | CGGA | ACTG | GGGCC | TGTG |
| A*6817 | TCTA | CCGG | AGTG | CCAG | GGAGT | TGTA | CGGA | ACTG | GGGCC | TGTG |
| A*6819 | TCTA | CCGG | AGTG | CCAG | GGAGT | TGTA | CGGA | ACTG | GGGCC | TGTG |
| A*6821 | TCTA | CCGG | AGTG | CCAG | GGAGT | TGTA | CGGA | ACTG | GGGCC | TGTG |
| A*6822 | TCTA | CCGG | AGTG | CCAG | GGAGT | TGTA | CGGA | ACTG | GGGCC | TGTG |
| A*6823 | TCTA | CCGG | AGTG | CCAG | GGAGT | TGTA | CGGA | ACTG | GGGCC | TGTG |
| A*6824 | TCTA | CCGG | AGTG | CCAG | GGAGT | TGTA | CGGA | ACTG | GGGCC | TGTG |
| A*6816 | TCTA | CCGG | AGTG | CCAG | GGAGT | TGTA | CGGA | ACTG | GGGCC | TGTG |
| A*6813 | TCTA | CCGG | AGTG | CCAG | GGAGT | TGTA | CGGG | ACTG | GGGCC | TGTG |

TABLE X-continued

| Position cDNA | 9999 5678 | 4444 1111 1234 | 5555 3333 6789 | 2222 7888 9012 | 55555 66677 78901 | 3333 6666 5878 | 2222 5555 6789 | 2222 8999 9012 | 22222 33444 89012 | 2222 7777 0123 |
|---|---|---|---|---|---|---|---|---|---|---|
| A*6810 | TCTA | CCGG | AGTG | CCAG | GGAGT | TGTA | GAGG | ACTG | GGGCC | TGTG |
| A*6814 | TCTA | CCGG | AGTG | CCAG | GGAGT | TGTA | GAGG | ACTG | GGGCC | TGTG |
| A*6808 | TCTA | CCGG | AGCT | CCAG | GGAGT | TGTA | CGGA | ACTG | GGGCC | TGTG |
| A*0312 | TCTA | CCGG | AGTT | CCAG | GGAGT | TGTA | CAGG | ACTG | GGGCC | TGTG |
| A*3402 | TCTA | CCGG | AGTT | CCAG | GGAGT | TGTA | CGGA | ACTG | GGGCC | TGTG |
| A*3403 | TCTA | CCGG | AGTT | CCAG | GGAGT | TGTA | CGGA | ACTG | GGGCC | TGTG |
| A*3404 | TCTA | CCGG | AGTT | CCAG | GGAGT | TGTA | CGGA | ACTG | AGGCC | TGTG |
| A*3102 | TCAC | CCAG | AGTT | CCAC | GGAGT | TGTA | CAGG | ACTG | AGGCC | AGTG |
| A*3107 | TCAC | CCAG | AGTT | CCAC | GGAGT | TGTA | CAGG | ACTG | AGGCC | AGTG |
| A*3108 | TCAC | CCAG | AGTT | CCAC | GGAGT | TGTA | GAGG | ACTG | GGGCC | AGTG |
| A*3105 | TCAC | CCAG | AGTT | CCAC | GGACG | TGTA | CAGG | ATTG | AGGCC | TGTG |
| A*310102 | TCAC | CCAG | AGTT | CCAC | GGAGT | TGTA | CAGG | ATTG | AGGCC | TGTG |
| A*3109 | TCAC | CCAG | AGTT | CCAC | GGAGT | TGTA | CAGG | ATTG | AGGCC | TGTG |
| A*3301 | TCAC | CCAG | AGTT | CCAC | GGAGT | TGTA | CGGA | ATTG | GGGCC | TGTG |
| A*330301 | TCAC | CCAG | AGTT | CCAC | GGAGT | TGTA | CGGA | ATTG | GGGCC | TGTG |
| A*330302 | TCAC | CCAG | AGTT | CCAC | GGAGT | TGTA | CGGA | ATTG | GGGCC | TGTG |
| A*3304 | TCAC | CCAG | AGTT | CCAC | GGAGT | TGTA | CGGA | ATTG | GGGCC | TGTG |
| A*3305 | TCAC | CCAG | AGTT | CCAC | GGAGT | TGTA | CGGA | ATTG | GGGCC | TGTG |
| A*3306 | TCAC | CCAG | AGTT | CCAC | GGAGT | TGTA | CGGA | ATTG | GGGCC | TGTG |
| A*3307 | TCAC | CCAG | AGTT | CCAC | GGAGT | TGTA | CGGA | ATTG | GGGCC | TGTG |
| A*2905 | TCAC | CCGG | AGCA | CCAG | GGAGT | TGTA | CTGC | ACTG | GGGCC | TGTG |
| A*2903 | TCAC | CCGG | AGTT | CCAG | GGACG | TGTA | CTGC | ACTG | GGGCC | TGTG |
| A*290202 | TCAC | CCGG | AGTT | CCAG | GGAGT | TGTA | CTGC | ACTG | GGGCC | TGTG |
| A*290101 | TCAC | CCGG | AGTT | CCAG | GGAGT | TGTA | CTGC | ACTG | GGGCC | TGTG |
| A*290101 | TCAC | CCGG | AGTT | CCAG | GGAGT | TGTA | CTGC | ACTG | GGGCC | TGTG |
| A*290201 | TCAC | CCGG | AGTT | CCAG | GGAGT | TGTA | CTGC | ACTG | GGGCC | TGTG |
| A*2906 | TCAC | CCGG | AGTT | CCAG | GGAGT | TGTA | CTGC | ACTG | GGGCC | TGTG |
| A*2908N | TCAC | CCGG | AGTT | CCAG | GGAGT | TGTA | CTGC | ACTG | GGGCC | TGTG |
| A*2904 | TCAC | CCGG | AGTT | CCAG | GGAGT | TGTA | CTGC | ACTG | GGGCC | TGTG |
| A*2909 | TCAC | CCGG | AGTT | CCAG | GGAGT | TGTA | CTGC | ACTG | GGGCC | TGTG |
| A*2907 | TCAC | CCGG | AGTT | CCAG | GGAGT | TGTA | CTGC | ACTG | GGGCC | TGTG |
| A*3103 | TCAC | CCGG | AGTT | CCAC | GGAGT | TGTA | CAGG | ATTG | AGGCC | TGTG |
| A*3104 | TCAC | CCGG | AGTT | CCAC | GGAGT | TGTA | CAGG | ATTG | AGGCC | TGTG |
| A*3106 | TCAC | CCGG | AGTT | CCAC | GGAGT | TGTA | CAGG | ATTG | AGGCC | TGTG |
| A*3004 | TCTC | TGAA | AGTG | CCAC | GGAGT | TGTA | CAGG | ACTG | AGGCC | TGTG |
| A*3006 | TCTC | TGAA | AGTG | CCAC | GGAGT | TGTA | CAGG | ACTG | AGGCC | TGTG |
| A*3010 | TCTC | TGAA | AGTT | CCAC | GGAGT | TGCA | CAGG | ACTG | AGGCC | TGTG |
| A*3007 | TCTC | TGAA | AGTT | CCAC | GGAGT | TGTA | GAGG | ACTG | AGGCC | AGTG |

TABLE X-continued

| Position cDNA | 9999 5678 | 4444 1111 1234 | 5555 3333 6789 | 2222 7888 9012 | 55555 66677 78901 | 3333 6666 5878 | 2222 5555 6789 | 2222 8999 9012 | 22222 33444 89012 | 2222 7777 0123 |
|---|---|---|---|---|---|---|---|---|---|---|
| A*3002 | TCTC | TGAA | AGTT | CCAC | GGAGT | TGTA | CAGG | ACTG | AGGCC | TGTG |
| A*3009 | TCTC | TGAA | AGTT | CCAC | GGAGT | TGTA | CAGG | ACTG | AGGCC | TGTG |
| A*3012 | TCTC | TGAA | AGTT | CCAC | GGAGT | TGTA | CAGG | ACTG | AGGCC | TGTG |
| A*3003 | TCTC | TGAA | AGTT | CCAC | GGAGT | TGTA | CAGG | ACTG | GGGCC | TGTG |
| A*3001 | TCTC | TGAA | AGTT | CCAG | GGAGT | TGTA | CAGG | ACTG | AGGCC | TGTG |
| A*3011 | TCTC | TGAA | AGTT | CCAG | GGAGT | TGTA | CAGG | ACTG | GGGCC | TGTG |
| A*2414 | TCTC | CCAC | AGCA | CCAC | GGACG | TGTA | GAGG | ACTG | GGGCC | AGTG |
| A*2415 | TCTC | CCAC | AGCA | CCAC | GGACG | TGTA | GAGG | ACTG | GGGCC | AGTG |
| A*2428 | TCTC | CCAC | AGCA | CCAC | GGACG | TGTT | GAGG | ACTG | GGGCC | AGTG |
| A*2430 | TCTC | CCAC | AGCA | CCAC | GGACG | TGTT | GAGG | ACTG | GGGCC | AGTG |
| A*2408 | TCTC | CCAC | AGCA | CCAC | GGACG | TGTT | GGGG | ACTG | GGGCC | AGTG |
| A*2431 | TCTC | CCAC | AGCA | CCAC | GGACG | TGTT | GAGC | ACTG | GGGCC | AGTG |
| A*2420 | TCTC | CCAC | AGCA | CCAC | GGACG | TGTT | GAGG | ACTG | GGGCC | AGTG |
| A*2429 | TCTC | CCAC | AGCA | CCAC | GGACG | TGTT | GAGG | ACTG | GGGCC | AGTG |
| A*240201 | TCTC | CCAC | AGCA | CCAC | GGACG | TGTT | GAGG | ACTG | GGGCC | AGTG |
| A*240201 | TCTC | CCAC | AGCA | CCAC | GGACG | TGTT | GAGG | ACTG | GGGCC | AGTG |
| A*240202 | TCTC | CCAC | AGCA | CCAC | GGACG | TGTT | GAGG | ACTG | GGGCC | AGTG |
| A*240203 | TCTC | CCAC | AGCA | CCAC | GGACG | TGTT | GAGG | ACTG | GGGCC | AGTG |
| A*240204 | TCTC | CCAC | AGCA | CCAC | GGACG | TGTT | GAGG | ACTG | GGGCC | AGTG |
| A*2404 | TCTC | CCAC | AGCA | CCAC | GGACG | TGTT | GAGG | ACTG | GGGCC | AGTG |
| A*2409N | TCTC | CCAC | AGCA | CCAC | GGACG | TGTT | GAGG | ACTG | GGGCC | AGTG |
| A*2411N | TCTC | CCAC | AGCA | CCAC | GGACG | TGTT | GAGG | ACTG | GGGCC | AGTG |
| A*2426 | TCTC | CCAC | AGCA | CCAC | GGACG | TGTT | GAGG | ACTG | GGGCC | AGTG |
| A*2427 | TCTC | CCAC | AGCA | CCAC | GGACG | TGTT | GAGG | ACTG | GGGCC | AGTG |
| A*2432 | TCTC | CCAC | AGCA | CCAC | GGACG | TGTT | GAGG | ACTG | GGGCC | AGTG |
| A*2435 | TCTC | CCAC | AGCA | CCAC | GGACG | TGTT | GAGG | ACTG | GGGCC | AGTG |
| A*2436N | TCTC | CCAC | AGCA | CCAC | GGACG | TGTT | GAGG | ACTG | GGGCC | AGTG |
| A*2437 | TCTC | CCAC | AGCA | CCAC | GGACG | 'TGTT | GAGG | ACTG | GGGCC | AGTG |
| A*2432 | TCTC | CCAC | AGCA | CCAC | GGACG | TGTT | GAGG | ACTG | GGGCC | AGTG |
| A*2435 | TCTC | CCAC | AGCA | CCAC | GGACG | TGTT | GAGG | ACTG | GGGCC | AGTG |
| A*2436N | TCTC | CCAC | AGCA | CCAC | GGACG | TGTT | GAGG | ACTG | GGGCC | AGTG |
| A*2437 | TCTC | CCAC | AGCA | CCAC | GGACG | TGTT | GAGG | ACTG | GGGCC | AGTG |
| A*2438 | TCTC | CCAC | AGCA | CCAC | GGACG | TGTT | GAGG | ACTG | GGGCC | AGTG |
| A*2439 | TCTC | CCAC | AGCA | CCAC | GGACG | TGTT | GAGG | ACTG | GGGCC | AGTG |
| A*2421 | TCTC | CCAC | AGCA | CCAC | GGACG | TGTT | GAGG | ACTG | GGGCC | AGTG |
| A*2425 | TCTC | CCAC | AGCA | CCAC | GGACG | TGTT | GAGG | ACTG | GGGCC | AGTG |
| A*2405 | TCTC | CCAC | AGCA | CCAC | GGACG | TGTT | GAGG | ACTG | GGGCC | AGTG |
| A*2434 | TCTC | CCAC | AGCA | CCAC | GGACG | TGTT | GAGG | ATTG | GGGCC | AGTG |

TABLE X-continued

| Position cDNA | 9999 5678 | 4444 1111 1234 | 5555 3333 6789 | 2222 7888 9012 | 55555 66677 78901 | 3333 6666 5878 | 2222 5555 6789 | 2222 8999 9012 | 22222 33444 89012 | 2222 7777 0123 |
|---|---|---|---|---|---|---|---|---|---|---|
| A*2407 | TCTC | CCAC | AGCA | CCAG | GGACG | TGTT | GAGG | ACTG | GGGCC | AGTG |
| A*2419 | TCTC | CCAC | AGCA | CCAG | GGACG | TGTT | GAGG | ACTG | GGGCC | AGTG |
| A*2423 | TCTC | CCAC | AGCA | CCAC | GGACT | TGTT | GAGG | ACTG | GGGCC | AGTG |
| A*240301 | TCTC | CCAC | AGCA | CCAC | GGACT | TGTT | GAGG | ACTG | GGGCC | AGTG |
| A*240302 | TCTC | CCAC | AGCA | CCAC | GGACT | TGTT | GAGG | ACTG | GGGCC | AGTG |
| A*2433 | TCTC | CCAC | AGCA | CCAC | GGACT | TGTT | GAGG | ACTG | GGGCC | AGTG |
| A*2410 | TCTC | CCAC | AGCA | CCAC | GGACT | TGTT | GAGG | ACTG | GGGCC | AGTG |
| A*2302 | TCTC | CCAC | AGTG | CCAC | GGACG | TGTT | GAGG | ACTG | GGGCC | AGTG |
| A*2406 | TCTC | CCAC | AGTG | CCAC | GGACG | TGTT | GAGG | ACTG | GGGCC | AGTG |
| A*2422 | TCTC | CCAC | AGTG | CCAC | GGACT | TGTT | GAGG | ACTG | GGGCC | AGTG |
| A*2301 | TCTC | CCAC | AGTT | CCAC | GGACG | TGTT | GAGG | ACTG | GGGCC | AGTG |
| A*2306 | TCTC | CCAC | ACTT | CCAC | GGACG | TGTT | GAGG | ACTG | GGGCC | AGTG |
| A*2307N | TCTC | CCAC | AGTT | CCAC | GGACG | TGTT | GAGG | ACTG | GGGCC | AGTG |
| A*2308N | TCTC | CCAC | AGTT | CCAC | GGACG | TGTT | GAGG | ACTG | GGGCC | AGTG |
| A*2305 | TCTC | CCAC | AGTT | CCAC | GGACG. | TGTT | GAGG | ACTG | GGGCC | AGTG |
| A*2310 | TCTC | CCAC | ACTT | CCAC | GGACG | TGTT | GAGG | ACTG | GGGCC | AGTG |
| A*2413 | TCTC | CCAC | AGTT | CCAC | GGACG | TGTT | GAGG | ACTG | GGGCC | AGTG |
| A*2303 | TCTC | CCAC | AGTT | CCAC | GGACG | TGTT | GAGG | ACTG | GGGCC | AGTG |
| A*2309 | TCTC | CCAC | AGTT | CCAC | GGACG | TGTT | CAGG | ACTG | GGGCC | TGTG |
| A*2304 | TCTC | CCAC | AGTT | CCAC | GGACT | TGTT | GAGG | ACTG | GGGCC | AGTG |
| A*2418 | TCTC | CCAC | AGTT | CCAC | GGACT | TGTT | GAGG | ACTG | GGGCC | AGTG |
| A*2424 | TCTC | CCAC | AGTT | CCAG | GGACG | TGTT | CGGA | ACTG | GGGCC | TGTG |
| A*2616 | TCTC | CCAG | AGTG | CCAC | GGAGT | TGTA | CGGA | ACTG | GGGCC | TGTG |
| A*3207 | TCTC | CCAG | AGTT | CCAC | GGAGT | TGTA | CAGG | ACTG | GGGCC | TGTG |
| A*0102 | TCTC | CCGG | AGCG | CCAC | GGACG | TGTA | CAGG | ACTG | GGGCC | TATG |
| A*2417 | TCTC | CCGG | AGCA | CCAC | GGACG | TGTT | CAGG | ACTG | GGGCC | AGTG |
| A*0252 | TCTC | TGAA | AGTT | CCAC | GGAGT | TGTA | GGGG | ACTC | GGTCC | AGTG |
| A*0219 | TCTT | CCAC | AGCA | CCAC | GGACG | TGTA | GGGG | ACTC | GGTCC | AGTG |
| A*0237 | TCTT | CCAC | AGCA | CCAC | GGACG | TGTA | GGGG | ACTC | GGTCC | AGTG |
| A*0213 | TCTT | CCAC | AGCA | CCAC | GGAGT | TGTA | GGGG | ACTC | GGTCC | AGTG |
| A*0238 | TCTT | CCAC | AGCA | CCAC | GGAGT | TGTA | GGGG | ACTC | GGTCC | AGTG |
| A*0227 | TCTT | CCAC | AGCA | CCAC | GGAGT | TGTA | GGGG | ACTC | GGTCC | AGTG |
| A*0212 | TCTT | CCAC | AGCA | CCAC | GGAGT | TGTA | GGGG | ACTC | GGTCC | AGTG |
| A*0249 | TCTT | CCAC | AGCG | CCAC | GGAGT | TGTA | GGGG | ACTC | GGTCC | AGTG |
| A*0250 | TCTT | CCAC | AGTG | CCAC | GGAGT | TGTA | GGGG | ACTC | GGGCC | AGTG |
| A*0203 | TCTT | CCAC | AGTG | CCAC | GGAGT | TGTA | GGGG | ACTC | GGTCC | AGTG |
| A*0202 | TCTT | CCAC | AGTG | CCAC | GGAGT | TGTA | GGGG | ACTC | GGTCC | AGTG |
| A*0222 | TCTT | CCAC | AGTG | CCAC | GGAGT | TGTA | GGGG | ACTC | GGTCC | AGTG |

TABLE X-continued

| Position cDNA | 9999 5678 | 4444 1111 1234 | 5555 3333 6789 | 2222 7888 9012 | 55555 66677 78901 | 3333 6666 5878 | 2222 5555 6789 | 2222 8999 9012 | 22222 33444 89012 | 2222 7777 0123 |
|---|---|---|---|---|---|---|---|---|---|---|
| A*0263 | TCTT | CCAC | AGTG | CCAC | GGAGT | TGTA | GGGG | ACTC | GGTCC | AGTG |
| A*0247 | TCTT | CCAC | AGTG | CCAC | GGAGT | TGTA | GGGG | AGTC | GGTCC | AGTG |
| A*0236 | TCTT | CCAC | AGTT | CCAC | GGACG | TGTA | GGGG | ACTC | GGGCC | AGTG |
| A*0245 | TCTT | CCAC | AGTT | CCAC | GGAGT | TGTA | CAGG | ACTC | GGTCC | AGTG |
| A*0246 | TCTT | CCAC | AGTT | CCAC | GGAGT | TGTA | GAGG | ACTC | GGTCC | AGTG |
| A*0248 | TCTT | CCAC | AGTT | CCAC | GGAGT | TGTA | GAGG | ACTG | GGGCC | AGTG |
| A*0255 | TCTT | CCAC | AGTT | CCAC | GGAGT | TGTA | CGGA | ACTC | GGGCC | TGTG |
| A*020105 | TCTT | CCAC | AGTT | CCAC | GGAGT | TGTA | GGGG | ACTC | GGTCC | |
| A*0226 | TCTT | CCAC | AGTT | CCAC | GGAGT | TGTA | GGGG | ACTC | GGTCC | AGTG |
| A*0259 | TCTT | CCAC | AGTT | CCAC | GGAGT | TGTA | GGGG | ACTC | GGTCC | AGTG |
| A*020106 | TCTT | CCAC | AGTT | CCAC | GGAGT | TGTA | GGGG | ACTC | GGTCC | AGTG |
| A*020101 | TCTT | CCAC | AGTT | CCAC | GGAGT | TGTA | GGGG | ACTC | GGTCC | AGTG |
| A*020101 | TCTT | CCAC | AGTT | CCAC | GGAGT | TGTA | GGGG | ACTC | GGTCC | AGTG |
| A*020102 | TCTT | CCAC | AGTT | CCAC | GGAGT | TGTA | GGGG | ACTC | GGTCC | AGTG |
| A*020103 | TCTT | CCAC | AGTT | CCAC | GGAGT | TGTA | GGGG | ACTC | GGTCC | AGTG |
| A*020104 | TCTT | CCAC | AGTT | CCAC | GGAGT | TGTA | GGGG | ACTC | GGTCC | AGTG |
| A*020108 | TCTT | CCAC | AGTT | CCAC | GGAGT | TGTA | GGGG | ACTC | GGTCC | AGTG |
| A*020109 | TCTT | CCAC | AGTT | CCAC | GGAGT | TGTA | GGGG | ACTC | GGTCC | AGTG |
| A*0204 | TCTT | CCAC | AGTT | CCAC | GGAGT | TGTA | GGGG | ACTC | GGTCC | AGTG |
| A*0209 | TCTT | CCAC | AGTT | CCAC | GGAGT | TGTA | GGGG | ACTC | GGTCC | AGTG |
| A*0225 | TCTT | CCAC | AGTT | CCAC | GGAGT | TGTA | GGGG | ACTC | GGTCC | AGTG |
| A*0231 | TCTT | CCAC | AGTT | CCAC | GGAGT | TGTA | GGGG | ACTC | GGTCC | AGTG |
| A*0232N | TCTT | CCAC | AGTT | CCAC | GGAGT | TGTA | GGGG | ACTC | GGTCC | AGTG |
| A*0242 | TCTT | CCAC | AGTT | CCAC | GGAGT | TGTA | GGGG | ACTC | GGTCC | AGTG |
| A*0243N | TCTT | CCAC | AGTT | CCAC | GGAGT | TGTA | GGGG | ACTC | GGTCC | AGTG |
| A*0253N | TCTT | CCAC | AGTT | CCAC | GGAGT | TGTA | GGGG | ACTC | GGTCC | AGTG |
| A*0258 | TCTT | CCAC | AGTT | CCAC | GGAGT | TGTA | GGGG | ACTC | GGTCC | AGTG |
| A*0260 | TCTT | CCAC | AGTT | CCAC | GGAGT | TGTA | GGGG | ACTC | GGTCC | AGTG |
| A*0264 | TCTT | CCAC | AGTT | CCAC | GGAGT | TGTA | GGGG | ACTC | GGTCC | AGTG |
| A*0266 | TCTT | CCAC | AGTT | CCAC | GGAGT | TGTA | GGGG | ACTC | GGTCC | AGTG |
| A*0267 | TCTT | CCAC | AGTT | CCAC | GGAGT | TGTA | GGGG | ACTC | GGTCC | AGTG |
| A*020107 | TCTT | CCAC | AGTT | CCAC | GGAGT | TGTA | GGGG | ACTC | GGTCC | AGTG |
| A*0216 | TCTT | CCAC | AGTT | CCAC | GGAGT | TGTA | GGGG | ACTC | GGTCC | AGTG |
| A*0229 | TCTT | CCAC | AGTT | CCAC | GGAGT | TGTA | GGGG | ACTC | GGTCC | AGTG |
| A*0230 | TCTT | CCAC | AGTT | CCAC | GGAGT | TGTA | GGGG | ACTC | GGTCC | AGTG |
| A*0240 | TCTT | CCAC | AGTT | CCAC | GGAGT | TGTA | GGGG | ACTC | GGTCC | AGTG |
| A*0224 | TCTT | CCAC | AGTT | CCAC | GGAGT | TGTA | GGGG | ACTC | GGTCC | AGTG |
| A*022002 | TCTT | CCAC | AGTT | CCAC | GGAGT | TGTA | GGGG | ACTC | GGTCC | CGTG |

TABLE X-continued

| Position cDNA | 9999 5678 | 4444 1111 1234 | 5555 3333 6789 | 2222 7888 9012 | 55555 66677 78901 | 3333 6666 5878 | 2222 5555 6789 | 2222 8999 9012 | 22222 33444 89012 | 2222 7777 0123 |
|---|---|---|---|---|---|---|---|---|---|---|
| A*022001 | TCTT | CCAC | AGTT | CCAC | GGAGT | TGTA | GGGG | ACTC | GGTCC | TGTG |
| A*0211 | TCTT | CCAC | AGTT | CCAC | GGAGT | TGTA | GGGG | ATTG | GGTCC | AGTG |
| A*0233 | TCTT | CCAC | AGTT | CCAC | GGAGT | TGTC | GGGG | ACTC | GGTCC | AGTG |
| A*0207 | TCTT | CCAC | AGTT | CCAC | GGAGT | TGTG | GGGG | ACTC | GGTCC | AGTG |
| A*0215N | TCTT | CCAC | AGTT | CCAC | GGAGT | TGTG | GGGG | ACTC | GGTCC | AGTG |
| A*0218 | TCTT | CCAC | AGTT | CCAC | GGAGT | TGTG | GGGG | ACTC | GGTCC | AGTG |
| A*021701 | TCTT | CCAC | AGTT | CCAC | GGAGT | TGTT | GGGG | ACTC | GGTCC | AGTG |
| A*021702 | TCTT | CCAC | AGTT | CCAC | GGAGT | TGTT | GGGG | ACTC | GGTCC | AGTG |
| A*0239 | TCTT | CCAC | AGTT | CCAC | GGAGT | TGTT | GGGG | ACTC | GGTCC | AGTG |
| A*0256 | TCTT | CCAC | AGTT | CCAG | GGAGT | TGTA | CAGG | ACTC | GGTCC | TGTG |
| A*0234 | TCTT | CCAC | AGTT | CCAG | GGAGT | TGTA | GGGG | ACTC | GGTCC | AGTG |
| A*0262 | TCTT | CCAC | AGTT | CCAG | GGAGT | TGTA | GGGG | ACTC | GGTCC | TGTG |
| A*0235 | TCTT | CCAC | AGTT | CCAG | GGAGT | TGTA | GGGG | ACTG | GGTCC | AGTG |
| A*3202 | TCTT | CCAG | AGCA | CCAC | GGAGT | TGTA | CAGG | ACTG | GGGCC | TGTG |
| A*2503 | TCTT | CCAG | AGTG | CCAC | GGAGT | TGTA | CGGA | ACTG | GGGCC | TGTG |
| A*7406 | TCTT | CCAG | AGTT | CCAC | GGAGT | TGTA | CAGG | ACTC | GGGCC | TGTG |
| A*3205 | TCTT | CCAG | AGTT | CCAC | GGAGT | TGTA | CAGG | ACTG | GGGCC | AGTG |
| A*3206 | TCTT | CCAG | AGTT | CCAC | GGAGT | TGTA | CAGG | ACTG | GGGCC | TGTG |
| A*3201 | TCTT | CCAG | AGTT | CCAC | GGAGT | TGTA | CAGG | ACTG | GGGCC | TGTG |
| A*3203 | TCTT | CCAG | AGTT | CCAC | GGAGT | TGTA | CAGG | ACTG | GGGCC | TGTG |
| A*7401 | TCTT | CCAG | AGTT | CCAC | GGAGT | TGTA | CAGG | ACTG | GGGCC | TGTG |
| A*7402 | TCTT | CCAG | AGTT | CCAC | GGAGT | TGTA | CAGG | ACTG | GGGCC | TGTG |
| A*7403 | TCTT | CCAG | AGTT | CCAC | GGAGT | TGTA | CAGG | ACTG | GGGCC | TGTG |
| A*7408 | TCTT | CCAG | AGTT | CCAC | GGAGT | TGTA | CAGG | ACTG | GGGCC | TGTG |
| A*7409 | TCTT | CCAG | AGTT | CCAC | GGAGT | TGTA | CAGG | ACTG | GGGCC | TGTG |
| A*7405 | TCTT | CCAG | AGTT | CCAC | GGAGT | TGTA | CAGG | GCTG | GGGCC | TGTG |
| A*7407 | TCTT | CCAG | AGTT | CCAC | GGAGT | TGTA | CAGG | ATTG | GGGCC | TGTG |
| A*0265 | TCTT | CCAG | AGTT | CCAC | GGAGT | TGTA | GGGG | ACTC | GGTCC | AGTG |
| A*7404 | TCTT | CCAG | AGTT | CCAC | GGAGT | TGTA | GGGG | ACTG | GGTCC | AGTG |
| A*0302 | TCTT | CCGG | AGCA | CCAG | GGAGT | TGTA | CAGG | ACTG | GGGCC | TGTG |
| A*0310 | TCTT | CCGG | AGCA | CCAG | GGAGT | TGTA | CAGG | ACTG | GGGCC | TGTG |
| A*0107 | TCTT | CCGG | AGCG | CCAC | GGACG | TGTA | CAGG | ACTG | AGGCC | TGTG |
| A*010101 | TCTT | CCGG | AGCG | CCAC | GGACG | TGTA | CAGG | ACTG | GGGCC | TATG |
| A*010102 | TCTT | CCGG | AGCG | CCAC | GGACG | TGTA | CAGG | ACTG | GGGCC | TATG |
| A*0103 | TCTT | CCGG | AGCG | CCAC | GGACG | TGTA | CAGG | ACTG | GGGCC | TATG |
| A*0104N | TCTT | CCGG | AGCG | CCAC | GGACG | TGTA | CAGG | ACTG | GGGCC | TATG |
| A*0108 | TCTT | CCGG | AGCG | CCAC | GGACG | TGTA | CAGG | ACTG | GGGCC | TATG |
| A*0109 | TCTT | CCGG | AGCG | CCAC | GGACG | TGTA | CAGG | ACTG | GGGCC | TATG |

TABLE X-continued

| Position cDNA | 4444<br>9999<br>5678 | 5555<br>1111<br>1234 | 2222<br>3333<br>6789 | 55555<br>7888<br>9012 | 3333<br>66677<br>78901 | 2222<br>6666<br>5878 | 2222<br>5555<br>6789 | 22222<br>8999<br>9012 | 2222<br>33444<br>89012 | 2222<br>7777<br>0123 |
|---|---|---|---|---|---|---|---|---|---|---|
| A*3601 | TCTT | CCGG | AGCG | CCAC | GGAGT | TGTA | CAGG | ACTG | GGGCC | TATG |
| A*3602 | TCTT | CCGG | AGCG | CCAC | GGAGT | TGTA | CAGG | ACTG | GGGCC | TATG |
| A*3603 | TCTT | CCGG | AGCG | CCAC | GGAGT | TGTA | CAGG | ACTG | GGGCC | TATG |
| A*3604 | TCTT | CCGG | AGCG | CCAC | GGAGT | TGTA | CAGG | ACTG | GGGCC | TATG |
| A*030102 | TCTT | CCGG | AGCT | CCAG | GGAGT | TGTA | CAGG | ACTG | GGGCC | TGTG |
| A*8001 | TCTT | CCGG | AGCT | CCAC | GGACG | TGTA | GAGG | ACTA | GAGCC | TGTG |
| A*0106 | TCTT | CCGG | AGTT | CCAC | GGACG | TGTA | CAGG | ACTG | GGGCC | TATG |
| A*0308 | TCTT | CCGG | AGTT | CCAC | GGAGT | TGTA | CAGG | ACTG | GGGCC | TGTG |
| A*3204 | TCTT | CCGG | AGTT | CCAC | GGAGT | TGTA | CAGG | ACTG | GGGCC | TGTG |
| A*0309 | TCTT | CCGG | AGTT | CCAG | GGAGT | TGTA | CAGG | ACTC | GGGCC | TGTG |
| A*030101 | TCTT | CCGG | AGTT | CCAG | GGAGT | TGTA | CAGG | ACTG | GGGCC | TGTG |
| A*030101 | TCTT | CCGG | AGTT | CCAG | GGAGT | TGTA | CAGG | ACTG | GGGCC | TGTG |
| A*0303N | TCTT | CCGG | AGTT | CCAG | GGAGT | TGTA | CAGG | ACTG | GGGCC | TGTG |
| A*0304 | TCTT | CCGG | AGTT | CCAG | GGAGT | TGTA | CAGG | ACTG | GGGCC | TGTG |
| A*0305 | TCTT | CCGG | AGTT | CCAG | GGAGT | TGTA | CAGG | ACTG | GGGCC | TGTG |
| A*0306 | TCTT | CCGG | AGTT | CCAG | GGAGT | TGTA | CAGG | ACTG | GGGCC | TGTG |
| A*0311N | TCTT | CCGG | AGTT | CCAG | GGAGT | TGTA | CAGG | ACTG | GGGCC | TGTG |
| A*0307 | TCTT | CCGG | AGTT | CCAG | GGAGT | TGTA | CAGG | ACTG | GGGCC | TGTG |
| A*030103 | TCTT | CCGG | AGTT | CCAG | GGAGT | TGTA | CAGG | ACTG | GGTCC | TGTG |

TABLE XI

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-0804 | AGGA | ACGCC | ACGT | GCATA | TCTC | CAGAG | GAGAG | CATG | GAGA | GTAC |
| B-0817 | AGGA | ACGCC | ACGT | GCATA | TCTC | CAGAG | GAGAA | CATG | GAGA | GTAC |
| B-4102 | AGGA | ACGCC | ACGT | GCATA | TCTC | CAGAG | GAGAG | CATG | GGAA | GTAC |
| B-4103 | AGGA | ACGCC | ACGT | GCATA | TCTC | CAGAG | GAGAG | GATG | GGAA | GTAC |
| B-4101 | AGGA | ACGCC | ACGT | GCATA | TCTC | CAGAG | GAGAG | GATG | GGAA | GTAT |
| B-4105 | AGGA | ACGCC | ACGT | GCATA | TCTC | CAGAG | GAGAG | GATG | GGAA | GTAT |
| B-4106 | AGGA | ACGCC | ACGT | GCATA | TCTC | CAGAG | GAGAG | GATG | GGAA | GTAT |
| B-0805 | AGGA | ACGCC | ACGT | GCATA | CCTT | CAGAG | GAGAG | CATG | GAGA | GTAC |
| B-0809 | AGGA | ACGCC | ACGT | GCATA | TCTT | CAGAC | GAGAG | GATG | GAGA | GTAT |
| B-0802 | AGGA | ACGCC | ACGT | GCATA | TCTT | CAGAG | GAGAA | CATG | GAGA | GTAC |
| B-0803 | AGGA | ACGCC | ACGT | GCATA | TCTT | CAGAG | GAGAA | CATG | GAGA | GTAC |
| B-0801 | AGGA | ACGCC | ACGT | GCATA | TCTT | CAGAG | GAGAG | CATG | GAGA | GTAC |
| B-0808N | AGGA | ACGCC | ACGT | GCATA | TCTT | CAGAG | GAGAG | CATG | GAGA | GTAC |
| B-0810 | AGGA | ACGCC | ACGT | GCATA | TCTT | CAGAG | GAGAG | CATG | GAGA | GTAC |
| B-0818 | AGGA | ACGCC | ACGT | GCATA | TCTT | CAGAG | GAGAG | CATG | GAGA | GTAC |
| B-0819N | AGGA | ACGCC | ACGT | GCATA | TCTT | CAGAG | GAGAG | CATG | GAGA | GTAC |
| B-0812 | AGGA | ACGCC | ACGT | GCATA | TCTT | CAGAG | GAGAG | GATG | GAGA | GTAC |
| B-0816 | AGGA | ACGCC | ACGT | GCATA | TCTT | CAGAG | GAGAG | GATG | GAGA | GTAC |

TABLE XI-continued

| Position cDNA | 5555 3333 6789 | 44444 12222 90123 | 5555 5666 9012 | 44444 00111 89012 | 2222 6777 9012 | 33333 55666 89012 | 22333 99000 89012 | 3333 6666 3456 | 2222 0000 3456 | 3333 6666 6789 |
|---|---|---|---|---|---|---|---|---|---|---|
| B-0815 | AGGA | ACGCC | ACGT | GCATA | TCTT | CAGAG | GTGAG | CATG | GAGA | GTAC |
| B-4204 | AGGA | ACGCC | ACGT | GCATA | TCTA | CAGAC | GAGAG | DATG | GAGA | GTAT |
| B-4201 | AGGA | ACGCC | ACGT | GCATA | TCTA | CAGAG | GAGAG | CATG | GAGA | GTAC |
| B-4202 | AGGA | ACGCC | ACGT | GCATA | TCTA | CAGAG | GAGAG | CATG | GAGA | GTAC |
| B-4205 | AGGA | ACGCC | ACGT | GCATA | TCTA | CAGAG | GAGAG | CATG | GAGA | GTAC |
| B-0814 | AGGA | ACGCC | ACGT | GTACC | TCTT | CAGAG | GAGAG | CATG | GAGA | GTAC |
| B-0719 | AGGA | ACGCC | ACGT | GCATG | TCTA | CAGAG | GAGAG | CATG | GAGA | GTAC |
| B-0807 | AGGA | ACGCC | ACGT | GCATG | TCTT | CAGAG | GAGAG | CATG | GAGA | GTAC |
| B-4104 | AGGA | ACGCC | ACGT | GCATG | TCTC | CAGAG | GAGAG | CATG | GGAA | GTAC |
| B-0821 | AGGA | ACGCC | CTGT | GCATA | TCTT | CAGAG | GAGAG | CATG | GAGA | GTAC |
| B-4414 | AGGA | ACGCC | CTGT | GCATA | TCTC | CAGAG | GAGAA | DATG | GGAA | GTAC |
| B-5108 | AGGA | ACGCC | CTGT | GCATA | TCTT | CAGAC | GAGAA | DATG | GGAC | GTAT |
| B-5120 | AGGA | ACGCC | CTGT | GCATA | TCTT | CAGAC | GAGAA | DATG | GGAC | GTAT |
| B-5709 | AGGA | ACGCC | CTGT | GCATA | ACAT | CAGGT | GAGAA | DATG | GGAT | GTAT |
| G-4420 | AGGA | ACGCC | CTGT | GTATG | TCTC | CAGAC | GAGAA | DATG | GGAA | GTAT |
| B-44020101 | AGGA | ACGCC | CTGT | GTATG | TCTC | CAGAG | GAGAA | DATG | GGAA | GTAC |
| B-44020102S | AGGA | ACGCC | CTGT | GTATG | TCTC | CAGAG | GAGAA | DATG | GGAA | GTAC |
| B-440202 | AGGA | ACGCC | CTGT | GTATG | TCTC | CAGAG | GAGAA | DATG | GGAA | GTAC |
| B-440203 | AGGA | ACGCC | CTGT | GTATG | TCTC | CAGAG | GAGAA | DATG | GGAA | GTAC |
| B-4405 | AGGA | ACGCC | CTGT | GTATG | TCTC | CAGAG | GAGAA | DATG | GGAA | GTAC |
| B-4411 | AGGA | ACGCC | CTGT | GTATG | TCTC | CAGAG | GAGAA | DATG | GGAA | GTAC |
| B-4412 | AGGA | ACGCC | CTGT | GTATG | TCTC | CAGAG | GAGAA | DATG | GGAA | GTAC |
| B-4419N | AGGA | ACGCC | CTGT | GTATG | TCTC | CAGAG | GAGAA | DATG | GGAA | GTAC |
| B-4422 | AGGA | ACGCC | CTGT | GTATG | TCTC | CAGAG | GAGAA | DATG | GGAA | GTAC |
| B-4423N | AGGA | ACGCC | CTGT | GTATG | TCTC | CAGAG | GAGAA | DATG | GGAA | GTAC |
| B-4424 | AGGA | ACGCC | CTGT | GTATG | TCTC | CAGAG | GAGAA | DATG | GGAA | GTAC |
| B-4425 | AGGA | ACGCC | CTGT | GTATG | TCTC | CAGAG | GAGAA | DATG | GGAA | GTAC |
| B-4427 | AGGA | ACGCC | CTGT | GTATG | TCTC | CAGAG | GAGAA | DATG | GGAA | GTAC |
| B-4433 | AGGA | ACGCC | CTGT | GTATG | TCTC | CAGAG | GAGAA | DATG | GGAA | GTAC |
| B-4434 | AGGA | ACGCC | CTGT | GTATG | TCTC | CAGAG | GAGAA | DATG | GGAA | GTAC |
| B-4435 | AGGA | ACGCC | CTGT | GTATG | TCTC | CAGAG | GAGAA | DATG | GGAA | GTAC |
| B-4408 | AGGA | ACGCC | CTGT | GTATG | TCTC | CAGAG | GAGAA | DATG | GGAT | GTAC |
| B-4409 | AGGA | ACGCC | CTGT | GTATG | TCTC | CAGAG | GAGAG | DATG | GGAA | GTAC |
| B-4406 | AGGA | ACGCC | CTGT | GTATG | TCTT | CAGAG | GAGAA | DATG | GGAC | GTAC |
| B-8301 | AGGA | ACGCC | CTGT | GTATG | TCTA | CAGAG | GAGAG | DATG | GAGA | GTAC |
| B-0704 | AGGA | ACGCC | GAGT | GCATG | TCTA | CAGAG | GAGAG | CATG | GAGA | GTAC |
| B-0725 | AGGA | ACGCC | GAGT | GCATG | TCTA | CAGAG | GAGAG | CATG | GAGA | GTAC |
| B-4416 | AGGA | ACGCC | GAGT | GTATG | TCTC | CAGAG | GAGAA | DATG | GGAA | GTAC |
| B-4421 | AGGA | ACGCC | GAGT | GTATG | TCTC | CAGAG | GAGAA | DATG | GGAA | GTAC |
| B-0811 | AGGA | ACGCC | GCGT | GCATA | TCTT | CAGAG | GAGAG | CATG | GAGA | GTAC |
| B-1551 | AGGA | CCGCC | CTGT | GCATG | TCTG | CAGAG | GAGAG | DATG | GAGA | GTAC |
| B-4417 | AGGA | CCGCC | CTGT | GCATG | TCTC | CAGAG | GAGAA | DATG | GGAA | GTAC |
| B-4418 | AGGA | TAGCC | CTGT | GTATA | TCTC | CAGAG | GAGAA | DATG | GGAA | GTAT |
| B-4415 | AGGA | TAGCC | CTGT | GTATA | TCTC | CAGAG | GAGAG | DATG | GGAA | GTAT |
| B-4501 | AGGA | TAGCC | CTGT | GTATA | TCTC | CAGAG | GAGAG | DATG | GGAA | GTAT |
| B-4503 | AGGA | TAGCC | CTGT | GTATA | TCTC | CAGAG | GAGAG | DATG | GGAA | GTAT |
| B-4504 | AGGA | TAGCC | CTGT | GTATA | TCTC | CAGAG | GAGAG | DATG | GGAA | GTAT |
| B-4505 | AGGA | TAGCC | CTGT | GTATA | TCTC | CAGAG | GAGAG | DATG | GGAA | GTAT |
| B-4506 | AGGA | TAGCC | CTGT | GTATA | TCTA | CAGAG | GAGAG | DATG | GGAA | GTAT |
| B-8201 | AGGA | TAGCC | CTGT | GCATA | TCTA | CAGAG | GAGAG | DATG | GAGA | GTTT |
| B-8202 | AGGA | TAGCC | CTGT | GCATA | TCTA | CAGAG | GAGAG | DATG | GAGA | GTTt |

TABLE XI-continued

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-3538 | AGGA | TCGCC | CTGT | GCATG | TCTT | CAGAG | GAGAG | GATG | GGAC | GTAT |
| B-3701 | AGGA | TCGCC | ACGT | GTATA | TCTC | CAGAG | GAGGA | GATG | GGAC | GTCT |
| B-3703N | AGGA | TCGCC | ACGT | GTATA | TCTC | CAGAG | GAGGA | GATG | GGAC | GTCT |
| B-3704 | AGGA | TCGCC | ACGT | GTATA | TCTC | CAGAG | GAGGA | GATG | GGAC | GTCT |
| B-3705 | AGGA | TCGCC | ACGT | GTATA | TCTC | CAGAG | GAGGA | GATG | GGAC | GTCT |
| B-4502 | AGGA | TCGCC | CTGT | GTATA | TCTC | CAGAG | GAGAG | GATG | GGAA | GTAT |
| B-0731 | AGCG | ACGCC | ACGT | GCATG | TCTA | CAGAG | GAGAG | CATG | GAGA | GTAC |
| B-0806 | AGCG | ACGCC | ACGT | GCATA | TCTT | CAGAG | GAGAA | CATG | GAGA | GTAC |
| B-0820 | AGCG | ACGCC | ACGT | GCATA | TCTT | CAGAG | GAGAG | CATG | GAGA | GTAC |
| B-4404 | AGCG | ACGCC | ACGT | GCATG | TCTC | CAGAG | GAGAA | GATG | GGAA | GTAC |
| B-0720 | AGCG | ACGCC | CTGT | GCATG | TCTA | CAGAG | GAGAG | CATG | GAGA | GTAC |
| B-0724 | AGCG | ACGCC | CTGT | GCATG | TCTA | CAGAG | GAGAG | CATG | GAGA | GTAC |
| B-3518 | AGCG | ACGCC | CTGT | GCATA | TCTT | CAGAG | GAGAG | GATG | GGAC | GTAT |
| B-4428 | AGCG | ACGCC | CTGT | GTATG | TCTC | CAGAG | GAGAA | GATG | GGAA | GTAT |
| B-5105 | AGCG | ACGCC | CTGT | GCATA | TCTT | CAGAC | GAGAA | GATG | GGAC | GTAT |
| B-5129 | AGCG | ACGCC | CTGT | GCATA | TCTT | CAGAC | GAGAA | GATG | GGAC | GTAT |
| B-5702 | AGCG | ACGCC | CTGT | GCATA | ACAT | CAGGT | GAGAA | GATG | GGAT | GTAT |
| B-5704 | AGCG | ACGCC | CTGT | GTATG | ACAT | CAGGT | GAGAA | GATG | GGAT | GTAT |
| B-5705 | AGCG | ACGCC | CTGT | GTATA | ACAT | CAGAG | GAGAA | GATG | GGAT | GTAT |
| B-0705 | AGCG | ACGCC | GAGT | GCATA | TCTA | CAGAG | GAGAG | CATG | GAGA | GTAC |
| B-0706 | AGCG | ACGCC | GAGT | GCATA | TCTA | CAGAG | GAGAG | CATG | GAGA | GTAC |
| B-0732 | AGCG | ACGCC | GAGT | GCATA | TCTT | CAGAG | GAGAG | CATG | GAGA | GTAC |
| B-4015 | AGCG | ACGCC | GAGT | GCATA | TCTC | CAGAG | GAGAG | CATG | GGAA | GTAC |
| B-4016 | AGCG | ACGCC | GAGT | GCATA | TCTC | CAGAG | GAGAG | CATG | GGAA | GTAC |
| B-4023 | AGCG | ACGCC | GAGT | GCATA | TCTC | CAGAG | GAGAG | GATG | GGAA | GTAC |
| B-4805 | AGCG | ACGCC | GAGT | GCATA | TCTC | CAGAG | GAGAG | CATG | GAGA | GTAC |
| B-0713 | AGCG | ACGCC | GAGT | GCATG | AGTA | CAGAG | GTGAG | CATG | GAGG | GTAC |
| B-070201 | AGCG | ACGCC | GAGT | GCATG | TCTA | CAGAG | GAGAG | CATG | GAGA | GTAC |
| B-070202 | AGCG | ACGCC | GAGT | GCATG | TCTA | CAGAG | GAGAG | CATG | GAGA | GTAC |
| B-070203 | AGCG | ACGCC | GAGT | GCATG | TCTA | CAGAG | GAGAG | CATG | GAGA | GTAC |
| B-070204 | AGCG | ACGCC | GAGT | GCATG | TCTA | CAGAG | GAGAG | CATG | GAGA | GTAC |
| B-0703 | AGCG | ACGCC | GAGT | GCATG | TCTA | CAGAG | GAGAG | CATG | GAGA | GTAC |
| B-0716 | AGCG | ACGCC | GAGT | GCATG | TCTA | CAGAG | GAGAG | CATG | GAGA | GTAC |
| B-0721 | AGCG | ACGCC | GAGT | GCATG | TCTA | CAGAG | GAGAG | CATG | GAGA | GTAC |
| B-0722 | AGCG | ACGCC | GAGT | GCATG | TCTA | CAGAG | GAGAG | CATG | GAGA | GTAC |
| B-0723 | AGCG | ACGCC | GAGT | GCATG | TCTA | CAGAG | GAGAG | CATG | GAGA | GTAC |
| B-0729 | AGCG | ACGCC | GAGT | GCATG | TCTA | CAGAG | GAGAG | CATG | GAGA | GTAC |
| B-0730 | AGCG | ACGCC | GAGT | GCATG | TCTA | CAGAG | GAGAG | CATG | GAGA | GTAC |
| B-0733 | AGCG | ACGCC | GAGT | GCATG | TCTA | CAGAG | GAGAG | CATG | GAGA | GTAC |
| B-0735 | AGCG | ACGCC | GAGT | GCATG | TCTA | CAGAG | GAGAG | CATG | GAGA | GTAC |
| B-0707 | AGCG | ACGCC | GAGT | GCATG | TCTA | CAGAG | GAGAG | GATG | GAGA | GTAC |
| B-0712 | AGCG | ACGCC | GAGT | GCATG | TCTA | CAGAG | GAGAG | GATG | GAGA | GTAT |
| B-0718 | AGCG | ACGCC | GAGT | GCATG | TCTA | CAGAG | GAGAG | GATG | GAGA | GTAT |
| B-0736 | AGCG | ACGCC | GAGT | GCATG | TCTA | CAGAG | GAGAA | CATG | GAGA | GTAC |
| B-0715 | AGCG | ACGCC | GAGT | GCATG | TCTA | CAGAG | GTGAG | CATG | GAGA | GTAC |
| B-0727 | AGCG | ACGCC | GAGT | GCATG | TCTC | CAGAG | GAGGA | CATG | GAGA | GTAC |
| B-4032 | AGCG | ACGCC | GAGT | GCATG | TCTC | CAGAG | GAGAG | CATG | GGAA | GTAC |
| B-4808 | AGCG | ACGCC | GAGT | GCATG | TCTC | CAGAG | GAGAG | CATG | GAGA | GTAC |

TABLE XI-continued

```
              5555   44444  5555   44444  2222   33333  22333  3333   2222   3333
              3333   12222  5666   00111  6777   55666  99000  6666   0000   6666
Position cDNA 6789   90123  9012   89012  9012   89012  89012  3456   3456   6789

B-0710        AGCG   ACGCC  GAGT   GCATG  TCTG   CAGAG  GAGAG  CATG   GAGA   GTAC

B-0708        AGCG   ACGCC  GAGT   GCATG  TCTT   CAGAG  GAGAG  CATG   GAGA   GTAC

B-0714        AGCG   ACGCC  GAGT   GTATG  TCTA   CAGAG  GAGAG  DATG   GAGA   GTAC

B-0728        AGCG   ACGCC  GAGT   GTATG  TCTA   CAGAG  GAGAG  CATG   GAGA   GTAC

B-0709        AGCG   CCGCC  GAGT   GCATG  TCTA   CAGAG  GAGAG  CATG   GAGA   GTAC

B-0711        AGCG   CCGCC  GAGT   GCATG  TCTA   CAGAG  GAGAA  CATG   GAGA   GTAC

B-1547        AGCG   CCGCC  GAGT   GCATG  TCTC   CAGAG  GAGAG  GATG   GAGA   GTAC
B-1549        AGCG   CCGCC  GAGT   GCATG  TCTC   CAGAG  GAGAG  GATG   GAGA   GTAC

B-0717        AGCG   CCGCC  GAGT   GTATG  TCTA   CAGAG  GAGAG  CATG   GAGA   GTAC

B-1565        AGCG   CCGCC  CTGT   GCATG  TCTC   CAGAG  GAGAG  GATG   GGAT   GTAC

B-1813        AGCG   CCGCC  ACGT   GCATG  TCTC   CAGAG  GAGAG  GATG   GGAC   GTAC

B-3508        AGCG   CCGCC  CTGT   GCATG  TCTT   CAGAG  GAGAG  GATG   GGAC   GTAT
B-3545        AGCG   CCGCC  CTGT   GCATG  TCTT   CAGAG  GAGAG  GATG   GGAC   GTAT

B-5509        AGCG   TAGCC  GAGT   GCATA  TCTA   CAGAC  GAGAG  GATG   GAGA   GTAT

B-1403        AGCG   TAGCC  ACGT   GTATA  TCTG   CAGTG  GAGAG  GATG   GAGA   GTAT

B-3908        AGCG   TAGCC  ACGT   GCATA  TCTC   CAGAG  GAGAG  GATG   GAGA   GTAC

B-3911        AGCG   TAGCC  ACGT   GCATA  TCTG   CAGAG  GAGAG  GATG   GAGA   GTAC

B-1530        AGTG   ACGCC  CTGT   GCATA  TCTC   CAGAG  GAGAG  GATG   GGAT   GTAC

B-1545        AGTG   ACGCC  CTGT   GCATG  TCTC   CAGAG  GAGAG  CATG   GGAT   GTAC

B-1563        AGTG   ACGCC  CTGT   GCATG  TCTC   CAGAG  GAGAG  GATG   GGAT   GTAC

B-1577        AGTG   ACGCC  CTGT   GTATG  TCTC   CAGAG  GAGAG  GATG   GGAT   GTAC

B-2725        AGTG   ACGCC  CTGT   GTACC  TCTG   CAGAA  GAGAG  TATG   GAGA   GTAT

B-3544        AGTG   ACGCC  CTGT   GCATA  TCTT   CAGAG  GAGAG  GATG   GGAC   GTAC

B-151101      AGTG   CCGCC  CTGT   GCATG  TCTA   CAGAG  GAGAG  GATG   GGAT   GTAC
B-151102      AGTG   CCGCC  CTGT   GCATG  TCTA   CAGAG  GAGAG  GATG   GGAT   GTAC
B-1576        AGTG   CCGCC  CTGT   GCATG  TCTA   CAGAG  GAGAG  GATG   GGAT   GTAC

B-5603        AGTG   CCGCC  CTGT   GCATG  TCTA   CAGAG  GAGAG  GATG   GAGA   GTAC

B-4601        AGTG   CCGCC  CTGT   GCATG  AGTA   CAGAG  GTGAG  GATG   GGAT   GTAC
B-4602        AGTG   CCGCC  CTGT   GCATG  AGTA   CAGAG  GTGAG  GATG   GGAT   GTAC

B-1550        AGTG   CCGCC  ACGT   GCATG  TCTC   CAGAG  GAGAG  GATG   GGAT   GTAC

B-1819        AGTG   CCGCC  ACGT   GCATG  TCTC   CAGAG  GAGAG  GATG   GGAC   GTAC

B-1504        AGTG   CCGCC  CTGT   GCATG  TCTC   CAGAC  GAGAG  GATG   GGAT   GTAT

B-1535        AGTG   CCGCC  CTGT   GCATG  TCTC   CAGAC  GAGAG  GATG   GGAT   GTAC

B-1526N       AGTG   CCGCC  CTGT   GCATG  TCTC   CAGAG  GAGAG  GATG   GGAT   GTAA

B-1546        AGTG   CCGCC  CTGT   GCATG  TCTC   CAGAG  GAGAG  GATG   GGAA   GTAC
B-1553        AGTG   CCGCC  CTGT   GCATG  TCTC   CAGAG  GAGAG  GATG   GGAA   GTAC

B-1554        AGTG   CCGCC  CTGT   GCATG  TCTC   CAGAG  GAGAG  GATG   GAGA   GTAC

B-1568        AGTG   CCGCC  CTGT   GCATG  TCTC   CAGAG  GAGAG  CATG   GAGA   GTAC

B-1524        AGTG   CCGCC  CTGT   GCATG  TCTC   CAGAG  GAGAA  GATG   GGAT   GTAC

B-1543        AGTG   CCGCC  CTGT   GCATG  TCTC   CAGAG  GAGGA  GATG   GGAT   GTAC

B-1507        AGTG   CCGCC  CTGT   GCATG  TCTC   CAGAG  GAGAG  CATG   GGAT   GTAC
```

TABLE XI-continued

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-15010101 | AGTG | CCGCC | CTGT | GCATG | TCTC | CAGAG | GAGAG | GATG | GGAT | GTAC |
| B-15010102N | AGTG | CCGCC | CTGT | GCATG | TCTC | CAGAG | GAGAG | GATG | GGAT | GTAC |
| B-150102 | AGTG | CCGCC | CTGT | GCATG | TCTC | CAGAG | GAGAG | GATG | GGAT | GTAC |
| B-150103 | AGTG | CCGCC | CTGT | GCATG | TCTC | CAGAG | GAGAG | GATG | GGAT | GTAC |
| B-150104 | AGTG | CCGCC | CTGT | GCATG | TCTC | CAGAG | GAGAG | GATG | GGAT | GTAC |
| B-1512 | AGTG | CCGCC | CTGT | GCATG | TCTC | CAGAG | GAGAG | GATG | GGAT | GTAC |
| B-1514 | AGTG | CCGCC | CTGT | GCATG | TCTC | CAGAG | GAGAG | GATG | GGAT | GTAC |
| B-1515 | AGTG | CCGCC | CTGT | GCATG | TCTC | CAGAG | GAGAG | GATG | GGAT | GTAC |
| B-1519 | AGTG | CCGCC | CTGT | GCATG | TCTC | CAGAG | GAGAG | GATG | GGAT | GTAC |
| B-1528 | AGTG | CCGCC | CTGT | GCATG | TCTC | CAGAG | GAGAG | GATG | GGAT | GTAC |
| B-1533 | AGTG | CCGCC | CTGT | GCATG | TCTC | CAGAG | GAGAG | GATG | GGAT | GTAC |
| B-1534 | AGTG | CCGCC | CTGT | GCATG | TCTC | CAGAG | GAGAG | GATG | GGAT | GTAC |
| B-1538 | AGTG | CCGCC | CTGT | GCATG | TCTC | CAGAG | GAGAG | GATG | GGAT | GTAC |
| B-1560 | AGTG | CCGCC | CTGT | GCATG | TCTC | CAGAG | GAGAG | GATG | GGAT | GTAC |
| B-1570 | AGTG | CCGCC | CTGT | GCATG | TCTC | CAGAG | GAGAG | GATG | GGAT | GTAC |
| B-1571 | AGTG | CCGCC | CTGT | GCATG | TCTC | CAGAG | GAGAG | GATG | GGAT | GTAC |
| B-1575 | AGTG | CCGCC | CTGT | GCATG | TCTC | CAGAG | GAGAG | GATG | GGAT | GTAC |
| B-1578 | AGTG | CCGCC | CTGT | GCATG | TCTC | CAGAG | GAGAG | GATG | GGAT | GTAC |
| B-1579N | AGTG | CCGCC | CTGT | GCATG | TCTC | CAGAG | GAGAG | GATG | GGAT | GTAC |
| B-1581 | AGTG | CCGCC | CTGT | GCATG | TCTC | CAGAG | GAGAG | GATG | GGAT | GTAC |
| B-1582 | AGTG | CCGCC | CTGT | GCATG | TCTC | CAGAG | GAGAG | GATG | GGAT | GTAC |
| B-1527 | AGTG | CCGCC | CTGT | GCATG | TCTC | CAGAG | GAGAG | GATG | GGAT | GTTT |
| B-1532 | AGTG | CCGCC | CTGT | GCATG | TCTC | CAGAG | GAGAG | GATG | GGAT | GTCT |
| B-1557 | AGTG | CCGCC | CTGT | GCATG | TCTC | CAGAG | GTGAA | GATG | GGAT | GTAC |
| B-1566 | AGTG | CCGCC | CTGT | GCATG | TCTG | CAGAG | GAGAG | GATG | GGAT | GTAC |
| B-1508 | AGTG | CCGCC | CTGT | GCATG | TCTT | CAGAG | GAGAG | GATG | GGAT | GTAC |
| B-1556 | AGTG | CCGCC | CTGT | GCATG | TCTT | CAGAG | GAGAG | GATG | GGAT | GTAC |
| B-351401 | AGTG | CCGCC | CTGT | GCATG | TCTT | CAGAG | GAGAG | GATG | GGAC | GTAT |
| B-351402 | AGTG | CCGCC | CTGT | GCATG | TCTT | CAGAG | GAGAG | GATG | GGAC | GTAT |
| B-3543 | AGTG | CCGCC | CTGT | GCATG | TCTT | CAGAG | GAGAG | GATG | GGAC | GTAC |
| B-1573 | AGTG | TAGCC | CTGT | GCATA | TCTC | CAGAG | GAGAG | GATG | GGAT | GTAC |
| B-1558 | AGTG | TCGCC | CTGT | GCATA | TCTC | CAGAG | GAGAG | GATG | GGAT | GTAC |
| B-3918 | AGTG | TCGCC | ACGT | GCATA | TCTG | CAGAG | GAGAG | GATG | GAGA | GTAC |
| B-0734 | AGCT | ACGCC | ACGT | GCATA | TCTA | CAGAG | GAGAG | CATG | GAGA | GTAC |
| B-5504 | AGCT | ACGCC | ACGT | GCATA | TCTA | CAGAG | GAGAG | CATG | GAGA | GTAC |
| B-5612 | AGCT | ACGCC | ACGT | GCATA | TCTA | CAGAG | GAGAG | GATG | GAGA | GTAC |
| B 4039 | AGCT | ACGCC | ACGT | GCATA | TCTC | CAGAG | GAGAG | CATG | GGAA | GTAC |
| B-2715 | AGCT | ACGCC | ACGT | GTACC | TCTG | CAGAA | GAGAG | TATG | GAGA | GTAT |
| B-3914 | AGCT | ACGCC | ACGT | GCATA | TCTG | CAGAG | GAGAG | CATG | GAGA | GTAC |
| B-0813 | AGCT | ACGCC | ACGT | GCATA | TCTT | CAGAG | GAGAG | CATG | GAGA | GTAC |
| B-5121 | AGCT | ACGCC | ACGT | GCATA | TCTT | CAGAC | GTGAA | GATG | GGAC | GTAT |
| B-5508 | AGCT | ACGCC | CTGT | GCATA | TCTA | CAGAG | GAGAG | GATG | GAGA | GTAC |
| B-560501 | AGCT | ACGCC | CTGT | GCATA | TCTA | CAGAC | GAGAG | GATG | GAGA | GTAC |
| B-560502 | AGCT | ACGCC | CTGT | GCATA | TCTA | CAGAC | GAGAG | GATG | GAGA | GTAC |
| B-5606 | AGCT | ACGCC | CTGT | GCATA | TCTA | CAGAC | GAGAG | GATG | GGAC | GTAT |
| B-1548 | AGCT | ACGCC | CTGT | GCATA | TCTC | CAGAG | GAGAG | GATG | GGAT | GTAC |
| B-4005 | AGCT | ACGCC | CTGT | GCATA | TCTC | CAGAG | GAGAG | CATG | GGAA | GTAC |
| B-4026 | AGCT | ACGCC | CTGT | GCATA | TCTC | CAGAG | GAGAG | GATG | GGAA | GTAC |
| B-4028 | AGCT | ACGCC | CTGT | GCATA | TCTC | CAGAG | GAGAG | GATG | GGAA | GTAT |

TABLE XI-continued

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-5107 | AGCT | ACGCC | CTGT | GCATA | TCTC | CAGAC | GAGAA | GATG | GGAC | GTAT |
| B-520101 | AGCT | ACGCC | CTGT | GCATA | TCTC | CAGAC | GAGAA | GATG | GGAC | GTAT |
| B-520102 | AGCT | ACGCC | CTGT | GCATA | TCTC | CAGAC | GAGAA | GATG | GGAC | GTAT |
| B-520103 | AGCT | ACGCC | CTGT | GCATA | TCTC | CAGAC | GAGAA | GATG | GGAC | GTAT |
| B-520104 | AGCT | ACGCC | CTGT | GCATA | TCTC | CAGAC | GAGAA | GATG | GGAC | GTAT |
| B-5203 | AGCT | ACGCC | CTGT | GCATA | TCTC | CAGAC | GAGAA | GATG | GGAC | GTAT |
| B-5204 | AGCT | ACGCC | CTGT | GCATA | TCTC | CAGAC | GAGAA | GATG | GGAC | GTAT |
| B-5205 | AGCT | ACGCC | CTGT | GCATA | TCTC | CAGAC | GAGAA | GATG | GGAC | GTAT |
| B-5202 | AGCT | ACGCC | CTGT | GCATA | TCTC | CAGAC | GAGAA | GATG | GGAT | GTAT |
| B-7805 | AGCT | ACGCC | CTGT | GCATA | TCTC | CAGAC | GAGAG | GATG | GGAC | GTAT |
| B-1509 | AGCT | ACGCC | CTGT | GCATA | TCTG | CAGAG | GAGAG | GATG | GAGA | GTAC |
| B-5122 | AGCT | ACGCC | CTGT | GCATA | TCTG | CAGAC | GAGAA | GATG | GGAC | GTAT |
| B-7803 | AGCT | ACGCC | CTGT | GCATA | TCTG | CAGAC | GAGAG | GATG | GGAC | GTAT |
| B-570301 | AGCT | ACGCC | CTGT | GCATA | ACAT | CAGGT | GAGAA | GATG | GGAT | GTAT |
| B-570302 | AGCT | ACGCC | CTGT | GCATA | ACAT | CAGGT | GAGAA | GATG | GGAT | GTAT |
| B-5707 | AGCT | ACGCC | CTGT | GCATA | ACAT | CAGGT | GAGAA | GATG | GGAT | GTAT |
| B-5808 | AGCT | ACGCC | CTGT | GCATA | ACAT | CAGAC | GAGAA | GATG | GGAC | GTAT |
| B-510101 | AGCT | ACGCC | CTGT | GCATA | TCTT | CAGAC | GAGAA | GATG | GGAC | GTAT |
| B-510102 | AGCT | ACGCC | CTGT | GCATA | TCTT | CAGAC | GAGAA | GATG | GGAC | GTAT |
| B-510103 | AGCT | ACGCC | CTGT | GCATA | TCTT | CAGAC | GAGAA | GATG | GGAC | GTAT |
| B-510104 | AGCT | ACGCC | CTGT | GCATA | TCTT | CAGAC | GAGAA | GATG | GGAC | GTAT |
| B-510105 | AGCT | ACGCC | CTGT | GCATA | TCTT | CAGAC | GAGAA | GATG | GGAC | GTAT |
| B-510201 | AGCT | ACGCC | CTGT | GCATA | TCTT | CAGAC | GAGAA | GATG | GGAC | GTAT |
| B-510202 | AGCT | ACGCC | CTGT | GCATA | TCTT | CAGAC | GAGAA | GATG | GGAC | GTAT |
| B-5103 | AGCT | ACGCC | CTGT | GCATA | TCTT | CAGAC | GAGAA | GATG | GGAC | GTAT |
| B-5109 | AGCT | ACGCC | CTGT | GCATA | TCTT | CAGAC | GAGAA | GATG | GGAC | GTAT |
| B-5111N | AGCT | ACGCC | CTGT | GCATA | TCTT | CAGAC | GAGAA | GATG | GGAC | GTAT |
| B-5112 | AGCT | ACGCC | CTGT | GCATA | TCTT | CAGAC | GAGAA | GATG | GGAC | GTAT |
| B-5114 | AGCT | ACGCC | CTGT | GCATA | TCTT | CAGAC | GAGAA | GATG | GGAC | GTAT |
| B-5118 | AGCT | ACGCC | CTGT | GCATA | TCTT | CAGAC | GAGAA | GATG | GGAC | GTAT |
| B-5119 | AGCT | ACGCC | CTGT | GCATA | TCTT | CAGAC | GAGAA | GATG | GGAC | GTAT |
| B-5123 | AGCT | ACGCC | CTGT | GCATA | TCTT | CAGAC | GAGAA | GATG | GGAC | GTAT |
| B-5124 | AGCT | ACGCC | CTGT | GCATA | TCTT | CAGAC | GAGAA | GATG | GGAC | GTAT |
| B-5126 | AGCT | ACGCC | CTGT | GCATA | TCTT | CAGAC | GAGAA | GATG | GGAC | GTAT |
| B-5127N | AGCT | ACGCC | CTGT | GCATA | TCTT | CAGAC | GAGAA | GATG | GGAC | GTAT |
| B-5128 | AGCT | ACGCC | CTGT | GCATA | TCTT | CAGAC | GAGAA | GATG | GGAC | GTAT |
| B-5130 | AGCT | ACGCC | CTGT | GCATA | TCTT | CAGAC | GAGAA | GATG | GGAC | GTAT |
| B-5132 | AGCT | ACGCC | CTGT | GCATA | TCTT | CAGAC | GAGAA | GATG | GGAC | GTAT |
| B-5133 | AGCT | ACGCC | CTGT | GCATA | TCTT | CAGAC | GAGAA | GATG | GGAC | GTAT |
| B-7801 | AGCT | ACGCC | CTGT | GCATA | TCTT | CAGAC | GAGAG | GATG | GGAC | GTAT |
| B-780201 | AGCT | ACGCC | CTGT | GCATA | TCTT | CAGAC | GAGAG | GATG | GGAC | GTAT |
| B-780202 | AGCT | ACGCC | CTGT | GCATA | TCTT | CAGAC | GAGAG | GATG | GGAC | GTAT |
| B-7804 | AGCT | ACGCC | CTGT | GCATA | TCTT | CAGAC | GAGAG | GATG | GGAC | GTAT |
| B-3502 | AGCT | ACGCC | CTGT | GCATA | TCTT | CAGAG | GAGAG | GATG | GGAC | GTAT |
| B-3504 | AGCT | ACGCC | CTGT | GCATA | TCTT | CAGAG | GAGAG | GATG | GGAC | GTAT |
| B-350901 | AGCT | ACGCC | CTGT | GCATA | TCTT | CAGAG | GAGAG | GATG | GGAC | GTAT |
| B-350902 | AGCT | ACGCC | CTGT | GCATA | TCTT | CAGAG | GAGAG | GATG | GGAC | GTAT |
| B-3512 | AGCT | ACGCC | CTGT | GCATA | TCTT | CAGAG | GAGAG | GATG | GGAC | GTAC |
| B-3522 | AGCT | ACGCC | CTGT | GCATA | TCTT | CAGAG | GAGAG | GATG | GGAC | GTAC |
| B-5104 | AGCT | ACGCC | CTGT | GCATA | TCTT | CAGAG | GAGAA | GATG | GGAC | GTAT |
| B-5106 | AGCT | ACGCC | CTGT | GCATA | TCTT | CAGAG | GAGAA | GATG | GGAC | GTAC |
| B-5117 | AGCT | ACGCC | CTGT | TTATA | TCTT | CAGAC | GAGAA | GATG | GGAC | GTAT |
| B-15170101 | AGCT | ACGCC | CTGT | GTACC | ACAT | CAGAG | GAGAA | GATG | GGAT | GTAC |
| B-15170102 | AGCT | ACGCC | CTGT | GTACC | ACAT | CAGAG | GAGAA | GATG | GGAT | GTAC |
| B-1510 | AGCT | ACGCC | CTGT | GCATG | TCTG | CAGAG | GAGAG | GATG | GAGA | GTAC |
| B-1537 | AGCT | ACGCC | CTGT | GCATG | TCTG | CAGAG | GAGAG | GATG | GAGA | GTAC |
| B-3534 | AGCT | ACGCC | CTGT | GCATG | TCTT | CAGAG | GAGAG | GATG | GGAC | GTAT |

TABLE XI-continued

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-3539 | AGCT | ACGCC | CTGT | GCATG | TCTT | CAGAG | GAGAG | GATG | GGAC | GTAC |
| B-440301 | AGCT | ACGCC | CTGT | GTATG | TCTC | CAGAG | GAGAA | GATG | GGAA | GTAC |
| B-4413 | AGCT | ACGCC | CTGT | GTATG | TCTC | CAGAG | GAGAA | GATG | GGAA | GTAC |
| B-4426 | AGCT | ACGCC | CTGT | GTATG | TCTC | CAGAG | GAGAA | GATG | GGAA | GTAC |
| B-4429 | AGCT | ACGCC | CTGT | GTATG | TCTC | CAGAG | GAGAA | GATG | GGAA | GTAC |
| B-4430 | AGCT | ACGCC | CTGT | GTATG | TCTC | CAGAG | GAGAA | GATG | GGAA | GTAC |
| B-4432 | AGCT | ACGCC | CTGT | GTATG | TCTC | CAGAG | GAGAA | GATG | GGAA | GTAC |
| B-4436 | AGCT | ACGCC | CTGT | GTATG | TCTC | CAGAG | GAGAA | GATG | GGAA | GTAC |
| B-4437 | AGCT | ACGCC | CTGT | GTATG | TCTC | CAGAG | GAGAA | GATG | GGAA | GTAC |
| B-4438 | AGCT | ACGCC | CTGT | GTATG | TCTC | CAGAG | GAGAA | GATG | GGAA | GTAC |
| B-4439 | AGCT | ACGCC | CTGT | GTATG | TCTC | CAGAG | GAGAA | GATG | GGAA | GTAC |
| B-440302 | AGCT | ACGCC | CTGT | GTATG | TCTC | CAGAG | GAGAA | GATG | GGAA | GTAT |
| B-4407 | AGCT | ACGCC | CTGT | GTATG | TCTC | CAGAG | GAGAA | GATG | GGAA | GTAT |
| B-8101 | AGCT | ACGCC | GAGT | GCATA | TCTA | CAGAG | GAGAG | CATG | GAGA | GTAC |
| B-8102 | AGCT | ACGCC | GAGT | GCATA | TCTA | CAGAG | GAGAG | CATG | GAGA | GTAC |
| B-40060101 | AGCT | ACGCC | GAGT | GCATA | TCTC | CAGAC | GAGAG | GATG | GGAA | GTAT |
| B-40060102 | AGCT | ACGCC | GAGT | GCATA | TCTC | CAGAC | GAGAG | GATG | GGAA | GTAT |
| B-4019 | AGCT | ACGCC | GAGT | GCATA | TCTC | CAGAG | GAGAA | CATG | GGAA | GTAC |
| B-4037 | AGCT | ACGCC | GAGT | GCATA | TCTC | CAGAG | GAGAA | CATG | GGAA | GTAC |
| B-4047 | AGCT | ACGCC | GAGT | GCATA | TCTC | CAGAG | GAGAA | GATG | GGAA | GTAC |
| B-4431 | AGCT | ACGCC | GAGT | GCATA | TCTC | CAGAG | GAGAA | GATG | GGAA | GTAC |
| B-4002 | AGCT | ACGCC | GAGT | GCATA | TCTC | CAGAG | GAGAG | CATG | GGAA | GTAC |
| B-4027 | AGCT | ACGCC | GAGT | GCATA | TCTC | CAGAG | GAGAG | CATG | GGAA | GTAC |
| B-4029 | AGCT | ACGCC | GAGT | GCATA | TCTC | CAGAG | GAGAG | CATG | GGAA | GTAC |
| B-4035 | AGCT | ACGCC | GAGT | GCATA | TCTC | CAGAG | GAGAG | CATG | GGAA | GTAC |
| B-4040 | AGCT | ACGCC | GAGT | GCATA | TCTC | CAGAG | GAGAG | CATG | GGAA | GTAC |
| B-4045 | AGCT | ACGCC | GAGT | GCATA | TCTC | CAGAG | GAGAG | CATG | GGAA | GTAC |
| B-4801 | AGCT | ACGCC | GAGT | GCATA | TCTC | CAGAG | GAGAG | CATG | GAGA | GTAC |
| B-4804 | AGCT | ACGCC | GAGT | GCATA | TCTC | CAGAG | GAGAG | CATG | GAGA | GTAC |
| B-400101 | AGCT | ACGCC | GAGT | GCATA | TCTC | CAGAG | GAGAG | GATG | GGAA | GTAC |
| B-400102 | AGCT | ACGCC | GAGT | GCATA | TCTC | CAGAG | GAGAG | GATG | GGAA | GTAC |
| B-400103 | AGCT | ACGCC | GAGT | GCATA | TCTC | CAGAG | GAGAG | GATG | GGAA | GTAC |
| B-4010 | AGCT | ACGCC | GAGT | GCATA | TCTC | CAGAG | GAGAG | GATG | GGAA | GTAC |
| B-4011 | AGCT | ACGCC | GAGT | GCATA | TCTC | CAGAG | GAGAG | GATG | GGAA | GTAC |
| B-401401 | AGCT | ACGCC | GAGT | GCATA | TCTC | CAGAG | GAGAG | GATG | GGAA | GTAC |
| B-401402 | AGCT | ACGCC | GAGT | GCATA | TCTC | CAGAG | GAGAG | GATG | GGAA | GTAC |
| B-401403 | AGCT | ACGCC | GAGT | GCATA | TCTC | CAGAG | GAGAG | GATG | GGAA | GTAC |
| B-4022N | AGCT | ACGCC | GAGT | GCATA | TCTC | CAGAG | GAGAG | GATG | GGAA | GTAC |
| B-4025 | AGCT | ACGCC | GAGT | GCATA | TCTC | CAGAG | GAGAG | GATG | GGAA | GTAC |
| B-4043 | AGCT | ACGCC | GAGT | GCATA | TCTC | CAGAG | GAGAG | GATG | GGAA | GTAC |
| B-4021 | AGCT | ACGCC | GAGT | GCATA | TCTC | CAGAG | GAGAG | GATG | GGAT | GTAC |
| B-400104 | AGCT | ACGCC | GAGT | GCATA | TCTC | CAGAG | GAGAG | GATG | GGAA | GTAT |
| B-4004 | AGCT | ACGCC | GAGT | GCATA | TCTC | CAGAG | GAGAG | GATG | GGAA | GTAT |
| B-4012 | AGCT | ACGCC | GAGT | GCATA | TCTC | CAGAG | GAGAG | GATG | GAGA | GTAC |
| B-4046 | AGCT | ACGCC | GAGT | GCATA | TCTC | CAGAG | GAGAG | GATG | GAGA | GTAC |
| B-4803 | AGCT | ACGCC | GAGT | GCATA | TCTC | CAGAG | GAGAG | GATG | GAGA | GTAC |
| B-4030 | AGCT | ACGCC | GAGT | GCATA | TCTC | CAGGT | GAGAG | GATG | GGAA | GTAT |
| B-4034 | AGCT | ACGCC | GAGT | GCATA | TCTC | CAGGT | GAGAG | GATG | GGAA | GTAT |
| B-2720 | AGCT | ACGCC | GAGT | GCATA | TCTG | CAGAA | GAGAG | TATG | GAGA | GTAC |
| B-2707 | AGCT | ACGCC | GAGT | GCATA | TCTG | CAGAG | GAGGA | CATG | GAGA | GTAC |
| B-2711 | AGCT | ACGCC | GAGT | GCATA | TCTG | CAGAG | GAGAG | CATG | GAGA | GTAC |
| B-2724 | AGCT | ACGCC | GAGT | GCATA | TCTG | CAGAG | GAGAG | CATG | GAGA | GTAC |
| B-5110 | AGCT | ACGCC | GAGT | GCATA | TCTT | CAGAC | GAGAA | GATG | GGAC | GTAT |
| B-5116 | AGCT | ACGCC | GAGT | GCATA | TCTT | CAGAC | GAGAA | GATG | GGAC | GTAT |
| B-5131 | AGCT | ACGCC | GAGT | GCATA | TCTT | CAGAC | GAGAA | GATG | GGAC | GTAT |
| B-5134 | AGCT | ACGCC | GAGT | GCATA | TCTT | CAGAC | GAGAA | GATG | GGAC | GTAT |
| B-3531 | AGCT | ACGCC | GAGT | GCATA | TCTT | CAGAG | GAGAG | CATG | GGAC | GTAC |

TABLE XI-continued

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-4007 | AGCT | ACGCC | GAGT | GCATA | TCTT | CAGAG | GAGAG | GATG | GGAA | GTAC |
| B-4008 | AGCT | ACGCC | GAGT | GCATA | TCTT | CAGAG | GAGAG | CATG | GGAA | GTAC |
| B-4013 | AGCT | ACGCC | GAGT | GCATA | TCTT | CAGAG | GAGAA | CATG | GGAA | GTAC |
| B-4806 | AGCT | ACGCC | GAGT | GCATA | TCTT | CAGAG | GAGAG | CATG | GAGA | GTAC |
| B-2718 | AGCT | ACGCC | GAGT | GTACC | TCTC | CAGAA | GAGAG | TATG | GAGA | GTAT |
| B-3702 | AGCT | ACGCC | GAGT | GTACC | TCTC | CAGAA | GAGGA | TATG | GGAC | GTAT |
| B-4704 | AGCT | ACGCC | GAGT | GTACC | TCTC | CAGAA | GAGAA | TATG | GGAA | GTAT |
| B-47010101 | AGCT | ACGCC | GAGT | GTACC | TCTC | CAGAG | GAGGA | GATG | GGAA | GTTT |
| B-47010102 | AGCT | ACGCC | GAGT | GTACC | TCTC | CAGAG | GAGGA | GATG | GGAA | GTTT |
| B-4702 | AGCT | ACGCC | GAGT | GTACC | TCTC | CAGAG | GAGAG | GATG | GGAA | GTTT |
| B-4703 | AGCT | ACGCC | GAGT | GTACC | TCTC | CAGAG | GAGAG | GATG | GGAA | GTTT |
| B-2701 | AGCT | ACGCC | GAGT | GTACC | TCTG | CAGAA | GAGAA | TATG | GAGA | GTAT |
| B-2702 | AGCT | ACGCC | GAGT | GTACC | TCTG | CAGAA | GAGAA | TATG | GAGA | GTAT |
| B-2703 | AGCT | ACGCC | GAGT | GTACC | TCTG | CAGAA | GAGGA | TATG | GAGA | GTAT |
| B-270502 | AGCT | ACGCC | GAGT | GTACC | TCTG | CAGAA | GAGGA | TATG | GAGA | GTAT |
| B-270503 | AGCT | ACGCC | GAGT | GTACC | TCTG | CAGAA | GAGGA | TATG | GAGA | GTAT |
| B-270504 | AGCT | ACGCC | GAGT | GTACC | TCTG | CAGAA | GAGGA | TATG | GAGA | GTAT |
| B-270505 | AGCT | ACGCC | GAGT | GTACC | TCTG | CAGAA | GAGGA | TATG | GAGA | GTAT |
| B-270506 | AGCT | ACGCC | GAGT | GTACC | TCTG | CAGAA | GAGGA | TATG | GAGA | GTAT |
| B-2709 | AGCT | ACGCC | GAGT | GTACC | TCTG | CAGAA | GAGGA | TATG | GAGA | GTAT |
| B-2710 | AGCT | ACGCC | GAGT | GTACC | TCTG | CAGAA | GAGGA | TATG | GAGA | GTAT |
| B-2713 | AGCT | ACGCC | GAGT | GTACC | TCTG | CAGAA | GAGGA | TATG | GAGA | GTAT |
| B-2716 | AGCT | ACGCC | GAGT | GTACC | TCTG | CAGAA | GAGGA | TATG | GAGA | GTAT |
| B-2717 | AGCT | ACGCC | GAGT | GTACC | TCTG | CAGAA | GAGGA | TATG | GAGA | GTAT |
| B-2704 | AGCT | ACGCC | GAGT | GTACC | TCTG | CAGAA | GAGAG | TATG | GAGA | GTAT |
| B-2708 | AGCT | ACGCC | GAGT | GTACC | TCTG | CAGAA | GAGAG | TATG | GAGA | GTAT |
| B-2712 | AGCT | ACGCC | GAGT | GTACC | TCTG | CAGAA | GAGAG | TATG | GAGA | GTAT |
| B-2714 | AGCT | ACGCC | GAGT | GTACC | TCTG | CAGAC | GAGGA | GATG | GAGA | GTAT |
| B-2719 | AGCT | ACGCC | GAGT | GTACC | TCTG | CAGAG | GAGGA | GATG | GAGA | GTAC |
| B-2723 | AGCT | ACGCC | GAGT | GTACC | TCTT | CAGAA | GAGAG | TATG | GAGA | GTAT |
| B-0726 | AGCT | ACGCC | GAGT | GCATG | TCTA | CAGAG | GAGAG | CATG | GAGA | GTAC |
| B-4044 | AGCT | ACGCC | GAGT | GCATG | TCTC | CAGAG | GAGAG | GATG | GGAA | GTAT |
| B-4018 | AGCT | ACGCC | GAGT | GCATG | TCTC | CAGAG | GAGAG | CATG | GGAA | GTAC |
| B-4024 | AGCT | ACGCC | GAGT | GCATG | TCTC | CAGAG | GAGAG | CATG | GGAA | GTAC |
| B-4031 | AGCT | ACGCC | GAGT | GCATG | TCTC | CAGAG | GAGAG | CATG | GGAA | GTAC |
| B-4009 | AGCT | ACGCC | GAGT | GCATG | TCTC | CAGAG | GAGAG | CATG | GGAA | GTAC |
| B-4033 | AGCT | ACGCC | GAGT | GCATG | TCTC | CAGAG | GAGAG | GATG | GGAA | GTAC |
| B-4042 | AGCT | ACGCC | GAGT | GCATG | TCTC | CAGAG | GAGAG | GATG | GGAA | GTAC |
| B-2706 | AGCT | ACGCC | GAGT | GCATG | TCTG | CAGAA | GAGAG | TATG | GAGA | GTAT |
| B-2721 | AGCT | ACGCC | GAGT | GCATG | TCTG | CAGAG | GAGAG | GATG | GAGA | GTAC |
| B-5514 | AGCT | CCGCC | ACGT | GCATG | TCTA | CAGGT | GAGAG | GATG | GAGA | GTAT |
| B-1802 | AGCT | CCGCC | ACGT | GCATG | TCTC | CAGAA | GAGAG | TATG | GGAC | GTAT |
| B-1569 | AGCT | CCGCC | ACGT | GCATG | TCTC | CAGAG | GAGAG | GATG | GAGA | GTAT |
| B-1809 | AGCT | CCGCC | ACGT | GCATG | TCTC | CAGAG | GAGAA | GATG | GGAC | GTAC |
| B-1814 | AGCT | CCGCC | ACGT | GCATG | TCTC | CAGAG | GAGAG | CATG | GGAC | GTAC |
| B-180101 | AGCT | CCGCC | ACGT | GCATG | TCTC | CAGAG | GAGAG | GATG | GGAC | GTAC |
| B-180102 | AGCT | CCGCC | ACGT | GCATG | TCTC | CAGAG | GAGAG | GATG | GGAC | GTAC |
| B-1803 | AGCT | CCGCC | ACGT | GCATG | TCTC | CAGAG | GAGAG | GATG | GGAC | GTAC |
| B-1804 | AGCT | CCGCC | ACGT | GCATG | TCTC | CAGAG | GAGAG | GATG | GGAC | GTAC |

TABLE XI-continued

| Position cDNA | 5555 3333 6789 | 44444 12222 90123 | 5555 5666 9012 | 44444 00111 89012 | 2222 6777 9012 | 33333 55666 89012 | 22333 99000 89012 | 3333 6666 3456 | 2222 0000 3456 | 3333 6666 6789 |
|---|---|---|---|---|---|---|---|---|---|---|
| B-1805 | AGCT | CCGCC | ACGT | GCATG | TCTC | CAGAG | GAGAG | GATG | GGAC | GTAC |
| B-1811 | AGCT | CCGCC | ACGT | GCATG | TCTC | CAGAG | GAGAG | GATG | GGAC | GTAC |
| B-1812 | AGCT | CCGCC | ACGT | GCATG | TCTC | CAGAG | GAGAG | GATG | GGAC | GTAC |
| B-1815 | AGCT | CCGCC | ACGT | GCATG | TCTC | CAGAG | GAGAG | GATG | GGAC | GTAC |
| B-1817N | AGCT | CCGCC | ACGT | GCATG | TCTC | CAGAG | GAGAG | GATG | GGAC | GTAC |
| B-1808 | AGCT | CCGCC | ACGT | GCATG | TCTC | CAGAG | GAGAG | GATG | GGAC | GTGC |
| B-1818 | AGCT | CCGCC | ACGT | GCATG | TCTC | CAGAG | GAGAG | GATG | GGAC | GTCT |
| B-1806 | AGCT | CCGCC | ACGT | GCATG | TCTC | CAGAG | GTGAG | GATG | GGAC | GTAC |
| B-3907 | AGCT | CCGCC | ACGT | GCATG | TCTG | CAGAG | GAGAG | GATG | GAGA | GTAC |
| B-1544 | AGCT | CCGCC | ACGT | GTATG | TCTG | CAGAG | GAGAG | GATG | GGAT | GTAT |
| B-1807 | AGCT | CCGCC | ACGT | GCATG | TCTT | CAGAG | GAGAG | GATG | GGAC | GTAC |
| B-3535 | AGCT | CCGCC | ACGT | GCATG | TCTT | CAGAG | GAGAG | GATG | GGAC | GTAT |
| B-5805 | AGCT | CCGCC | ACGT | GCATG | ACAT | CAGAG | GAGAA | GATG | GGAC | GTAT |
| B-5609 | AGCT | CCGCC | CTGT | GCATG | TCTA | CAGAG | GAGAG | GATG | GAGA | GTAT |
| B-1304 | AGCT | CCGCC | CTGT | GCATG | TCTC | CAGAC | GAGAA | GATG | GGAT | GTAT |
| B-5309 | AGCT | CCGCC | CTGT | GCATG | TCTC | CAGAG | GAGAA | GATG | GGAC | GTAT |
| B-1503 | AGCT | CCGCC | CTGT | GCATG | TCTC | CAGAG | GAGAG | GATG | GAGA | GTAC |
| B-1561 | AGCT | CCGCC | CTGT | GCATG | TCTC | CAGAG | GAGAG | GATG | GAGA | GTAC |
| B-1564 | AGCT | CCGCC | CTGT | GCATG | TCTC | CAGAG | GAGAG | GATG | GAGA | GTAC |
| B-1574 | AGCT | CCGCC | CTGT | GCATG | TCTC | CAGAG | GAGAG | GATG | GAGA | GTAC |
| B-1505 | AGCT | CCGCC | CTGT | GCATG | TCTC | CAGAG | GAGAG | GATG | GGAT | GTAC |
| B-1539 | AGCT | CCGCC | CTGT | GCATG | TCTC | CAGAG | GAGAG | GATG | GGAT | GTAC |
| B-1562 | AGCT | CCGCC | CTGT | GCATG | TCTC | CAGAG | GAGAG | GATG | GAGA | GTAT |
| B-4802 | AGCT | CCGCC | CTGT | GCATG | TCTC | CAGAG | GAGAG | GATG | GAGA | GTAT |
| B-1520 | AGCT | CCGCC | CTGT | GCATG | TCTC | CAGAG | GAGAG | GATG | GGAT | GTAT |
| B-3520 | AGCT | CCGCC | CTGT | GCATG | TCTC | CAGAG | GAGAG | GATG | GGAC | GTAT |
| B-3528 | AGCT | CCGCC | CTGT | GCATG | TCTC | CAGAG | GAGAG | GATG | GGAC | GTAT |
| B-1531 | AGCT | CCGCC | CTGT | GTATG | TCTC | CAGAG | GAGAG | GATG | GGAT | GTAC |
| B-1555 | AGCT | CCGCC | CTGT | GTATG | TCTC | CAGAG | GAGAG | CATG | GGAT | GTAC |
| B-1513 | AGCT | CCGCC | CTGT | GTATG | TCTC | CAGAG | GAGAA | GATG | GGAT | GTAT |
| B-1536 | AGCT | CCGCC | CTGT | GTATG | TCTC | CAGAG | GAGAA | GATG | GGAT | GTAT |
| B-1502 | AGCT | CCGCC | CTGT | GTATG | TCTC | CAGAG | GAGAG | GATG | GGAT | GTAT |
| B-1525 | AGCT | CCGCC | CTGT | GTATG | TCTC | CAGAG | GAGAG | GATG | GGAT | GTAT |
| B-1506 | AGCT | CCGCC | CTGT | GTATG | TCTC | CAGAG | GAGAG | GATG | GGAT | GTTT |
| B-1523 | AGCT | CCGCC | CTGT | GCATG | TCTG | CAGAG | GAGAA | GATG | GAGA | GTAC |
| B-1518 | AGCT | CCGCC | CTGT | GCATG | TCTG | CAGAG | GAGAG | GATG | GAGA | GTAC |
| B-1572 | AGCT | CCGCC | CTGT | GCATG | TCTG | CAGAG | GAGAG | GATG | GAGA | GTAC |
| B-3526 | AGCT | CCGCC | CTGT | GCATG | TCTG | CAGAG | GAGAG | GATG | GAGA | GTAT |
| B-1521 | AGCT | CCGCC | CTGT | GTATG | TCTG | CAGAG | GAGAG | GATG | GGAT | GTAT |
| B-1516 | AGCT | CCGCC | CTGT | GCATG | ACAT | CAGAG | GAGAA | GATG | GGAT | GTAT |
| B-1567 | AGCT | CCGCC | CTGT | GCATG | ACAT | CAGAG | GAGAA | GATG | GGAT | GTAT |
| B-3537 | AGCT | CCGCC | CTGT | GCATG | TCTT | CAGAC | GAGAG | GATG | GGAC | GTAT |
| B-1529 | AGCT | CCGCC | CTGT | GCATG | TCTT | CAGAG | GAGAG | GATG | GAGA | GTAC |
| B-3505 | AGCT | CCGCC | CTGT | GCATG | TCTT | CAGAG | GAGAG | CATG | GGAC | GTAC |
| B-3516 | AGCT | CCGCC | CTGT | GCATG | TCTT | CAGAG | GAGAG | CATG | GGAC | GTAC |
| B-3517 | AGCT | CCGCC | CTGT | GCATG | TCTT | CAGAG | GAGAG | CATG | GGAC | GTAC |
| B-3530 | AGCT | CCGCC | CTGT | GCATG | TCTT | CAGAG | GAGAG | CATG | GGAC | GTAC |

TABLE XI-continued

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-3532 | AGCT | CCGCC | CTGT | GCATG | TCTT | CAGAG | GAGAG | GATG | GGAC | GTAC |
| B-3527 | AGCT | CCGCC | CTGT | GCATG | TCTT | CAGAG | GAGAA | GATG | GGAC | GTAT |
| B-5301 | AGCT | CCGCC | CTGT | GCATG | TCTT | CAGAG | GAGAA | GATG | GGAC | GTAT |
| B-5302 | AGCT | CCGCC | CTGT | GCATG | TCTT | CAGAG | GAGAA | GATG | GGAC | GTAT |
| B-5306 | AGCT | CCGCC | CTGT | GCATG | TCTT | CAGAG | GAGAA | GATG | GGAC | GTAT |
| B-5308 | AGCT | CCGCC | CTGT | GCATG | TCTT | CAGAG | GAGAA | GATG | GGAC | GTAT |
| B-5303 | AGCT | CCGCC | CTGT | GCATG | TCTT | CAGAG | GAGGA | CATG | GGAC | GTAT |
| B-3519 | AGCT | CCGCC | CTGT | GCATG | TCTT | CAGAG | GAGAG | CATG | GGAA | GTAT |
| B-3525 | AGCT | CCGCC | CTGT | GCATG | TCTT | CAGAG | GAGAG | GATG | GAGA | GTAT |
| B-350101 | AGCT | CCGCC | CTGT | GCATG | TCTT | CAGAG | GAGAG | GATG | GGAC | GTAT |
| B-350102 | AGCT | CCGCC | CTGT | GCATG | TCTT | CAGAG | GAGAG | GATG | GGAC | GTAT |
| B-3507 | AGCT | CCGCC | CTGT | GCATG | TCTT | CAGAG | GAGAG | GATG | GGAC | GTAT |
| B-3510 | AGCT | CCGCC | CTGT | GCATG | TCTT | CAGAG | GAGAG | GATG | GGAC | GTAT |
| B-3511 | AGCT | CCGCC | CTGT | GCATG | TCTT | CAGAG | GAGAG | GATG | GGAC | GTAT |
| B-3521 | AGCT | CCGCC | CTGT | GCATG | TCTT | CAGAG | GAGAG | GATG | GGAC | GTAT |
| B-3524 | AGCT | CCGCC | CTGT | GCATG | TCTT | CAGAG | GAGAG | GATG | GGAC | GTAT |
| B-3529 | AGCT | CCGCC | CTGT | GCATG | TCTT | CAGAG | GAGAG | GATG | GGAC | GTAT |
| B-3540N | AGCT | CCGCC | CTGT | GCATG | TCTT | CAGAG | GAGAG | GATG | GGAC | GTAT |
| B-3541 | AGCT | CCGCC | CTGT | GCATG | TCTT | CAGAG | GAGAG | GATG | GGAC | GTAT |
| B-3542 | AGCT | CCGCC | CTGT | GCATG | TCTT | CAGAG | GAGAG | GATG | GGAC | GTAT |
| B-5305 | AGCT | CCGCC | CTGT | GCATG | TCTT | CAGAG | GAGAG | GATG | GGAC | GTAT |
| B-3523 | AGCT | CCGCC | CTGT | GCATG | TCTT | CAGAG | GAGAG | GATG | GGAC | GTTT |
| B-3546 | AGCT | CCGCC | CTGT | GCATG | TCTT | CAGAG | GAGAG | GATG | GGAT | GTAT |
| B-5801 | AGCT | CCGCC | CTGT | GCATG | ACAT | CAGAG | GAGAA | GATG | GGAC | GTAT |
| B-5804 | AGCT | CCGCC | CTGT | GCATG | ACAT | CAGAG | GAGAA | GATG | GGAC | GTAT |
| B-5809 | AGCT | CCGCC | CTGT | GCATG | ACAT | CAGAG | GAGAA | GATG | GGAC | GTAT |
| B-5802 | AGCT | CCGCC | CTGT | GCATG | ACAT | CAGTG | GAGAA | GATG | GGAC | GTAT |
| B-5806 | AGCT | CCGCC | CTGT | GCATG | ACAT | CAGTG | GAGAA | GATG | GGAC | GTAT |
| B-5807 | AGCT | CCGCC | CTGT | GCATG | ACAT | CAGTG | GAGAA | GATG | GGAC | GTAT |
| B-570101 | AGCT | CCGCC | CTGT | GCATG | ACAT | CAGGT | GAGAA | GATG | GGAT | GTAT |
| B-5706 | AGCT | CCGCC | CTGT | GCATG | ACAT | CAGGT | GAGAA | GATG | GGAT | GTAT |
| B-5708 | AGCT | CCGCC | CTGT | GCATG | ACAT | CAGGT | GAGAA | GATG | GGAT | GTAT |
| B-1310 | AGCT | CCGCC | GAGT | GTATG | TCTC | CAGAG | GAGAA | GATG | GGAT | GTAC |
| B-1540 | AGCT | CCGCC | GAGT | GCATG | TCTC | CAGAG | GAGAG | GATG | GGAT | GTAC |
| B-1810 | AGCT | CCGCC | GAGT | GCATG | TCTC | CAGAG | GAGAG | GATG | GGAC | GTAC |
| B-4003 | AGCT | CCGCC | GAGT | GCATG | TCTC | CAGAG | GAGAG | CATG | GGAA | GTAC |
| B-4020 | AGCT | CCGCC | GAGT | GCATG | TCTC | CAGAG | GAGAG | GATG | GGAA | GTAC |
| B-1552 | AGCT | CCGCC | GAGT | GCATG | TCTG | CAGAG | GAGAG | GATG | GAGA | GTAC |
| B-4038 | AGCT | CCGCC | GAGT | GCATA | TCTC | CAGAG | GAGAG | GATG | GGAA | GTAC |
| B-3515 | AGCT | CCGCC | GAGT | GCATG | TCTT | CAGAG | GAGAG | GATG | GGAC | GTAT |
| B-570102 | AGCT | CTGCC | CTGT | GCATG | ACAT | CAGGT | GAGAA | GATG | GGAT | GTAT |
| B-1306 | AGCT | TAGCC | ACTG | GCATA | TCTC | CAGAG | GAGAA | GATG | GGAT | GTAT |
| B-1542 | AGCT | TAGCC | ACTG | GCATA | TCTC | CAGAC | GAGAG | GATG | GGAT | GTAT |
| B-5512 | AGCT | TAGCC | ACTG | GCATA | TCTA | CAGAC | GAGAA | GATG | GAGA | GTAT |
| B-5501 | AGCT | TAGCC | ACTG | GCATA | TCTA | CAGAC | GAGAG | GATG | GAGA | GTAT |
| B-5502 | AGCT | TAGCC | ACTG | GCATA | TCTA | CAGAC | GAGAG | GATG | GAGA | GTAT |
| B-5505 | AGCT | TAGCC | ACTG | GCATA | TCTA | CAGAC | GAGAG | GATG | GAGA | GTAT |
| B-5510 | AGCT | TAGCC | ACTG | GCATA | TCTA | CAGAC | GAGAG | GATG | GAGA | GTAT |
| B-5516 | AGCT | TAGCC | ACTG | GCATA | TCTA | CAGAC | GAGAG | GATG | GAGA | GTAT |
| B-5401 | AGCT | TAGCC | ACTG | GCATA | TCTA | CAGAC | GAGAG | GATG | GAGG | GTAT |
| B-5402 | AGCT | TAGCC | ACTG | GCATA | TCTA | CAGAC | GAGAG | GATG | GAGG | GTAT |

TABLE XI-continued

| Position cDNA | 5555<br>3333<br>6789 | 44444<br>12222<br>90123 | 5555<br>5666<br>9012 | 44444<br>00111<br>89012 | 2222<br>6777<br>9012 | 33333<br>55666<br>89012 | 22333<br>99000<br>89012 | 3333<br>6666<br>3456 | 2222<br>0000<br>3456 | 3333<br>6666<br>6789 |
|---|---|---|---|---|---|---|---|---|---|---|
| B-5507 | AGCT | TAGCC | ACTG | GCATA | TCTA | CAGAC | GAGAG | GATG | GAGG | GTAT |
| B-5503 | AGCT | TAGCC | ACTG | GCATA | TCTA | CAGAC | GTGAG | GATG | GAGA | GTAT |
| B-3917 | AGCT | TAGCC | ACTG | GTATA | TCTA | CAGAG | GAGAG | GATG | GAGA | GTAC |
| B-5610 | AGCT | TAGCC | ACTG | GCATA | TCTA | CAGAG | GAGAG | GATG | GAGA | GTAC |
| B-5511 | AGCT | TAGCC | ACTG | GCATA | TCTA | CAGAT | GAGAG | GATG | GAGA | GTAT |
| B-5901 | AGCT | TAGCC | ACTG | GCATA | TCTA | CAGAC | GAGAA | GATG | GAGA | GTAT |
| B-1303 | AGCT | TAGCC | CTGT | GCATA | TCTC | CAGAC | GAGAA | GATG | GGAT | GTAT |
| B-4410 | AGCT | TAGCC | CTGT | GCATA | TCTC | CAGAG | GAGAA | GATG | GGAA | GTTT |
| B-4901 | AGCT | TAGCC | CTGT | GTATA | TCTC | CAGAG | GAGAA | GATG | GGAA | GTAT |
| B-4902 | AGCT | TAGCC | CTGT | GTATA | TCTC | CAGAG | GAGAA | GATG | GGAA | GTAT |
| B-4903 | AGCT | TAGCC | CTGT | GTATA | TCTC | CAGAG | GAGAA | GATG | GGAC | GTAT |
| B-5001 | AGCT | TAGCC | CTGT | GTATA | TCTC | CAGAG | GAGAG | GATG | GGAA | GTAT |
| B-5002 | AGCT | TAGCC | CTGT | GTATA | TCTC | CAGAG | GAGAG | GATG | GGAA | GTAT |
| B-5004 | AGCT | TAGCC | CTGT | GTATA | TCTC | CAGAG | GAGAG | GATG | GGAA | GTAC |
| B-5115 | AGCT | TAGCC | CTGT | GCATA | TCTT | CAGAC | GAGAA | GATG | GGAC | GTAT |
| B-5601 | AGCT | TAGCC | CTGT | GCATA | TCTA | CAGAC | GAGAG | GATG | GAGA | GTAT |
| B-5607 | AGCT | TAGCC | CTGT | GCATA | TCTA | CAGAC | GAGAA | GATG | GAGA | GTAT |
| B-5602 | AGCT | TAGCC | CTGT | GCATA | TCTA | CAGAG | GAGAG | GATG | GAGA | GTAC |
| B-5604 | AGCT | TAGCC | CTGT | GCATA | TCTA | CAGAG | GAGAG | GATG | GAGA | GTAC |
| B-5608 | AGCT | TAGCC | CTGT | GCATA | AGTA | CAGAC | GAGAG | GATG | GAGA | GTAT |
| B-1302 | AGCT | TAGCC | GAGT | GCATA | TCTC | CAGAC | GAGAA | GATG | GGAT | GTAT |
| B-1308 | AGCT | TAGCC | GAGT | GCATA | TCTC | CAGAC | GAGAA | GATG | GGAT | GTAT |
| B-1309 | AGCT | TAGCC | GAGT | GCATA | TCTC | CAGAC | GAGAG | GATG | GGAT | GTAT |
| B-1301 | AGCT | TAGCC | GAGT | GCATA | TCTC | CAGAG | GAGAA | GATG | GGAT | GTAT |
| B-1307N | AGCT | TAGCC | GAGT | GCATA | TCTC | CAGAG | GAGAA | GATG | GGAT | GTAT |
| B-1311 | AGCT | TAGCC | GAGT | GCATA | TCTC | CAGAG | GAGAA | GATG | GGAT | GTAC |
| B-4048 | AGCT | TAGCC | GAGT | GCATA | TCTC | CAGAG | GAGAG | GATG | GGAA | GTAC |
| B-1401 | AGCT | TCGCC | ACGT | GTATA | TCTG | CAGTG | GAGAG | GATG | GAGA | GTAT |
| B-1402 | AGCT | TCGCC | ACGT | GTATA | TCTG | CAGTG | GAGAG | GATG | GAGA | GTAT |
| B-1404 | AGCT | TCGCC | ACGT | GTATA | ACTG | CAGTG | GAGAG | GATG | GAGA | GTAT |
| B-1405 | AGCT | TCGCC | ACGT | GTATA | TCTG | CAGAG | GAGAG | CATG | GAGA | GTAC |
| B-140601 | AGCT | TCGCC | ACGT | GTATA | TCTG | CAGAG | GAGAG | GATG | GAGA | GTAC |
| B-140602 | AGCT | TCGCC | ACGT | GTATA | TCTG | CAGAG | GAGAG | GATG | GAGA | GTAT |
| B-3916 | AGCT | TCGCC | ACGT | GCATA | TCTA | CACAG | GAGAG | GATG | GAGA | GTAC |
| B-5513 | AGCT | TCGCC | ACGT | GCATA | TCTA | CAGAC | GAGAG | GATG | GAGA | GTAT |
| B-3920 | AGCT | TCGCC | ACGT | GCATA | TCTA | CAGAG | GAGAA | GATG | GAGA | GTAC |
| B-3910 | AGCT | TCGCC | ACGT | GCATA | TCTA | CAGAG | GAGAG | GATG | GAGA | GTAC |
| B-670101 | AGCT | TCGCC | ACGT | GCATA | TCTA | CAGAG | GAGAG | GATG | GAGA | GTAC |
| B-670102 | AGCT | TCGCC | ACGT | GCATA | TCTA | CAGAG | GAGAG | GATG | GAGA | GTAC |
| B-6702 | AGCT | TCGCC | ACGT | GCATA | AGTA | CAGAG | GTGAG | GATG | GAGG | GTAC |
| B-3803 | AGCT | TCGCC | ACGT | GCATA | TCTC | CAGAG | GAGAG | GATG | GAGA | GTAC |
| B-390201 | AGCT | TCGCC | ACGT | GCATA | TCTC | CAGAG | GAGAG | GATG | GAGA | GTAC |
| B-390202 | AGCT | TCGCC | ACGT | GCATA | TCTC | CAGAG | GAGAG | GATG | GAGA | GTAC |
| B-3913 | AGCT | TCGCC | ACGT | GCATA | TCTC | CAGAG | GAGAG | GATG | GAGA | GTAC |

TABLE XI-continued

| Position cDNA | 5555 3333 6789 | 44444 12222 90123 | 5555 5666 9012 | 44444 00111 89012 | 2222 6777 9012 | 33333 55666 89012 | 22333 99000 89012 | 3333 6666 3456 | 2222 0000 3456 | 3333 6666 6789 |
|---|---|---|---|---|---|---|---|---|---|---|
| B-3923 | AGCT | TCGCC | ACGT | GCATA | TCTC | CAGAG | GAGAG | GATG | GAGA | GTAC |
| B-390601 | AGCT | TCGCC | ACGT | GCATA | TCTG | CAGAC | GAGAG | GATG | GAGA | GTAC |
| B-3928 | AGCT | TCGCC | ACGT | GCATA | TCTG | CAGAC | GAGAG | GATG | GAGA | GTAC |
| B-390602 | AGCT | TCGCC | ACGT | GCATA | TCTG | CAGAC | GAGAG | GATG | GAGA | GTAT |
| B-3801 | AGCT | TCGCC | ACGT | GCATA | TCTG | CAGAG | GAGAA | GATG | GAGA | GTAC |
| B-380201 | AGCT | TCGCC | ACGT | GCATA | TCTG | CAGAG | GAGAA | GATG | GAGA | GTAC |
| B-380202 | AGCT | TCGCC | ACGT | GCATA | TCTG | CAGAG | GAGAA | GATG | GAGA | GTAC |
| B-3804 | AGCT | TCGCC | ACGT | GCATA | TCTG | CAGAG | GAGAA | GATG | GAGA | GTAC |
| B-3805 | AGCT | TCGCC | ACGT | GCATA | TCTG | CAGAG | GAGAA | GATG | GAGA | GTAC |
| B-3809 | AGCT | TCGCC | ACGT | GCATA | TCTG | CAGAG | GAGAA | GATG | GAGA | GTAC |
| B-3924 | AGCT | TCGCC | ACGT | GCATA | TCTG | CAGAG | GAGAG | CACG | GAGA | GTAC |
| B-3903 | AGCT | TCGCC | ACGT | GCATA | TCTG | CAGAG | GAGAG | CATG | GAGA | GTAC |
| B-390101 | AGCT | TCGCC | ACGT | GCATA | TCTG | CAGAG | GAGAG | GATG | GAGA | GTAC |
| B-390103 | AGCT | TCGCC | ACGT | GCATA | TCTG | CAGAG | GAGAG | GATG | GAGA | GTAC |
| B-390104 | AGCT | TCGCC | ACGT | GCATA | TCTG | CAGAG | GAGAG | GATG | GAGA | GTAC |
| B-3904 | AGCT | TCGCC | ACGT | GCATA | TCTG | CAGAG | GAGAG | GATG | GAGA | GTAC |
| B-3905 | AGCT | TCGCC | ACGT | GCATA | TCTG | CAGAG | GAGAG | GATG | GAGA | GTAC |
| B-3912 | AGCT | TCGCC | ACGT | GCATA | TCTG | CAGAG | GAGAG | GATG | GAGA | GTAC |
| B-3922 | AGCT | TCGCC | ACGT | GCATA | TCTG | CAGAG | GAGAG | GATG | GAGA | GTAC |
| B-3922 | AGCT | TCGCC | ACGT | GCATA | TCTG | CAGAG | GAGAG | GATG | GAGA | GTAC |
| B-3925N | AGCT | TCGCC | ACGT | GCATA | TCTG | CAGAG | GAGAG | GATG | GAGA | GTAC |
| B-3926 | AGCT | TCGCC | ACGT | GCATA | TCTG | CAGAG | GAGAG | GATG | GAGA | GTAC |
| B-3915 | AGCT | TCGCC | ACGT | GCATG | TCTG | CAGAG | GAGAG | GATG | GAGA | GTAC |
| B-3909 | AGCT | TCGCC | ACGT | GCATA | TCTG | CAGAG | GAGAG | GATG | GAGA | GTCT |
| B-3919 | AGCT | TCGCC | ACGT | GCATA | TCTG | CAGAG | GAGAG | GATG | GGAC | GTAC |
| B-3927 | AGCT | TCGCC | ACGT | GCATA | TCTG | CAGAG | GTGAG | GATG | GAGA | GTAC |
| B-3806 | AGCT | TCGCC | ACGT | GCATA | TCTT | CAGAG | GAGAA | GATG | GGAC | GTAC |
| B-3807 | AGCT | TCGCC | ACGT | GCATA | TCTT | CAGAG | GAGAA | GATG | GGAC | GTAC |
| B-3808 | AGCT | TCGCC | ATGT | GCATA | TCTG | CAGAG | GAGAA | GATG | GAGA | GTAC |
| B-511301 | AGCT | TCGCC | CTGT | GCATA | TCTT | CAGAC | GAGAA | GATG | GGAC | GTAT |
| B-511302 | AGCT | TCGCC | CTGT | GCATA | TCTT | CAGAC | GAGAA | GATG | GGAC | GTAT |
| B-3506 | AGCT | TCGCC | CTGT | GCATA | TCTT | CAGAG | GAGAG | GATG | GGAC | GTAT |
| B-5307 | AGCT | TCGCC | CTGT | GTATA | TCTT | CAGAG | GAGAA | GATG | GGAC | GTCT |
| B-3503 | AGCT | TCGCC | CTGT | GCATG | TCTT | CAGAG | GAGAG | GATG | GGAC | GTAT |
| B-3513 | AGCT | TCGCC | CTGT | GCATG | TCTT | CAGAG | GAGAG | GATG | GGAC | GTAT |
| B-3536 | AGCT | TCGCC | CTGT | GCATG | TCTT | CAGAG | GAGAG | GATG | GGAC | GTAT |
| B-5304 | AGCT | TCGCC | CTGT | GCATG | TCTT | CAGAG | GAGAA | GATG | GGAC | GTAT |
| B-5611 | AGCT | TCGCC | CTGT | GCATG | TCTA | CAGAG | GAGAG | GATG | GAGA | GTAT |
| B-3533 | AGCT | TCGCC | GAGT | GCATG | TCTT | CAGAG | GAGAG | GATG | GGAC | GTAT |
| B-4036 | AGCT | TCGCC | GAGT | GCATA | TCTC | CAGAG | GAGAG | GATG | GGAA | GTAC |
| B-4807 | AGCT | TCGCC | GAGT | GCATA | TCTC | CAGAG | GAGAG | CATG | GAGA | GTAC |
| B-7301 | AGCT | TCGCC | GAGT | GTATA | TCTG | CAGAC | GTGGG | GATG | GAGA | GTAT |

TABLE XII

| Position cDNA | 1111 2222 5678 | 1111 9999 3456 | 1112 9990 7890 | 2222 2222 4567 | 2222 6666 1234 | 2222 8888 3456 | 2222 9999 6789 | 3333 0011 8901 | 3333 3344 8901 | 3333 4444 2345 |
|---|---|---|---|---|---|---|---|---|---|---|
| DRB1-070101 | ATAA | GAGT | TCGT | AGTA | CGAG | GACA | ACAG | AGGT | GGGT | TGGT |
| DRB1-070102 | ATAA | GAGT | TCGT | AGTA | CGAG | GACA | ACAG | AGGT | GGGT | TGGT |

TABLE XII-continued

| Position cDNA | 1111<br>2222<br>5678 | 1111<br>9999<br>3456 | 1112<br>9990<br>7890 | 2222<br>2222<br>4567 | 2222<br>6666<br>1234 | 2222<br>8888<br>3456 | 2222<br>9999<br>6789 | 3333<br>0011<br>8901 | 3333<br>3344<br>8901 | 3333<br>4444<br>2345 |
|---|---|---|---|---|---|---|---|---|---|---|
| DRB1-0703 | ATAA | GAGT | TCGT | AGTA | CGAG | GACA | ACAG | AGGT | GGGT | TGGT |
| DRB1-0704 | ATAA | GAGT | TCGT | AGTA | CGAG | GACA | ACAG | AGGT | GGGT | TGGT |
| DRB1-0705 | ATAA | GAGT | TCGT | AGTA | CGAG | GACA | ACAG | AGGT | GGGT | TGGT |
| DRB1-0707 | ATAA | GAGT | TCGT | AGTA | CGAG | GACA | ACAG | AGGT | GGGT | TGGT |
| DRB1-0706 | ATAA | GAGT | TCGT | AGTA | CGAG | GACA | ACAG | AGGT | GGGT | TGGT |
| DRB1-0708 | ATAA | GAGG | TCGT | AGTA | CGAG | GACA | ACAG | AGGT | GGGT | TGGT |
| DRB1-0441 | ATGA | GAGA | ACGT | AGTA | CGAG | GACC | AGAG | AGGT | GGGT | TGTG |
| DRB1-0439 | ATGA | GAGT | ACGT | ACTA | CGAG | GACC | AGAG | AGGT | GGGT | TGTG |
| DRB1-0416 | ATGA | GAGT | ACGT | AGTA | CCAG | GACC | AGAA | CGGT | GGGT | TGGT |
| DRB1-0402 | ATGA | GAGT | ACGT | AGTA | CGAG | GACA | ACGA | CGGT | GGGT | TGTG |
| DRB1-0412 | ATGA | GAGT | ACGT | AGTA | CGAG | GACA | ACAG | TGGT | GGGT | TGTG |
| DRB1-0418 | ATGA | GAGT | ACGT | AGTA | CGAG | GACA | ACAG | TGGT | GGGT | TGTG |
| DRB1-0414 | ATGA | GAGT | ACGT | AGTA | CGAG | GACA | ACGA | CGGT | GGGT | TGGT |
| DRB1-0438 | ATGA | GAGT | ACGT | AGTA | CGAG | GACA | AGAA | CGGT | GGGT | TGGT |
| DRB1-0413 | ATGA | GAGT | ACGT | AGTA | CGAG | GACC | AGAA | CGGT | GGGT | TGTG |
| DRB1-0422 | ATGA | GAGT | ACGT | AGTA | CGAG | GACC | AGAA | GGGT | GGGT | TGTG |
| DRB1-040101 | ATGA | GAGT | ACGT | AGTA | CGAG | GACC | AGAA | CGGT | GGGT | TGGT |
| DRB1-040102 | ATGA | GAGT | ACGT | AGTA | CGAG | GACC | AGAA | CGGT | GGGT | TGGT |
| DRB1-0409 | ATGA | GAGT | ACGT | AGTA | CGAG | GACC | AGAA | CGGT | GGGT | TGGT |
| DRB1-0426 | ATGA | GAGT | ACGT | AGTA | CGAG | GACC | AGAA | CGGT | GGGT | TGGT |
| DRB1-0433 | ATGA | GAGT | ACGT | AGTA | CGAG | GACC | AGAA | CGGT | GGGT | TGGT |
| DRB1-0437 | ATGA | GAGT | ACGT | AGTA | CGAG | GACC | ACGA | CGGT | GGGT | TGTG |
| DRB1-040301 | ATGA | GAGT | ACGT | AGTA | CGAG | GACC | AGAG | AGGT | GGGT | TGTG |
| DRB1-0411 | ATGA | GAGT | ACGT | AGTA | CGAG | GACC | AGAG | AGGT | GGGT | TGTG |
| DRB1-0427 | ATGA | GAGT | ACGT | AGTA | CGAG | GACC | AGAG | AGGT | GGGC | TGTG |
| DRB1-040701 | ATGA | GAGT | ACGT | AGTA | CGAG | GACC | AGAG | AGGT | GGGT | TGGT |
| DRB1-040702 | ATGA | GAGT | ACGT | AGTA | CGAG | GACC | AGAG | AGGT | GGGT | TGGT |
| DRB1-040703 | ATGA | GAGT | ACGT | AGTA | CGAG | GACC | AGAG | AGGT | GGGT | TGGT |
| DRB1-0417 | ATGA | GAGT | ACGT | AGTA | CGAG | GACC | AGAG | AGGT | GGGT | TGGT |
| DRB1-0404 | ATGA | GAGT | ACGT | AGTA | CGAG | GACC | AGAG | CGGT | GGGT | TGTG |
| DRB1-0410 | ATGA | GAGT | ACGT | AGTA | CGAG | GACC | AGAG | CGGT | GGGT | TGTG |
| DRB1-0423 | ATGA | GAGT | ACGT | AGTA | CGAG | GACC | AGAG | CGGT | GGGT | TGTG |
| DRB1-0432 | ATGA | GAGT | ACGT | AGTA | CGAG | GACC | AGAG | CGGT | GGGT | TGTG |
| DRB1-0440 | ATGA | GAGT | ACGT | AGTA | CGAG | GACC | AGAG | CGGT | GGGT | TGTG |
| DRB1-0444 | ATGA | GAGT | ACGT | AGTA | CGAG | GACC | AGAG | CGGT | GGGT | TGTG |
| DRB1-040501 | ATGA | GAGT | ACGT | AGTA | CGAG | GACC | AGAG | CGGT | GGGT | TGGT |
| DRB1-040502 | ATGA | GAGT | ACGT | AGTA | CGAG | GACC | AGAG | CGGT | GGGT | TGGT |
| DRB1-040503 | ATGA | GAGT | ACGT | AGTA | CGAG | GACC | AGAG | CGGT | GGGT | TGGT |
| DRB1-040504 | ATGA | GAGT | ACGT | AGTA | CGAG | GACC | AGAG | CGGT | GGGT | TGGT |
| DRB1-0408 | ATGA | GAGT | ACGT | AGTA | CGAG | GACC | AGAG | CGGT | GGGT | TGGT |
| DRB1-0429 | ATGA | GAGT | ACGT | AGTA | CGAG | GACC | AGAG | CGGT | GGGT | TGGT |
| DRB1-0430 | ATGA | GAGT | ACGT | AGTA | CGAG | GACC | AGAG | CGGT | GGGT | TGGT |
| DRB1-0445 | ATGA | GAGT | ACGT | AGTA | CGAG | GACC | AGAG | CGGT | GGGT | TGGT |
| DRB1-0448 | ATGA | GAGT | ACGT | AGTA | CGAG | GACC | AGAG | CGGT | GGGT | TGGT |
| DRB1-0431 | ATGA | GAGT | ACGT | AGTA | CGAG | GACC | AGAG | TGGT | GGGT | TGGT |
| DRB1-0424 | ATGA | GAGT | ACGT | AGTA | CGAG | GACC | GGAG | CGGT | GGGT | TGGT |
| DRB1-0425 | ATGA | GAGT | ACGT | AGTA | CGAG | GACT | ACAG | TGGT | GGGT | TGTG |
| DRB1-0436 | ATGA | GAGT | ACGT | AGTA | CGAG | GACT | ACAG | CGGT | GGGT | TGTG |
| DRB1-0447 | ATGA | GAGT | ACGT | AGTA | CGAG | GACT | ACAG | CGGT | GGGT | TGGT |
| DRB1-0415 | ATGA | GAGT | ACGT | AGTA | GGAG | GACT | ACAG | CGGT | GGGT | TGTG |

TABLE XII-continued

| Position cDNA | 1111<br>2222<br>5678 | 1111<br>9999<br>3456 | 1112<br>9990<br>7890 | 2222<br>2222<br>4567 | 2222<br>6666<br>1234 | 2222<br>8888<br>3456 | 2222<br>9999<br>6789 | 3333<br>0011<br>8901 | 3333<br>3344<br>8901 | 3333<br>4444<br>2345 |
|---|---|---|---|---|---|---|---|---|---|---|
| DRB1-040302 | ATGA | GAGT | ACGT | AGTA | TGAG | GACC | AGAG | AGGT | GGGT | TGTG |
| DRB1-0435 | ATGA | GAGT | ACGT | AGTT | CGAG | GACC | AGAA | CGGT | GGGT | TGGT |
| DRB1-0442 | ATGA | GAGT | ACGT | AGTT | CGAG | GACC | AGAG | CGGT | GGGT | TGTG |
| DRB1-0428 | ATGA | GAGT | ACGT | AGTT | CGAG | GACC | AGAG | CGGT | GGGT | TGGT |
| DRB1-0443 | ATGA | GAGT | ACGT | AGTT | CGAG | GACC | AGAG | CGGT | GGGT | TGGT |
| DRB1-1122 | ATGA | GAGT | ACGT | AGTT | GGAG | GACT | ACAG | CGGT | GGGT | TGGT |
| DRB1-0406 | ATGA | GAGT | CCGT | AGTA | CGAG | GACC | AGAG | AGGT | GGGT | TGTG |
| DRB1-0446 | ATGA | GAGT | CCGT | AGTA | CGAG | GACC | AGAG | AGGT | GGGT | TGTG |
| DRB1-0420 | ATGA | GAGT | CCGT | AGTA | CGAG | GACC | AGAG | AGGT | GGGT | TGGT |
| DRB1-0421 | ATGA | GAGT | CCGT | AGTA | CGAG | GACC | AGAA | CGGT | GGGT | TGGT |
| DRB1-0419 | ATGA | GAGT | CCGT | AGTA | CGAG | GACC | AGAG | CGGT | GGGT | TGGT |
| DRB1-1410 | ATGA | GAGT | TCGT | AGTA | GGAG | GACC | GGAG | AGGT | GGGT | TGTG |
| DRB1-1332 | CTGA | GAGA | ACGT | AGTA | CGAG | GACA | ACGA | CGGT | GGGT | TGTG |
| DRB1-1340 | CTGA | GAGA | ACGT | AGTA | CGAG | GACA | ACGA | CGGT | GGGT | TGTG |
| DRB1-1353 | CTGA | GAGA | ACGT | AGTA | CGAG | GACA | ACGA | CGGT | GGGT | TGTG |
| DRB1-1336 | CTGA | GAGA | ACGT | AGTA | CGAG | GACA | ACGA | CGGT | GGGT | TGGT |
| DRB1-1424 | CTGA | GAGA | ACGT | AGTA | CGAG | GACA | AGGC | CGGT | GGGT | TGGT |
| DRB1-030201 | CTGA | GAGA | ACGT | AGTA | CGAG | GACC | AGAA | GGGT | GGGT | TGGT |
| DRB1-030202 | CTGA | GAGA | ACGT | AGTA | CGAG | GACC | AGAA | GGGT | GGGT | TGGT |
| DRB1-0303 | CTGA | GAGA | ACGT | AGTA | CGAG | GACC | AGAA | GGGT | GGGT | TGTG |
| DRB1-0306 | CTGA | GAGA | ACGT | AGTA | CGAG | GACC | AGAA | GGGT | GGGT | TGTG |
| DRB1-1419 | CTGA | GAGA | ACGT | AGTA | CGAG | GACC | AGAA | CGGT | GGGT | TGGT |
| DRB1-1429 | CTGA | GAGA | ACGT | AGTA | CGAG | GACC | AGAG | CGGT | GGGT | TGTG |
| DRB1-1406 | CTGA | GAGA | ACGT | AGTA | CGAG | GACC | AGAG | CGGT | GGGT | TGTG |
| DRB1-1402 | CTGA | GAGA | ACGT | AGTA | CGAG | GACC | AGAG | CGGT | GGGT | TGGT |
| DRB1-1409 | CTGA | GAGA | ACGT | AGTA | CGAG | GACC | AGAG | CGGT | GGGT | TGGT |
| DRB1-1413 | CTGA | GAGA | ACGT | AGTA | CGAG | GACC | AGAG | CGGT | GGGT | TGGT |
| DRB1-1446 | CTGA | GAGA | ACGT | AGTA | CGAG | GACC | AGAG | CGGT | GGGT | TGGT |
| DRB1-1447 | CTGA | GAGA | ACGT | AGTA | CGAG | GACC | AGAG | CGGT | GGGT | TGGT |
| DRB1-1448 | CTGA | GAGA | ACGT | AGTA | CGAG | GACC | AGAG | CGGT | GGGT | TGGT |
| DRB1-1403 | CTGA | GAGA | ACGT | AGTA | CGAG | GACC | ACAG | TGGT | GGGT | TGGT |
| DRB1-140302 | CTGA | GAGA | ACGT | AGTA | CGAG | GACC | ACAG | TGGT | GGGT | TGGT |
| DRB1-1412 | CTGA | GAGA | ACGT | AGTA | CGAG | GACC | ACAG | TGGT | GGGT | TGTG |
| DRB1-1418 | CTGA | GAGA | ACGT | AGTA | TGAG | GACC | GGAG | AGGT | GGGT | TGTG |
| DRB1-1326 | CTGA | GAGA | ACGT | AGTA | TGAG | GACT | ACAG | CGGT | GGGT | TGGT |
| DRB1-1427 | CTGA | GAGA | ACGT | AGTA | CGAG | GACT | ACAG | TGGT | GGGT | TGGT |
| DRB1-1334 | CTGA | GAGA | ACCT | AGTT | CGAG | GACA | ACGA | CGGT | GGGT | TGGT |
| DRB1-0319 | CTGA | GAGA | ACGT | AGTT | CGAG | GACA | AGAA | GGGT | GGGT | TGGT |
| DRB1-1310 | CTGA | GAGA | ACGT | AGTT | CGAG | GACA | ACAA | CGGT | GGGT | TGTG |
| DRB1-130101 | CTGA | GAGA | ACGT | AGTT | CGAG | GACA | ACGA | CGGT | GGGT | TGTG |
| DRB1-130102 | CTGA | GAGA | ACGT | AGTT | CGAG | GACA | ACGA | CGGT | GGGT | TGTG |
| DRB1-130103 | CTGA | GAGA | ACGT | AGTT | CGAG | GACA | ACGA | CGGT | GGGT | TGTG |
| DRB1-1315 | CTGA | GAGA | ACGT | AGTT | CGAG | GACA | ACGA | CGGT | GGGT | TGTG |
| DRB1-1327 | CTGA | GAGA | ACGT | AGTT | CGAG | GACA | ACGA | CGGT | GGGT | TGTG |
| DRB1-1328 | CTGA | GAGA | ACGT | AGTT | CGAG | GACA | ACGA | CGGT | GGGT | TGTG |
| DRB1-1335 | CTGA | GAGA | ACGT | AGTT | CGAG | GACA | ACGA | CGGT | GGGT | TGTG |
| DRB1-1351 | CTGA | GAGA | ACGT | AGTT | CGAG | GACA | ACGA | CGGT | GGGT | TGTG |
| DRB1-1359 | CTGA | GAGA | ACGT | AGTT | CGAG | GACA | ACGA | CGGT | GGGT | TGTG |
| DRB1-1361 | CTGA | GAGA | ACGT | AGTT | CGAG | GACA | ACGA | CGGT | GGGT | TGTG |

TABLE XII-continued

| Position cDNA | 1111<br>2222<br>5678 | 1111<br>9999<br>3456 | 1112<br>9990<br>7890 | 2222<br>2222<br>4567 | 2222<br>6666<br>1234 | 2222<br>8888<br>3456 | 2222<br>9999<br>6789 | 3333<br>0011<br>8901 | 3333<br>3344<br>3901 | 3333<br>4444<br>2345 |
|---|---|---|---|---|---|---|---|---|---|---|
| DRB1-1316 | CTGA | GAGA | ACGT | AGTT | CGAG | GACA | ACGA | CGGT | GGGT | TGAT |
| DRB1-130201 | CTGA | GAGA | ACGT | AGTT | CGAG | GACA | ACGA | CGGT | GGGT | TGGT |
| DRB1-130202 | CTGA | GAGA | ACGT | AGTT | CGAG | GACA | ACGA | CGGT | GGGT | TGGT |
| DRB1-1331 | CTGA | GAGA | ACGT | AGTT | CGAG | GACA | ACGA | CGGT | GGGT | TGGT |
| DRB1-1339 | CTGA | GAGA | ACGT | AGTT | CGAG | GACA | ACGA | CGGT | GGGT | TGGT |
| DRB1-1341 | CTGA | GAGA | ACGT | AGTT | CGAG | GACA | ACGA | CGGT | GGGT | TGGT |
| DRB1-1309 | CTGA | GAGA | ACGT | AGTT | CGAG | GACA | AGGC | CGGT | GGGT | TGTG |
| DRB1-1306 | CTGA | GAGA | ACGT | AGTT | CGAG | GACA | ACAG | CGGT | GGGT | TGTG |
| DRB1-1356 | CTGA | GAGA | ACGT | AGTT | CGAG | GACC | ACAG | CGGT | GGGT | TGGT |
| DRB1-0311 | CTGA | GAGA | ACGT | AGTT | CGAG | GACC | AGAA | AGGT | GGGT | TGTG |
| DRB1-0324 | CTGA | GAGA | ACGT | AGTT | CGAG | GACC | AGAA | AGGT | GGGT | TGTG |
| DRB1-0320 | CTGA | GAGA | ACGT | AGTT | CGAG | GACC | AGAA | GGGT | GGGC | TGTG |
| DRB1-030101 | CTGA | GAGA | ACGT | AGTT | CGAG | GACC | AGAA | GGGT | GGGT | TGTG |
| DRB1-030102 | CTGA | GAGA | ACGT | AGTT | CGAG | GACC | AGAA | GGGT | GGGT | TGTG |
| DRB1-0307 | CTGA | GAGA | ACGT | AGTT | CGAG | GACC | AGAA | GGGT | GGGT | TGTG |
| DRB1-0312 | CTGA | GAGA | ACGT | AGTT | CGAG | GACC | AGAA | GGGT | GGGT | TGTG |
| DRB1-0313 | CTGA | GAGA | ACGT | AGTT | CGAG | GACC | AGAA | GGGT | GGGT | TGTG |
| DRB1-0315 | CTGA | GAGA | ACGT | AGTT | CGAG | GACC | AGAA | GGGT | GGGT | TGTG |
| DRB1-0316 | CTGA | GAGA | ACGT | AGTT | CGAG | GACC | AGAA | GGGT | GGGT | TGTG |
| DRB1-0318 | CTGA | GAGA | ACGT | AGTT | CGAG | GACC | AGAA | GGGT | GGGT | TGTG |
| DRB1-0322 | CTGA | GAGA | ACGT | AGTT | CGAG | GACC | AGAA | GGGT | GGGT | TGTG |
| DRB1-0323 | CTGA | GAGA | ACGT | AGTT | CGAG | GACC | AGAA | GGGT | GGGT | TGTG |
| DRB1-030501 | CTGA | GAGA | ACGT | AGTT | CGAG | GACC | AGAA | GGGT | GGGT | TGGT |
| DRB1-030502 | CTGA | GAGA | ACGT | AGTT | CGAG | GACC | AGAA | GGGT | GGGT | TGGT |
| DRB1-0309 | CTGA | GAGA | ACGT | AGTT | CGAG | GACC | AGAA | GGGT | GGGT | TGGT |
| DRB1-0314 | CTGA | GAGA | ACGT | AGTT | CGAG | GACC | AGAA | GGGT | GGGT | TGGT |
| DRB1-1421 | CTGA | GAGA | ACGT | AGTT | CGAG | GACC | AGAA | CGGT | GGGT | TGTG |
| DRB1-1417 | CTGA | GAGA | ACGT | AGTT | CGAG | GACC | AGAA | CGGT | GGGT | TGTG |
| DRB1-1430 | CTGA | GAGA | ACGT | AGTT | CGAG | GACC | AGAA | CGGT | GGGT | TGGT |
| DRB1-1433 | CTGA | GAGA | ACGT | AGTT | CGAG | GACC | AGAA | AGGT | GGGT | TGTG |
| DRB1-1320 | CTGA | GAGA | ACGT | AGTT | CGAG | GACC | ACGA | CGGT | GGGT | TGTG |
| DRB1-1329 | CTGA | GAGA | ACGT | AGTT | CGAG | GACC |  |  | GGGT | TGGT |
| DRB1-1342 | CTGA | GAGA | ACGT | AGTT | CGAG | GACT |  |  | GGGT | TGTG |
| DRB1-1305 | CTGA | GAGA | ACGT | AGTT | CGAG | GACT |  |  | GGGT | TGGT |
| DRB1-1350 | CTGA | GAGA | ACGT | AGTT | CGAG | GACT |  |  | GGGT | TGGT |
| DRB1-1318 | CTGA | GAGA | ACGT | AGTT | CGAG | GACT |  |  | GGGT | TGTG |
| DRB1-1116 | CTGA | GAGA | ACGT | AGTT | GGAG | GACA |  |  | GGGT | TGTG |
| DRB1-1120 | CTGA | GAGA | ACGT | AGTT | GGAG | GACA |  |  | GGGT | TGGT |
| DRB1-0308 | CTGA | GAGA | ACGT | AGTT | GGAG | GACC |  |  | GGGT | TGTG |
| DRB1-0310 | CTGA | GAGA | ACGT | AGTT | GGAG | GACC |  |  | GGGT | TGTG |
| DRB1-1343 | CTGA | GAGA | ACGT | AGTT | GGAG | GACC |  |  | GGGT | TGTG |
| DRB1-1109 | CTGA | GAGA | ACGT | AGTT | GGAG | GACT |  |  | GGGT | TGGT |
| DRB1-1128 | CTGA | GAGA | ACGT | AGTT | GGAG | GACT |  |  | GGGT | TGGT |
| DRB1-1140 | CTGA | GAGA | ACGT | AGTT | GGAG | GACT |  |  | GGGT | TGTG |
| DRB1-1115 | CTGA | GAGG | ACTT | AGTT | GGAG | GACT | ACAG | CGGT | GGGT | TGGT |
| DRB1-1124 | CTGA | GAGG | ACGT | AGTT | GGAG | GACT | ACAG | CGGT | GGGT | TGGT |
| DRB1-1362 | CTGA | GAGG | ACTT | AGTT | GGAG | GACT | ACAG | CGGT | GGGT | TGGT |
| DRB1-1144 | CTGA | GAGT | ACGC | AGTT | GGAG | GACT | ACAG | CGGT | GGGT | TGTG |

TABLE XII-continued

| Position cDNA | 1111<br>2222<br>5678 | 1111<br>9999<br>3456 | 1112<br>9990<br>7890 | 2222<br>2222<br>4567 | 2222<br>6666<br>1234 | 2222<br>8888<br>3456 | 2222<br>9999<br>6789 | 3333<br>0011<br>8901 | 3333<br>3344<br>8901 | 3333<br>4444<br>2345 |
|---|---|---|---|---|---|---|---|---|---|---|
| DRB1-130301 | CTGA | GAGT | ACGT | AGTA | CGAG | GACA | ACAA | CGGT | GGGT | TGGT |
| DRB1-130302 | CTGA | GAGT | ACGT | AGTA | CGAG | GACA | ACAA | CGGT | GGGT | TGGT |
| DRB1-1333 | CTGA | GAGT | ACGT | AGTA | CGAG | GACA | ACAA | CGGT | GGGT | TGGT |
| DRB1-1337 | CTGA | GAGT | ACGT | AGTA | CGAG | GACA | ACAA | CGGT | GGGT | TGGT |
| DRB1-1338 | CTGA | GAGT | ACGT | AGTA | CGAG | GACA | ACGA | CGGT | GGGT | TGGT |
| DRB1-1312 | CTGA | GAGT | ACGT | AGTA | CGAG | GACA | ACAG | CGGT | GGGT | TGGT |
| DRB1-1313 | CTGA | GAGT | ACGT | AGTA | CGAG | GACA | ACAG | CGGT | GGGT | TGGT |
| DRB1-1348 | CTGA | GAGT | ACGT | AGTA | CGAG | GACA | ACGA | CGGT | GGGT | TGTG |
| DRB1-1358 | CTGA | GAGT | ACGT | AGTA | CGAG | GACA | ACAG | CGGT | GGGC | TGTG |
| DRB1-0317 | CTGA | GAGT | ACGT | AGTA | CGAG | GACC | AGAA | AGGT | GGGT | TGGT |
| DRB1-0434 | CTGA | GAGT | ACGT | AGTA | CGAG | GACC | AGAA | CGGT | GGGT | TGGT |
| DRB1-0820 | CTGA | GAGT | ACGT | AGTA | CGAG | GACT | ACAG | TGGT | GGGT | TGTG |
| DRB1-130701 | CTGA | GAGT | ACGT | AGTA | CGAG | GACT | ACAG | CGGT | GGGT | TGGT |
| DRB1-1349 | CTGA | GAGT | ACGT | AGTA | CGAG | GACT | ACAG | CGGT | GGGT | TGGT |
| DRB1-1347 | CTGA | GAGT | ACGT | AGTA | CGAG | GACT | ACAG | TGGT | GGGT | TGGT |
| DRB1-1355 | CTGA | GAGT | ACGT | AGTA | CGAG | GACT | ACAG | TGGT | GGGT | TGGT |
| DRB1-1141 | CTGA | GAGT | ACGT | AGTA | GGAG | GACT | ACGA | CGGT | GGGT | TGTG |
| DRB1-1137 | CTGA | GAGT | ACGT | AGTA | GGAG | GACT | ACAG | CGGT | GGGT | TGGT |
| DRB1-1425 | CTGA | GAGT | ACGT | AGTA | GGAG | GACT | ACAG | CGGT | GGGT | TGGT |
| DRB1-130702 | CTGA | GAGT | ACGT | AGTA | TGAG | GACT | ACAG | CGGT | GGGT | TGGT |
| DRB1-1442 | CTGA | GAGT | ACGT | AGTT | CGAG | GACC | GGAG | AGGT | GGGT | TGGT |
| DRB1-1304 | CTGA | GAGT | ACGT | AGTT | CGAG | GACA | ACGA | CGGT | GGGT | TGTG |
| DRB1-1322 | CTGA | GAGT | ACGT | AGTT | CGAG | GACA | ACGA | CGGT | GGGT | TGTG |
| DRB1-1352 | CTGA | GAGT | ACGT | AGTT | CGAG | GACA | ACGA | CGGT | GGGT | TGTG |
| DRB1-1323 | CTGA | GAGT | ACGT | AGTT | CGAG | GACA | ACGA | CGGT | GGGT | TGGT |
| DRB1-1324 | CTGA | GAGT | ACGT | AGTT | CGAG | GACT | ACGA | CGGT | GGGT | TGTG |
| DRB1-1354 | CTGA | GAGT | ACGT | AGTT | CGAG | GACT | ACGA | CGGT | GGGT | TGTG |
| DRB1-1311 | CTGA | GAGT | ACGT | AGTT | CGAG | GACT | ACAG | CGGT | GGGT | TGTG |
| DRB1-1330 | CTGA | GAGT | ACGT | AGTT | CGAG | GACA | ACAG | CGGT | GGGT | TGGT |
| DRB1-1325 | CTGA | GAGT | ACGT | AGTT | CGAG | GACC | ACAG | CGGT | GGGT | TGGT |
| DRB1-131401 | CTGA | GAGT | ACGT | AGTT | CGAG | GACT | ACAG | CGGT | GGGT | TGGT |
| DRB1-1321 | CTGA | GAGT | ACGT | AGTT | CGAG | GACT | ACAG | CGGT | GGGT | TGGT |
| DRB1-1346 | CTGA | GAGT | ACGT | AGTT | CGAG | GACT | ACAG | CGGT | GGGT | TGGT |
| DRB1-1344 | CTGA | GAGT | ACGT | AGTT | CGAG | GACC | AGAG | CGGT | GGGT | TGTG |
| DRB1-0325 | CTGA | GAGT | ACGT | AGTT | CGAG | GACC | AGAA | GGGT | GGGT | TGTG |
| DRB1-1102 | CTGA | GAGT | ACGT | AGTT | GGAG | GACA | ACGA | CGGT | GGGT | TGTG |
| DRB1-1121 | CTGA | GAGT | ACGT | AGTT | GGAG | GACA | ACGA | CGGT | GGGC | TGTG |
| DRB1-1118 | CTGA | GAGT | ACGT | AGTT | GGAG | GACA | ACAG | CGGT | GGGT | TGTG |
| DRB1-1114 | CTGA | GAGT | ACGT | AGTT | GGAG | GACA | ACGA | CGGT | GGGT | TGGT |
| DRB1-1345 | CTGA | GAGT | ACGT | AGTT | GGAG | GACA | ACGA | CGGT | GGGT | TGGT |
| DRB1-1119 | CTGA | GAGT | ACGT | AGTT | GGAG | GACA | ACAG | CGGT | GGGT | TGGT |
| DRB1-1131 | CTGA | GAGT | ACGT | AGTT | GGAG | GACA | ACAG | CGGT | GGGT | TGGT |
| DRB1-1145 | CTGA | GAGT | ACGT | AGTT | GGAG | GACA | ACAG | TGGT | GGGT | TGGT |
| DRB1-1136 | CTGA | GAGT | ACGT | AGTT | GGAG | GACC | ACGA | CGGT | GGGT | TGTG |
| DRB1-1107 | CTGA | GAGT | ACGT | AGTT | GGAG | GACC | AGAA | GGGT | GGGT | TGTG |

TABLE XII-continued

| Position cDNA | 1111<br>2222<br>5678 | 1111<br>9999<br>3456 | 1112<br>9990<br>7890 | 2222<br>2222<br>4567 | 2222<br>6666<br>1234 | 2222<br>8888<br>3456 | 2222<br>9999<br>6789 | 3333<br>0011<br>8901 | 3333<br>3344<br>3901 | 3333<br>4444<br>2345 |
|---|---|---|---|---|---|---|---|---|---|---|
| DRB1-1142 | CTGA | GAGT | ACGT | AGTT | GGAG | GACC | ACAG | CGGT | GGGT | TGTG |
| DRB1-1134 | CTGA | GAGT | ACGT | AGTT | GGAG | GACC | AGAG | CGGT | GGGT | TGTG |
| DRB1-110801 | CTGA | GAGT | ACGT | AGTT | GGAG | GACC | ACAG | CGGT | GGGT | TGGT |
| DRB1-110802 | CTGA | GAGT | ACGT | AGTT | GGAG | GACC | ACAG | CGGT | GGGT | TGGT |
| DRB1-1126 | CTGA | GAGT | ACGT | AGTT | GGAG | GACC | AGAG | CGGT | GGGT | TGGT |
| DRB1-1103 | CTGA | GAGT | AGGT | AGTT | GGAG | GACT | ACGA | CGGT | GGGT | TGTG |
| DRB1-110601 | CTGA | GAGT | ACGT | AGTT | GGAG | GACT | ACAG | CGGT | GGGT | TGTG |
| DRB1-110602 | CTGA | GAGT | ACGT | AGTT | GGAG | GACT | ACAG | CGGT | GGGT | TGTG |
| DRB1-1135 | CTGA | GAGT | ACGT | AGTT | GGAC | GACT | ACAG | CGGT | GGGT | TGTG |
| DRB1-110401 | CTGA | GAGT | ACGT | AGTT | GGAG | GACT | ACAG | CGGT | GGGT | TGTG |
| DRB1-110402 | CTGA | GAGT | ACGT | AGTT | GGAG | GACT | ACAG | CGGT | GGGT | TGTG |
| DRB1-1143 | CTGA | GAGT | ACGT | AGTT | GGAG | GACT | ACAG | CGGT | GGGT | TGTG |
| DRB1-1146 | CTGA | GAGT | ACGT | AGTT | GGAG | GACT | ACAG | CGGT | GGGT | TGTG |
| DRB1-1138 | CTGA | GAGT | ACGT | AGTT | GGGG | GACT | ACAG | CGGT | GGGT | TGTG |
| DRB1-1125 | CTGA | GAGT | ACGT | AGTT | GGAG | GACT | ACAG | TGGT | GGGT | TGTG |
| DRB1-1111 | CTGA | GAGT | ACGT | AGTT | GGAG | GACT | ACGA | CGGT | GGGT | TGGT |
| DRB1-1133 | CTGA | GAGT | ACGT | AGTT | GGAC | GACT | ACAG | CGGT | GGGT | TGGT |
| DRB1-110101 | CTGA | GAGT | ACGT | AGTT | GGAG | GACT | ACAG | CGGT | GGGT | TGGT |
| DRB1-110102 | CTGA | GAGT | ACGT | AGTT | GGAG | GACT | ACAG | CGGT | GGGT | TGGT |
| DRB1-110103 | CTGA | GAGT | ACGT | AGTT | GGAG | GACT | ACAG | CGGT | GGGT | TGGT |
| DRB1-110104 | CTGA | GAGT | ACGT | AGTT | GGAG | GACT | ACAG | CGGT | GGGT | TGGT |
| DRB1-110105 | CTGA | GAGT | ACGT | AGTT | GGAG | GACT | ACAG | CGGT | GGGT | TGGT |
| DRB1-112701 | CTGA | GAGT | ACGT | AGTT | GGAG | GACT | ACAG | CGGT | GGGT | TGGT |
| DRB1-112702 | CTGA | GAGT | ACGT | AGTT | GGAG | GACT | ACAG | CGGT | GGGT | TGGT |
| DRB1-1130 | CTGA | GAGT | ACGT | AGTT | GGAG | GACT | ACAG | CGGT | GGGT | TGGT |
| DRB1-1139 | CTGA | GAGT | ACGT | AGTT | GGAG | GACT | ACAG | CGGT | GGGT | TGGT |
| DRB1-1123 | CTGA | GAGT | ACGT | AGTT | GGAG | GACT | ACAG | TGGT | GGGT | TGGT |
| DRB1-1132 | CTGA | GAGT | ACGT | AGTT | GGAG | GACT | ACAG | TGGT | GGGT | TGGT |
| DRB1-131402 | CTGA | GAGT | ACGT | AGTT | TGAG | GACT | ACAG | CGGT | GGGT | TGGT |
| DRB1-0304 | CTGA | GAGT | CCGT | AGTT | CGAG | GACC | AGAA | GGGT | GGGT | TGTG |
| DRB1-1129 | CTGA | GAGT | CCGT | AGTT | GGAG | GACT | ACAG | CGGT | GGGT | TGGT |
| DRB1-1147 | CTGA | GAGT | CCGT | AGTT | GGAG | GACT | ACAG | CGGT | GGGC | TGTG |
| DRB1-1360 | CTGA | GAGT | CCGT | AGTA | TGAG | GACC | ACAG | CGGT | GGGT | TGGT |
| DRB1-1441 | CTGA | GAGT | TCCT | AGTA | CGAG | GACC | AGAG | CGGT | GGGT | TGGT |
| DRB1-1308 | CTGA | GAGT | TCGT | AGTA | CGAG | GACA | ACGA | CGGT | GGGT | TGTG |
| DRB1-1319 | CTGA | GAGT | TCGT | AGTA | CGAG | GACA | ACGA | CGGT | GGGT | TGTG |
| DRB1-140502 | CTGA | GAGT | TCGT | AGTA | CGAG | GACC | GGAG | AGGT | GGGT | TGTG |
| DRB1-1423 | CTGA | GAGT | TCGT | AGTA | CGAG | GACC | GGAG | AGGT | GGGT | TGTG |
| DRB1-1420 | CTGA | GAGT | TCGT | AGTA | CGAG | GACC | AGAG | CGGT | GGGT | TGTG |
| DRB1-1357 | CTGA | GAGT | TCGT | AGTT | CGAG | GACA | ACGA | CGGT | GGGT | TGTG |
| DRB1-0321 | CTGA | GAGT | TCGT | AGTT | CGAG | GACC | AGAA | GGGT | GGGT | TGTG |
| DRB1-1416 | CTGA | GAGT | TCGT | AGTA | GGAG | GACA | ACGA | CGGT | GGGT | TGTG |
| DRB1-1117 | CTGA | GAGT | TCGT | AGTA | GGAG | GACC | GGAG | AGGT | GGGT | TGTG |
| DRB1-140101 | CTGA | GAGT | TCGT | AGTA | GGAG | GACC | GGAG | AGGT | GGGT | TGTG |
| DRB1-140102 | CTGA | GAGT | TCGT | AGTA | GGAG | GACC | GGAG | AGGT | GGGT | TGTG |
| DRB1-1408 | CTGA | GAGT | TCGT | AGTA | GGAG | GACC | GGAG | AGGT | GGGT | TGTG |
| DRB1-1426 | CTGA | GAGT | TCGT | AGTA | GGAG | GACC | GGAG | AGGT | GGGT | TGTG |
| DRB1-1438 | CTGA | GAGT | TCGT | AGTA | GGAG | GACC | GGAG | AGGT | GGGT | TGTG |
| DRB1-1439 | CTGA | GAGT | TCGT | AGTA | GGAG | GACC | GGAG | AGGT | GGGT | TGTG |

TABLE XII-continued

| Position cDNA | 1111<br>2222<br>5678 | 1111<br>9999<br>3456 | 1112<br>9990<br>7890 | 2222<br>2222<br>4567 | 2222<br>6666<br>1234 | 2222<br>8888<br>3456 | 2222<br>9999<br>6789 | 3333<br>0011<br>8901 | 3333<br>3344<br>8901 | 3333<br>4444<br>2345 |
|---|---|---|---|---|---|---|---|---|---|---|
| DRB1-1432 | CTGA | GAGT | TCGT | AGTA | GGAG | GACC | GGAG | CGGT | GGGT | TGTG |
| DRB1-1434 | CTGA | GAGT | TCGT | AGTA | GGAG | GACC | GGAG | CGGT | GGGT | TGTG |
| DRB1-1113 | CTGA | GAGT | TCGT | AGTT | GGAG | GACC | GGAG | CGGT | GGGT | TGTG |
| DRB1-1435 | CTGA | GAGT | TCGT | AGTT | GGAG | GACC | GGAG | AGGT | GGGT | TGTG |
| DRB1-1437 | CTGA | GAGT | TCGT | AGTA | TGAG | GACA | AGGC | CGGT | GGGT | TGTG |
| DRB1-1445 | CTGA | GAGT | TCGT | AGTA | TGAG | GACA | GGAG | AGGT | GGGT | TGTG |
| DRB1-140501 | CTGA | GAGT | TCGT | AGTA | TGAG | GACC | GGAG | AGGT | GGGT | TGTG |
| DRB1-1443 | CTGA | GAGT | TCGT | AGTA | TGAG | GACC | GGAG | AGGT | GGGT | TGTG |
| DRB1-1110 | CTGA | GAGT | TCGT | AGTT | GGAG | GACT | ACAG | CGGT | GGGT | TGGT |
| DRB1-111201 | CTGA | GAGT | TCGT | AGTT | GGAG | GACT | ACAG | CGGT | GGGT | TGGT |
| DRB1-111202 | CTGA | GAGT | TCGT | AGTT | GGAG | GACT | ACAG | CGGT | GGGT | TGGT |
| DRB1-1414 | CTGA | GAGT | TCGT | AGTA | CGAG | GACC | GGAG | AGGT | GGGT | TGGT |
| DRB1-1436 | CTGA | GAGT | TCGT | AGTA | CGAG | GACC | GGAG | AGGT | GGGT | TGGT |
| DRB1-140701 | CTGA | GAGT | TCGT | AGTA | GGAG | GACC | GGAG | AGGT | GGGT | TGGT |
| DRB1-140702 | CTGA | GAGT | TCGT | AGTA | GGAG | GACC | GGAG | AGGT | GGGT | TGGT |
| DRB1-1422 | CTGA | GAGT | TCGT | AGTA | GGAG | GACT | ACAG | CGGT | GGGT | TGGT |
| DRB1-1440 | CTGA | GAGT | TCGT | AGTA | CGAG | GACC | ACAG | TGGT | GGGT | TGGT |
| DRB1-1444 | CTGA | GAGT | TCGT | AGTA | TGAG | GACC | GGAG | AGGT | GGGT | TGGT |
| DRB1-120101 | GTGA | GAGC | TCCT | AGTT | CGAG | GACA | ACAG | CGGT | GGGC | TGTG |
| DRB1-120102 | GTGA | GAGC | TCCT | AGTT | CGAG | GACA | ACAG | CGGT | GGGC | TGTG |
| DRB1-1206 | GTGA | GAGC | TCCT | AGTT | CGAG | GACA | ACAG | CGGT | GGGC | TGTG |
| DRB1-1207 | GTGA | GAGC | TCCT | AGTT | CGAG | GACA | ACAG | CGGT | GGGC | TGTG |
| DRB1-1208 | GTGA | GAGC | TCCT | AGTT | CGAG | GACA | ACAG | CGGT | GGGC | TGTG |
| DRB1-1209 | GTGA | GAGC | TCCT | AGTT | CGAG | GACA | ACAG | CGGT | GGGC | TGTG |
| DRB1-120302 | GTGA | GAGC | TCCT | AGTT | CGAG | GACA | ACAG | CGGT | GGGT | TGTG |
| DRB1-1204 | GTGA | GAGC | TCCT | AGTT | GGAG | GACA | ACAG | CGGT | GGGC | TGTG |
| DRB1-120201 | GTGA | GAGC | TCCT | AGTT | CGAG | GACT | ACAG | CGGT | GGGC | TGTG |
| DRB1-120202 | GTGA | GAGC | TCCT | AGTT | CGAG | GACT | ACAG | CGGT | GGGC | TGTG |
| DRB1-0816 | GTGA | GAGG | ACGT | AGTA | CGAG | GACT | ACAG | TGGT | GGGT | TGGT |
| DRB1-0818 | GTGA | GAGT | ACGT | AGTA | CGAG | GACA | ACAG | CGGT | GGGT | TGGT |
| DRB1-0825 | GTGA | GAGT | ACGT | AGTA | CGAG | GACA | ACAG | CGGT | GGGT | TGGT |
| DRB1-0810 | GTGA | GAGT | ACGT | AGTA | CGAG | GACA | ACAG | TGGT | GGGT | TGTG |
| DRB1-0812 | GTGA | GAGT | ACGT | AGTA | CGAG | GACA | ACAG | TGGT | GGGC | TGTG |
| DRB1-080302 | GTGA | GAGT | ACGT | AGTA | CGAG | GACA | ACAG | TGGT | GGGT | TGGT |
| DRB1-0814 | GTGA | GAGT | ACGT | AGTA | CGAG | GACA | ACAG | TGGT | GGGT | TGGT |
| DRB1-0819 | GTGA | GAGT | ACGT | AGTA | CGAG | GACA | ACAG | TGGT | GGGT | TGGT |
| DRB1-0823 | GTGA | GAGT | ACGT | AGTA | CGAG | GACA | ACAG | TGGT | GGGT | TGGT |
| DRB1-0813 | GTGA | GAGT | ACGT | AGTA | CGAG | GACC | ACAG | TGGT | GGGT | TGGT |
| DRB1-080401 | GTGA | GAGT | ACGT | AGTA | CGAG | GACT | ACAG | TGGT | GGGT | TGTG |
| DRB1-080404 | GTGA | GAGT | ACGT | AGTA | CGAG | GACT | ACAG | TGGT | GGGT | TGTG |
| DRB1-0806 | GTGA | GAGT | ACGT | ALTA | CGAG | GACT | ACAG | TGGT | GGGT | TGTG |
| DRB1-0822 | GTGA | GAGT | ACGT | AGTA | CGAG | GACT | ACAG | TGGT | GGGC | TGTG |
| DRB1-0805 | GTGA | GAGT | ACGT | AGTA | CGAG | GACT | ACAG | CGGT | GGGT | TGGT |
| DRB1-0824 | GTGA | GAGT | ACGT | AGTA | CGAG | GACT | ACAG | CGGT | GGGT | TGGT |
| DRB1-080101 | GTGA | GAGT | ACGT | AGTA | CGAG | GACT | ACAG | TGGT | GGGT | TGGT |
| DRB1-080102 | GTGA | GAGT | ACGT | AGTA | CGAG | GACT | ACAG | TGGT | GGGT | TGGT |
| DRB1-080201 | GTGA | GAGT | ACGT | AGTA | CGAG | GACT | ACAG | TGGT | GGGT | TGGT |
| DRB1-080202 | GTGA | GAGT | ACGT | AGTA | CGAG | GACT | ACAG | TGGT | GGGT | TGGT |
| DRB1-080203 | GTGA | GAGT | ACGT | AGTA | CGAG | GACT | ACAG | TGGT | GGGT | TGGT |
| DRB1-0807 | GTGA | GAGT | ACGT | AGTA | CGAG | GACT | ACAG | TGGT | GGGT | TGGT |

TABLE XII-continued

| Position cDNA | 1111 2222 5678 | 1111 9999 3456 | 1112 9990 7890 | 2222 2222 4567 | 2222 6666 1234 | 2222 8888 3456 | 2222 9999 6789 | 3333 0011 8901 | 3333 3344 3901 | 3333 4444 2345 |
|---|---|---|---|---|---|---|---|---|---|---|
| DRB1-0811 | GTGA | GAGT | ACGT | AGTA | CGAG | GACT | ACAG | TGGT | GGGT | TGGT |
| DRB1-080402 | GTGA | GAGT | ACGT | AGTA | CGAG | GACT | ACAG | TGGT | GGGT | TGTT |
| DRB1-080403 | GTGA | GAGT | ACGT | AGTA | CGAG | GACT | ACAG | TGGT | GGGT | TGTT |
| DRB1-0808 | GTGA | GAGT | ACGT | AGTA | GGAG | GACT | ACAG | TGGT | GGGT | TGGT |
| DRB1-0815 | GTGA | GAGT | ACGT | AGTA | GGAG | GACA | ACAG | TGGT | GGGT | TGGT |
| DRB1-0817 | GTGA | GAGT | ACGT | AGTT | CGAG | GACT | ACAG | TGGT | GGGT | TGGT |
| DRB1-1317 | GTGA | GAGT | ACGT | AGTT | CGAG | GACA | ACGA | CGGT | GGGT | TGTG |
| DRB1-1105 | GTGA | GAGT | ACGT | AGTT | GGAG | GACT | ACAG | CGGT | GGGT | TGGT |
| DRB1-0809 | GTGA | GAGT | TCGT | AGTA | CGAG | GACT | ACAG | TGGT | GGGT | TGGT |
| DRB1-0821 | GTGA | GAGT | TCGT | AGTA | CGAG | GACT | ACAG | TGGT | GGGT | TGGT |
| DRB1-1415 | GTGA | GAGT | TCGT | AGTA | CGAG | GACT | ACAG | TGGT | GGGT | TGTG |
| DRB1-1205 | GTGA | GAGT | TCCT | AGTT | CGAG | GACA | ACAG | CGGT | GGGC | TGTG |
| DRB1-1404 | GTGA | GAGT | TCGT | AGTA | GGAG | GACC | GGAG | AGGT | GGGT | TGTG |
| DRB1-1411 | GTGA | GAGT | TCGT | AGTA | GGAG | GACC | GGAG | AGGT | GGGT | TGTG |
| DRB1-1428 | GTGA | GAGT | TCGT | AGTA | GGAG | GACC | GGAG | AGGT | GGGC | TGTG |
| DRB1-1431 | GTGA | GAGT | TCGT | AGTA | GGAG | GACC | GGAG | CGGT | GGGT | TGTG |
| DRB1-1507 | GGGA | GAGT | CCGT | AGTA | TGAG | GACA | AGGC | CGGT | GGGT | TGTG |
| DRB1-1511 | GGGA | GAGT | CCGT | AGTA | TGAG | GACA | AGGC | CGGT | GGGT | TGGT |
| DRB1-1605 | GGGA | GAGT | CCGT | AGTA | TGAG | GACA | ACAG | CGGT | GGGT | TGGT |
| DRB1-1607 | GGGA | GAGT | CCGT | AGTA | TGAG | GACA | ACAG | CGGT | GGGT | TGGT |
| DRB1-160201 | GGGA | GAGT | CCGT | AGTA | TGAG | GACC | ACAG | CGGT | GGGT | TGGT |
| DRB1-160202 | GGGA | GAGT | CCGT | AGTA | TGAG | GACC | ACAG | CGGT | GGGT | TGGT |
| DRB1-160101 | GGGA | GAGT | CCGT | AGTA | TGAG | GACT | ACAG | CGGT | GGGT | TGGT |
| DRB1-160102 | GGGA | GAGT | CCGT | AGTA | TGAG | GACT | ACAG | CGGT | GGGT | TGGT |
| DRB1-1603 | GGGA | GAGT | CCGT | AGTA | TGAG | GACT | ACAG | CGGT | GGGT | TGGT |
| DRB1-1604 | GGGA | GAGT | CCGT | AGTA | TGAG | GACT | ACAG | TGGT | GGGT | TGGT |
| DRB1-150104 | GGGA | GAGT | CCGT | AGTT | CGAG | GACA | AGGC | CGGT | GGGT | TGTG |
| DRB1-1512 | GGGA | GAGT | CCGT | AGTT | CGAG | GACA | AGGC | CGGT | GGGT | TGTG |
| DRB1-150202 | GGGA | GAGT | CCGT | AGTT | CGAG | GACA | AGGC | CGGT | GGGT | TGGT |
| DRB1-1510 | GGGA | GAGT | CCGT | AGTT | TGAG | GACA | ACGA | CGGT | GGGT | TGTG |
| DRB1-1508 | GGGA | GAGT | CCGT | AGTT | TGAG | AACA | AGGC | CGGT | GGGT | TGGT |
| DRB1-150102 | GGGA | GAGT | CCGT | AGTT | TGAG | GACA | AGGC | CGGT | GAGT | TGTG |
| DRB1-150101 | GGGA | GAGT | CCGT | AGTT | TGAG | GACA | AGGC | CGGT | GGGT | TGTG |
| DRB1-150103 | GGGA | GAGT | CCGT | AGTT | TGAG | GACA | AGGC | CGGT | GGGT | TGTG |
| DRB1-150105 | GGGA | GAGT | CCGT | AGTT | TGAG | GACA | AGGC | CGGT | GGGT | TGTG |
| DRB1-1503 | GGGA | GAGT | CCGT | AGTT | TGAG | GACA | AGGC | CGGT | GGGT | TGTG |
| DRB1-1506 | GGGA | GAGT | CCGT | AGTT | TGAG | GACA | AGGC | CGGT | GGGT | TGTG |
| DRB1-1509 | GGGA | GAGT | CCGT | AGTT | TGAG | GACA | AGGC | CGGT | GGGT | TGTG |
| DRB1-1513 | GGGA | GAGT | CCGT | AGTT | TGAG | GACA | AGGC | CGGT | GGGT | TGTG |
| DRB1-150201 | GGGA | GAGT | CCGT | AGTT | TGAG | GACA | AGGC | CGGT | GGGT | TGGT |
| DRB1-150203 | GGGA | GAGT | CCGT | AGTT | TGAG | GACA | AGGC | CGGT | GGGT | TGGT |
| DRB1-1505 | GGGA | GAGT | CCGT | AGTT | TGAG | GACC | AGGC | CGGT | GGGT | TGTG |
| DRB1-1504 | GGGA | GAGT | CCGT | AGTT | TGAG | GACT | AGGC | CGGT | GGGT | TGTG |
| DRB1-1608 | GGGA | GAGA | ACGT | AGTA | TGAG | GACT | ACAG | CGGT | GGGT | TGGT |
| DRB1-090102 | TTGA | GAGA | ACGT | AGTA | CGAG | GACT | GGAG | AGGT | GGGT | TGGT |

TABLE XII-continued

| Position cDNA | 1111<br>2222<br>5678 | 1111<br>9999<br>3456 | 1112<br>9990<br>7890 | 2222<br>2222<br>4567 | 2222<br>6666<br>1234 | 2222<br>8888<br>3456 | 2222<br>9999<br>6789 | 3333<br>0011<br>8901 | 3333<br>3344<br>8901 | 3333<br>4444<br>2345 |
|---|---|---|---|---|---|---|---|---|---|---|
| DRB1-0902 | TTGA | GAGA | ACGT | AGTA | TGAG | GACT | GGAG | AGGT | GGGT | TGGT |
| DRB1-010102 | TTGA | GAAT | CCGT | AGTA | CGAG | GACC | AGAG | CGGT | GGGT | TGGT |
| DRB1-0108 | TTGA | GAGT | ACGT | AGTA | CGAG | GACC | AGAG | CGGT | GGGT | TGGT |
| DRB1-100101 | TTGA | GAGT | ACGC | AGTA | CGAG | GACC | GGAG | CGGT | GGGT | TGGT |
| DRB1-100102 | TTGA | GAGT | ACGC | .AGTA | CGAG | GACC | GGAG | CGGT | GGGT | TGGT |
| DRB1-0103 | TTGA | GAGT | CCGT | AGTA | CGAG | GACA | ACGA | CGGT | GGGT | TGGT |
| DRB1-0110 | TTGA | GAGT | CCGT | AGTA | CGAG | GACC | AGAA | CGGT | GGGT | TGGT |
| DRB1-0106 | TTGA | GAGT | CCGT | AGTA | CGAG | GACC | AGGC | CGGT | GGGT | TGTG |
| DRB1-0109 | TTGA | GAGT | CCGT | AGTA | CGAG | GACC | AGGC | CGGT | GGGT | TGGT |
| DRB1-010202 | TTGA | GAGT | CCGT | AGTA | CGAG | GACC | AGAG | CCGT | GGGC | TGTG |
| DRB1-010201 | TTGA | GAGT | CCGT | AGTA | CGAG | GACC | AGAG | CCGT | GGGC | TGTG |
| DRB1-0104 | TTGA | GAGT | CCGT | AGTA | CGAG | GACC | AGAG | CCGT | GGGT | TGTG |
| DRB1-010101 | TTGA | GAGT | CCGT | AGTA | CGAG | GACC | AGAG | CCGT | GGGT | TGGT |
| DRB1-0105 | TTGA | GAGT | CCGT | AGTA | CGAG | GACC | AGAG | CCGT | GGGT | TGGT |
| DRB1-0107 | TTGA | GAGT | CCGT | AGTA | CGAG | GACC | AGAG | CCGT | GGGT | TGGT |
| DRB1-0111 | TTGA | GAGT | CCGT | AGTA | CGAG | GACC | AGAG | CCGT | GGGT | TGGT |

General strategy for medium resolution typing is described below:

For medium resolution typing a maximally informative set of marker positions were determined. These consist of positions 98, 414, 539, 282, 571, 368, 256, 292, 238, 270, 453, 527, 502, 81, 268, 559, 92, 123 and 396 of HLA-A (numbering starts at the transcription start position of exon 1), positions 539, 419, 559, 412, 272, 362, 302, 363, 206, 369, 259, 97, 583, 292, 222, 527, 418, 435 and 571 of HLA-B (numbering starts at the transcription start position of exon 1), and positions 125, 196, 197, 227, 261, 286, 299, 308, 341 and 345 of HLA-DRB1 (numbering starts at the transcription start position of exon 1).

In general, the order of the positions is from the most informative to the least informative with respect to the selection criteria of frequent and rare HLA alleles (see list of frequent HLA alleles above). Thus the ten markers (HLA-A and HLA-B) that were selected for the fine typing strategy constitute the first ten markers of the set of 19 markers for the single pass classification into frequent and rare HLA alleles (HLA-A and HLA-B). Like with sequence-based HLA typing there are heterozygous combinations of HLA alleles that can not be resolved. However, there are fewer ambiguities with this method due to the mini-haplotypes that are provided.

Another object of the present invention is the use of said methodology of the invention is for screening of tissue donors, for example, bone marrow donors in registries for frequent and rare HLA types.

The description of the HLA alleles is based on the Anthony Nolan database (www.ebi.ac.uk/imgt/hla/).

BRIEF DESCRIPTION OF THE DRAWINGS

In addition to the aforementioned method, the invention includes yet other arrangements which will emerge from the description that follows, which refers to examples of supports according to the invention, as well as the annexed figures and tables, wherein:

Figure 1:
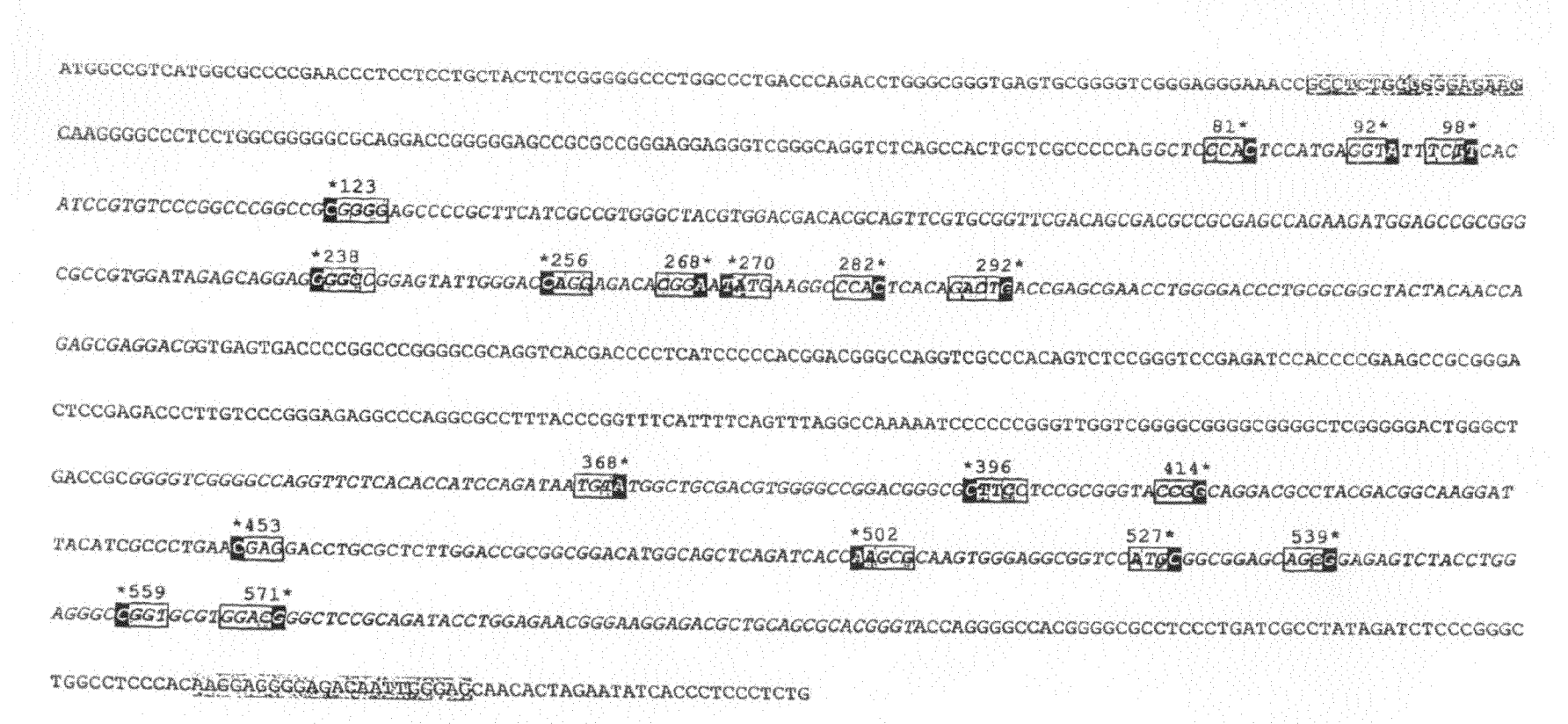

FIG. 1 describes 19 positions covered by mini-haplotyping assays for discrimination of HLA-A mapped onto the HLA-A allele A*010101 as reference. Black boxes indicate an extension position while grey boxes indicate polymorphisms that are captured by the annealing of the respective primer of the primer pool. Pools are used in forward and reverse. Numbering is according to the transcription start of the cDNA.

FIG. 2 describes. 19 positions covered by mini-haplotyping assays for discrimination of HLA-B mapped onto the HLA-B allele B*070201 as reference. Black boxes indicate an extension position while grey boxes indicate polymorphisms that are captured by the annealing of the respective primer of the primer pool. Pools are used in forward and reverse. Numbering is according to the transcription start of the cDNA.

FIG. 3 describes 10 positions covered by mini-haplotyping assays for discrimination of HLA-DRB1 mapped onto the HLA-DRB1 allele DRB1*0101 as reference. Black boxes indicate an extension position while grey boxes indicate polymorphisms that are captured by the annealing of the respective primer of the primer pool. Pools are used in forward and reverse. Numbering is according to the transcription start of the cDNA.

FIG. 4 describes 10 positions covered by mini-haplotyping assays for discrimination of HLA-A mapped onto the HLA-A allele A*010101 as reference for the distinction of subgroups that can then be further analysed. Black boxes indicate an extension position while grey boxes indicate polymorphisms that are captured by the annealing of the respective primer of the primer pool. Pools are used in forward and reverse. Numbering is according to the transcription start of the cDNA.

FIG. 5 describes 10 positions covered by mini-haplotyping assays for discrimination of HLA-B mapped onto the HLA-B allele B*070201 as reference for the distinction of subgroups that can then be further analysed. Black boxes indicate an extension position while grey boxes indicate polymorphisms that are captured by the annealing of the respective primer of the primer pool. Pools are used in forward and reverse. Numbering is according to the transcription start of the cDNA.

Figure 6:
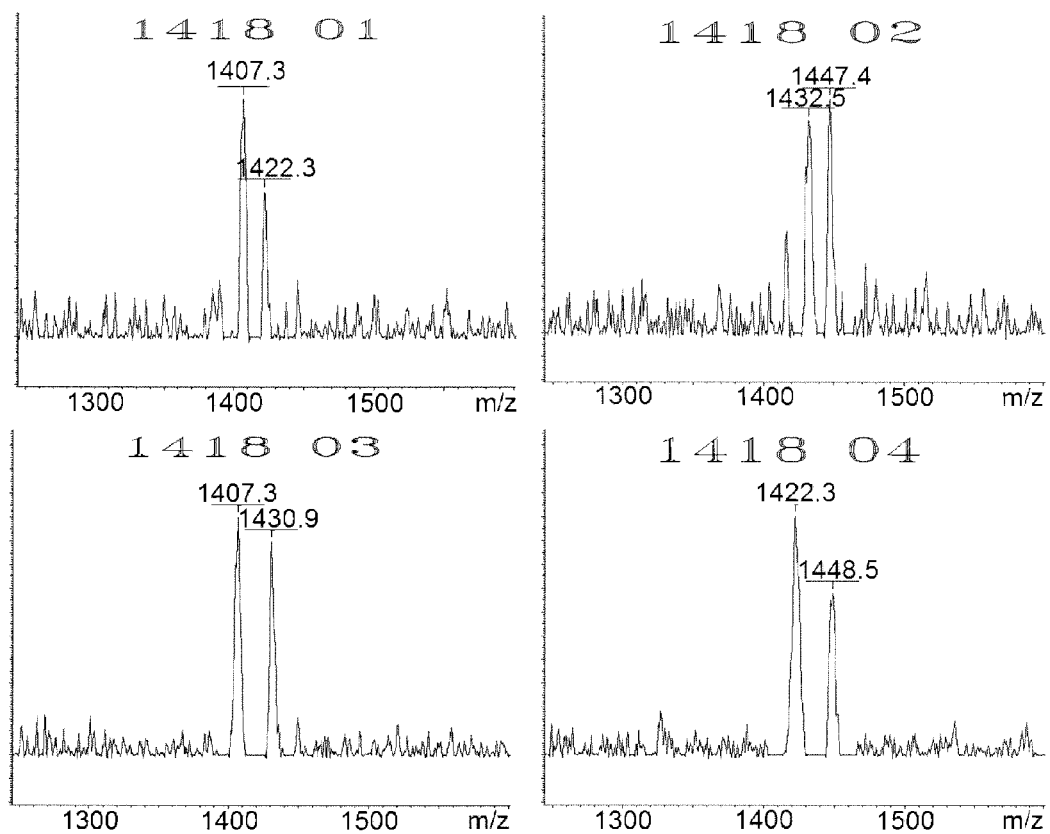
FIG. 6 shows genotyping results of a CEPH family (1418, 01=father, 02=mother, 03=child, 04=child) for position HLA-B__272. 1407.3 Da corresponds to the addition of C to primer 6, 7, 8, or 9; 1422.3 Da corresponds to the addition of T to primer 6, 7, 8, or 9; 1431.4 Da/1430.9 Da corresponds to the addition of A to primer 6, 7, 8, or 9; and 1447.4 Da/1448.5 Da corresponds to the addition of G to primer 6, 7, 8, or 9.

Table I represents HLA-A alleles captured by the 10 markers in the different subgroups and additional positions that have to be typed to resolve the subgroups.

Table II represents HLA-B alleles captured by the 10 markers in the different subgroups and additional positions that have to be typed to resolve the subgroups.

Table III represents HLA-DRB1 alleles captured by the 10 markers in the different subgroups and additional positions that have to be typed to resolve the subgroups.

Table IV represents the list of the individual primers that are required to constitute the pools for mini-haplotyping of HLA-A (19 markers). The 10 markers required for the creation of subgroups are also contained. A refers to the base used to attach the mass/charge tag, CT refers to the mass difference of the mass/charge tag, sp means phosphorothioate group. The product analysed by mass spectrometry includes the base 5' of the most 5' phosphorothioate (sp).

Table V represents the list of the individual primers that are required to constitute the pools for mini-haplotyping of HLA-B (19 markers). The 10 markers required for the creation of subgroups are also contained. ○refers to the base used to attach the mass/charge tag, CT refers to the mass difference of the mass/charge tag, sp means. phosphorothioate group. The product analysed by mass•spectrometry includes the base 5' of the most 5' sp.

Table VI represents the list of the individual primers that are required to constitute the pools for mini-haplotyping of HLA-DRB1 (10 markers). ○refers to the base used to attach the mass/charge tag, CT refers to the mass difference of the mass/charge tag, sp means phosphorothioate group. The product analysed by mass spectrometry includes the base 5' of the most 5' sp.

Table VII represents the resolution that can be generated with the 19 markers for the distinction of the frequent HLA alleles in HLA-A.

Table VIII represents the resolution that can be generated with the 19 markers for the distinction of the frequent HLA alleles in HLA-B.

Table IX represents the resolution that can be generated with the 10 markers for the distinction of the frequent HLA alleles in HLA-DRB1.

Table X represents the list of HLA-A alleles that are resolved with the 10 markers for the creation of subgroups. Each subgroup is separated by an empty line. Frequent alleles are shaded in darker grey, while lighter grey indicates the position that primers are extended onto.

Table XI represents the list of HLA-B alleles that are resolved with the 10 markers for the creation of subgroups. Each subgroup is separated by an empty line. Frequent alleles are shaded in darker grey, while lighter grey indicates the position that primers are extended onto.

Table XII represents the list of HLA-DRB1 alleles that are resolved with the 10 markers for the creation of subgroups. Each subgroup is separated by an empty line. Frequent alleles are shaded in darker grey, while lighter grey indicates the position that primers are extended onto.

EXAMPLES

Example 1

Mini-Haplotyping at Position 272 of HLA-B by the Modified Good-Assay

A locus specific PCR product of exon 2 and exon 3 of HLA-B is amplified with a set of primers published by the International Histocompatibility Working Group, Technical Manuals (Burly, Fernandes-Vina, Gao, Middleton, Noreen, Ren and•Smith; www.ihwg.org/tmanual/Tmcontents.htm). The PCR product is incubated with SAP to remove all excess dNTPs. Then a single base primer extension at position 272 in the PCR amplicon is carried out. The set of primers, to generate the mini-haplotypes is shown in Table V. Thereafter a 5'phosphodiesterase digest is applied to reduce the primers to a core sequence. After alkylation of the DNA backbone of the mini-haplotype fragments the products are transferred onto a MALDI target pre-coated with matrix. Alternatively the matrix solution can be mixed with the samples and transferred onto the MALDI target to dry. The MALDI target is introduced into a MALDI mass spectrometer and analysed. The mass spectra show one or two mass peaks and that correspond to specific mini-haplotypes.

PCR:

Forward primer, BAmp1 5'-G GGT CCC AGT TCT AAA GTC CCC ACG3'(1.875 µmol), reverse primer, BAmp2 5'-CC ATC CCC GGC GAC CTA TAG GAG ATG-3' (1.875 µmol) an BAmp3 5'-AGG CCA TCC CGG CGG GCG ATC TAT-3' (1.875 µmol), 0.25 µl 10×PCR buffer (HiFi Platinum Taq)), 0.3 µl MgSO$_4$ (50 mM), 0.2 µl of a mix of each dCTP, dATP, dGTP and dTTP (2 mM each), 0.25 U engineered DNA polymerase (HiFi Platinum DNA Polymerase; Invitrogen) and 5 ng DNA fill to 3 µl with water. Cycling: 1. 94° C. 3 min, 2. 94° C. 20 sec, 3. 64° C. 30 sec, 4. 72° C. 30 sec, steps 2 to 4 are repeated 35 times, 5. 72° C. 5 min.

SAP Digest:

1.75 µl of 50 mM Tris-HCl and 0.25 µl SAP, (USB corporation, Cleveland, USA) are to add to the PCR product and this has to be incubated for 60 min at 37° C., followed by an incubation at 90° C. for 10 min to denature the SAP enzyme.

Single Base Primer Extension:

To the SAP treated PCR product 2 µl of an extension mix is to add. This mix contains 15 mM MgCl$_2$, 0.1 mM of each of the four α-S-ddNTPs, 5 µmol of the extension primers set and 0.4 U of Thermosequenase. Cycling: 1. 94° C. 2 min, 2. 94° C. 15 sec, 3. 58° C. 20 sec, 4. 72° C. 20 sec, steps 2 to 4 are repeated 50 times.

PDE Digest:

To the extension product has to be added 0.5 µl 0.5 M acetic acid and 1.5, µl PDE (5.1 U) and incubate for at lease 120 min at 37° C.

Alkylation:

The alkylation is carried out by adding 21 µl of an alkylation mix and incubate for 15 min at 40° C. Th alkylation mix contains 377 parts water free acetonitrile, 15 parts of 2M triethylamine/CO$_2$ (pH~7.5), 75 parts 2 mM Tris-HCl and 174 parts of methyliodine.

The alkylation is to stopped by adding 10 µl deionised water. 5 µl of the resulting upper phase are to dilute in 10 µl 40% acetonitrile.

For MALDI target preparation and measurement with the MALDI mass spectrometer 0.5 µl of the final dilution are transferred onto a MALDI target pre-coated with matrix (α-cyano-4-hydroxycinnamic acid methyl ester). Measurement was carried out in a Broker Autoflex with typically −18 kV acceleration voltage, pulsed ion extraction with a delay of 200 ns, and detection in linear detection mode. Results for CEPH family 1418 are shown in FIG. 6.

Example 2

HLA-DR Typing by the GOOD-Assay

A locus specific•PCR for HLA-DRB is carried out. Therefore a set of allele-specific primers as listed below is used. These primers are published by J. Wu et al. in http://www.i-hwg.org/tmanual/TMcontents.htm Chapter 10-B.

| Name | Sequence |
|---|---|
| Amp1_DRB1_f20 | 5'-TTCTTGTGGSAGCTTAAGTT-3' |
| Amp2_DRB1_f21 | 5'-TTCCTGTGGCAGCCTAAGAGG-3' |
| Amp3_DRB1_f22 | 5'-CACGTTTCTTGGAGTACTCTAB-3' |
| Amp3-2_DRB1_f23 | 5'-CGTTTCTTGGAGTACTCTACGGG-3' |
| Amp3-3_DRB1_f23 | 5'-CGTTTCTTGGAGTACTCTACGTC-3' |
| Amp4_DRB1_f21 | 5'-GTTTCTTGGAGCAGGTTAAAC-3' |
| DR7_DRB1_f20 | 5'-CCTGTGGCAGGGTAARTATA-3' |
| DR9_DRB1_f18 | 5'-CCCAACCACGTTTCTTGA-3' |
| DR10_DRB1_f19 | 5'-AGACCACGTTTCTTGGAGG-3' |
| AmpB_DRB1_r18 | 5'-TCGCCGCTGCACYGTGAA-3' |

This set of primers carries a high risk of co-amplifying genes for the other HLA-DRB chains, which results in unclear results. However, this is currently the best available option for the PCR of HLA-DRB1. In order to resolve the problem an additional mini-haplotyping test can be added. The mini-haplotyping assay HLA-DRB_122-126 gives good resolution of HLA-DRB genes and allows the verification of results produced for typing of HLA-DRB1 PCR products. The identification of HLA-DRB1 genes is possible, as well as the identification of other amplified HLA-DRB genes which are present is possible. The set of primers listed below is used for the primer extension reaction. The details of the protocol are identical to example 1.

| Name | Sequence | CT | Masses Primer | A | C | G | T |
|---|---|---|---|---|---|---|---|
| HLADR_1221_2f20 | TGAAGAAATGACACTCAspTspG'spT | 0 | 1487.5 | — | — | — | 1805.7 |
| HLADR_1222_2f20 | TGCAGAAATAGCACTCGspTspG*spT | 0 | 1503.5 | — | — | — | 1821.7 |
| HLADR_1223_2f20 | TGAAGAAATGACACTCAspGspG*spT | 0 | 1512.5 | — | — | — | 1830.7 |
| HLADR_1224_2f20 | TGAAGAAATGACACTTAspTspA*spT | 0 | 1471.5 | — | — | — | 1789.7 |
| HLADR_1225_2f20 | TGAAGAAATGACACTCCspCspT*spC | — 14 | 1510.6 | — | — | — | 1814.8 |
| HLADR_1226_2f20 | TGAAGAAATRACACTCAspCspC*spC | — 28 | 1418.4 | 1717.7 | 1693.6 | 1733.7 | — |
| HLADR_1227_2f20 | TGAAGAAATGACACTCAspTspA*spC | — 14 | 1456.5 | — | — | — | 1760.7 |
| HLADR 1228_2f20 | TGAAGAAWTGACACTCAspGspA*spC | 0 | 1481.5 | — | — | — | 1799.7 |
| HLADR_1229_2f20 | TGAGGAAATGACACTCAspCspA*spC | — 14 | 1441.5 | — | — | 1770.8 | 1745.7 |
| HLADR_12210_2f20 | TGAAGATATGACACTCAspCspA*spC | — 14 | 1441.5 | — | — | 1770.8 | 1745.7 |
| HLADR_12211_2f20 | TGAAGAAATGACAYTCAsoAsoA*spC | 0 | 1465.5 | — | — | — | 1783.7 |

Of the thirteen possible mini-haplotypes, four represent genes other than HLA-DRB1. The mini-haplotype GTGTT (1821.7 Da), AACAC in sense direction, represents with 100% certainty co-amplification of the HLA-DRB9 gene. The mini-haplotype ATACT (1760.8 Da), AGTAT in sense direction, represent either all HLA-DRB1*07 alleles (except HLA-DRB1*070102) or co-amplification of the HLA-DRB5 gene. The type TGTGT (1745.7 Da), AGTGT in sense direction, correspond to co-amplification or all variations of the HLA-DRB4 or HLA-DRB6 genes. Finally the type AGACT (1799.7 Da), AGTCT in sense direction, represent besides HLA-DRB1*1130 and HLA-DRB1*1446 also co-amplification of all variants of HLA-DRB3 and HLA-DRB7 genes.

The invention claimed is:

1. A kit, comprising the pool of primers of Table IV.
2. A kit according to claim 1, further comprising the pool of primers of Table V or Table VI.

* * * * *